(12) United States Patent
Batard et al.

(10) Patent No.: US 6,376,753 B1
(45) Date of Patent: Apr. 23, 2002

(54) **PURIFIED CYTOCHROME P450 POLYPEPTIDE CYP76B1 FROM *HELIANTHUS TUBEROSUS* AND ITS APPLICATIONS AS BIOCATALYST IN PARTICULAR FOR THE DEGRADATION OF ENVIRONMENTAL POLLUTANTS AND FOR ALTERING THE RESISTANCE OF PLANTS SENSITIVE TO PHENYLUREA FAMILY OF HERBICIDES**

(75) Inventors: Yannick Batard, Strasbourg; Tiburce Robineau, Schittigheim; Francis Durst, Brumath; Daniele Werck-Reichhart, Dingsheim; Luc Didierjean, Orbey, all of (FR)

(73) Assignee: Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 09/126,420

(22) Filed: Jul. 30, 1998

Related U.S. Application Data

(60) Provisional application No. 60/054,351, filed on Jul. 31, 1997.

(51) Int. Cl.[7] ........................... C12N 15/82; C12N 5/04; C12N 15/29; C12N 15/00; A01H 5/00
(52) U.S. Cl. ....................... 800/298; 800/300; 435/410; 435/418; 435/419; 435/255.2; 435/320.1; 536/320.1; 536/23.1; 536/23.2; 536/23.6; 536/23.7
(58) Field of Search ............................... 536/23.1, 23.6; 530/300; 424/192.1; 800/314, 317.3, 312, 308, 320.1, 320.3, 320.2, 278, 288, 290, 295, 296, 300, 300.1; 435/69.1, 468, 410, 412, 419, 243, 255.1, 320.1

(56) References Cited

PUBLICATIONS

Pauli et al. The Plant Journal. 1998. vol. 13(6): 793–801.*

Shiota et al. Plant Physiol. 1994. vol. 106: 17–23. see also the attached Mpsearch result (#7).*

Boerboom; (title: Herbicide made of action reference. Oct. 1998 was downloaded from internet on Nov. 9, 2000. URL: http://144.92.198.2541soubelth/herbclass/htm.*

Agronomy Dept., UW—Madison, Bulletin.*

* cited by examiner

*Primary Examiner*—Amy J. Nelson
*Assistant Examiner*—Ousama M. F. Zaghmout
(74) *Attorney, Agent, or Firm*—Finnegan, Henderson, Farabow, Garrett & Dunner, L.L.P.

(57) ABSTRACT

The present invention relates to the gene CYP76B1 of a cytochrome P450 which has been isolated from *Helianthus tuberosus* tuber. The expression of this gene in yeast has shown that it encoded an enzyme very actively catalysing the O-dealkylation of various exogenous molecules with a high efficiency, such as phenylureas. The expression of CYP76B1 is strongly induced in plants brought into contact with certain exogenous metals or organic compounds. This induction may be exploited for the detection of environmental pollutants. CYP76B1 can be also used to alter the resistance of plants sensitive to this family of herbicides and for soil and groundwater bioremedation.

10 Claims, 17 Drawing Sheets

FIG. 2

```
E3C
76B1  ggaagagaccaacgtatggatgactcactagagtcaagccacacgattttggagtccaaggctgatgctccgaggtcatgattcgatttcgattcccgttggcgctgacgaagaatatgcctggcatccactgaaacgt  1344
       G R D P T V W D D S L E F K P Q R F L E S R L D V R G H D F D L I P F G A G R R I C P G I P L A T R  440

E3C
76B1  atggtccctatcatgttggctcattactcaataattgactgaaaattgcactgaagttccatagatgttttgaacagatgtttggaacagatgtttggacacatgatcgttcatgatgttgttccaataccattgaac  1494
       M V P I M L G S L L N N F D W K I D T K V P Y D V L D M T E K N G T T I S K A R P L C V V P I P L N  490
                                                              g E3C
76B1  tagcatccattcatcttgtttgaagtccgataatcaagcgcaacgagttggaagagaagaaaaacgagcaactttatttgttattagtcaaattgttactgttattttattagaactggg ccgt  1643
       *                                                                                                                                491

E3C             a      ....taattt
76B1  aggccatgtccagtgggtcaaacaattagtgtccagtaggttaatattatgtaatttgttttgcccctaactgtgaaccggttgttggc  1737
                                                                                          (SEQ ID NO:2)
                                                                                          (SEQ ID NO:1)
```

TABLE A: REFERENCE ACTIVITIES

| MICROSOMES | 7-METHOXYRESORUFIN O-DEETHYLASE |
|---|---|
| DORMANT TUBER | 0.053 ± 0.004 |
| SURVIVAL 48h ON WATER | 0.036 ± 0.001 |
| WATER + DMSO 0.25% (v/v) | 0.033 ± 0.001 |

TABLE B: ABBREVIATIONS AND CONCENTRATIONS OF XENOBIOTICS USED.

| | EFFECTOR | ABBREVIATION | CONCENTRATION |
|---|---|---|---|
| CONTROLS | DOEMANT TUBER<br>WOUNDING<br>SOLVENT | TO<br>$H_2O$<br>DMSO* | |
| METALIC IONS | MANGANESE CHLORIDE<br>CADMIUM CHLORIDE<br>MERCURIC CHLORIDE | $Mn^{2*}$<br>$Cd^{2*}$<br>$Hg^{2*}$ | 25 mM<br>2.5 mM<br>2.5 mM |
| DRUGS | AMINOPYRINE<br>PHENOBARBITAL<br>CLOFIBRATE<br>B-NAPHTHOFLAVONE | AP<br>PB<br>Clo<br>bNF* | 20 mM<br>8 mM<br>5 mM<br>1.7 mM |
| POLLUTANTS | BENZO(A)PYRENE<br>3-METHYLCHOLANTHRENE<br>DIETHYLHEXYLPHTHALATE<br>ISOSAFROLE | BaP*<br>3MC<br>DEHP<br>iso | 260 mm<br>240 mm<br>5 mM<br>50 AND 100 mM |
| PLANT SECONDARY METABOLITES | FLAVONE<br>8-METHOXYPSORALEN | Flav*<br>8MP* | 1.7 mM<br>50 mM |
| PESTICIDES | NAPHTHALIC ANHYDRIDE<br>LINDANE<br>BIPHENYL | NA*<br>Lin<br>Bip* | 150 AND 300 mM<br>1 mM<br>6.5 mM |

\* = IN DMSO

*FIG. 8 (CONT)*

A. CONTROL YEAST: TRANSFORMED WITH EMPTY PLASMID pYeDP60

B. YEAST TRANSFORMED WITH THE PLASMID pYeDP60 CONTAINING THE CODING SEQUENCE CYP 76 B 1

A. CONTROL YEAST: TRANSFORMED WITH THE EMPTY PLASMID pYeDP60

B. YEAST TRANSFORMED WITH THE PLASMID pYeDP60 CONTAINING THE CODING SEQUENCE CYP 76 B 1

PURIFIED CYTOCHROME P450 POLYPEPTIDE CYP76B1 FROM *HELIANTHUS TUBEROSUS* AND ITS APPLICATIONS AS BIOCATALYST IN PARTICULAR FOR THE DEGRADATION OF ENVIRONMENTAL POLLUTANTS AND FOR ALTERING THE RESISTANCE OF PLANTS SENSITIVE TO PHENYLUREA FAMILY OF HERBICIDES

This application claims priority to U.S. Provisional Application Ser. No. 60/054,351, filed Jul. 31, 1997.

BACKGROUND OF THE INVENTION

The gene CYP76B1 of a cytochrome P450 has been isolated from *Helianthus tuberosus* tuber. The expression of this gene in yeast has shown that it encoded an enzyme very actively catalyzing the O-dealkylation of various exogenous molecules with a high efficiency. It could, for this reason, be used as oxygenase, as biocatalyst either for the degradation of environmental pollutants or for the biosynthesis of organic compounds such as medicaments, perfumes or pigments.

The expression of CYP76B1 is strongly induced in plants brought into contact with certain exogenous metals or organic compounds. This induction may be exploited for the detection of environmental pollutants.

CYP76B1 metabolizes with high efficiency a wide range of xenobiotics, including alkoxycoumarins, alkoxyresofurins and several herbicides of the class of phenylureas. CYP76B1 also catalyzes the mono- and didealkylation of phenylureas such as the two herbicides chlortoluron and isoproturon, with turnover rates comparable to those reported for physiological substrates and produces non-phytotoxic compounds. CYP76B1 can therefore be used to alter the resistance of plants sensitive to this family of herbicides and for soil and groundwater bioremediation.

1. Field of Invention

The present invention relates to purified polypeptides and DNA sequences of CYP76B1, a cytochrome P450 molecule, which has been isolated from *Helianthus tuberosus* tuber, and a method for preparing the same. It further relates to methods for detecting environmental chemical pollution comprising determining the presence of CYP76B1 polypeptide. It furthermore relates to methods for producing transgenic plants incorporating a gene or a gene fragment CYP76B1 in a bioremediation perspective and for an agricultural use.

2. Description of the Related Art

Plants respond to environmental stress with a wide range of adaptative changes, including the induction of defense mechanisms. Plants defense against the attack from pathogens and predators, or against changes in environmental conditions like drought, salinity, increased UV light or extreme temperatures have been largely documented. Much less is known about plant response to chemical agression. Increasing amounts of pesticides and other industrial chemicals are introduced in the environment without real knowledge of their impact on plant metabolism, development and organoleptic properties. Evidence has been obtained that plant can accumulate, transform and store exogenous chemicals as conjugated, compartmented or bound residues (2, 3). The enzymatic equipment allowing plants to cope with the toxicity of xenobiotics is very similar to the enzymes involved in the metabolism of drugs in the liver of mammals (4, 5, 6, 7). It includes reductive, oxidative and hydrolytic enzymes, various transferases for the formation of conjugated metabolites, and systems for the regeneration of antioxidants like glutathione. The cytochrome P450s constitute one of the principal classes of enzymes responsible for this metabolism (12, 7). A characteristic common to both animal and plant enzymes is their inducibility by drugs and other exogenous toxins.

As in animals, cytochromes P450 form, in plants, the main class of oxidases involved in the metabolism of exogenous molecules, including herbicides and pollutants (8, 9, 10, 11, 12). They have been shown to catalyze hydroxylation, S-oxidation, N- or O-dealkylation of environmental chemicals, thereby increasing their hydrophylicity and allowing their subsequent conjugation or immobilization. Increased P450 content and enzymatic activities following treatment with metals or organic molecules including drugs, herbicides, herbicide safeners, solvents and industrial pollutants have been observed in many plant species (1, 11, 13, 14, 15, 16, 17, 18, 19, 20, 21, 22). The induction of certain cytochrome P450s and of their enzymatic activities is currently used as an early marker of chemical pollution in marine environments in particular (46, 47, 26). Studies, which are very preliminary, have suggested that an induction of P450s may be detected in a polluted environment (47). In the case of the cinnamate 4-hydroxylase (C4H), increase in catalytic activity induced by chemicals was paralleled by an increase in the steady-state level of CYP73A1 transcripts (22).

7-Ethoxycoumarin is a synthetic fluorescent molecule, very similar to natural coumarins, widely used to assay the catalytic activity of cytochromes P450 involved in the metabolism of foreign compounds (23, 24). Increase in 7-10 ethoxycoumarin O-deethylase (ECOD) activity, fast and easy to measure, has often been taken as an index of the induction of these P450s in animals following environmental chemical stress (25, 26). P450-dependent ECOD activity was detected in several plant species (27, 28, 29). In both dicots and monocots, the activity was found strongly induced in response to exogenous chemicals (1, 27, 29). A more detailed analysis, performed on *Helianthus tuberosus* tuber, showed that the induction of ECOD activity was often several fold higher than that of a physiological activity like C4H (22). ECOD thus appeared as a good potential marker of chemical contamination. Fluorescence assay of ECOD activity is impossible in extracts from green plants (interference with chlorophyll).

Because of the enormous losses caused by indesirable plant growth, the problem of weed control is a major one in the agricultural economy. Herbicides are broadly used for controlling the growth of weeds in crops. Among herbicides, compounds show broad spectrum control, making them useful where complete eradication of vegetation is needed, and others show selective control with tolerance to agronomic crops. New methods for producing transgenic plants resistant to herbicides have been developed (EP 730030). These transgenic plants are transformed and generally express or overexpress an enzyme capable of detoxifying the chosen herbicide, making them resistant to that herbicide.

Among the herbicides or pesticides which have been developed, many of them are substitued urea or thiourea compounds, represented by the formula: R1R2N—CO—NR3R4 or R1R2N—CS—NR3R4, and are used for destruction and prevention of weeds (WO 90/06680; WO 95/22547; U.S. Pat. Nos. 2,655,444; 2,655,447; 2,857,430; 3,912,496; 5,393,733; 5,512,535 FR 69 03 235; FR 71 06 517).

Most of these substituted urea or thiourea compounds have cyclic groups and amine radicals, which can be substituted with alkoxy radicals and/or alkyl radicals. Among them, the phenylurea class which can be represented by the formula: (substituted-phenyl)—NH—CO—NR1R2, in which the phenyl group and the secondary amine radical can be substituted with alkoxy and/or alkyl radicals. This phenylurea class can be illustrated by chlortoluron (N-(3-chloro-p-tolyl)-N',N'-dimethylurea) and by isoproturon (N-(4-isopropylphenyl)-N',N'-dimethylurea).

The first coding sequence of plant P450 (CYP73A1) capable of metabolizing an herbicide (i.e. capable of hydroxylating chlortoluron) has been isolated in the laboratory (33). The reaction turnover is however too low (0.014 $min^{-1}$) for the enzyme to be capable of substantially increasing the resistance of plants to chlortoluron.

It has, moreover, been demonstrated that the resistance of plants to herbicides (chlortoluron* and chlorsulfuron) could be manipulated (increased or decreased) by genetic transformation using animal or bacterial P450 genes (48, 49, 50). No experiment of this type has been carried out up until now with plant genes. The work carried out with bacterial and animal genes strongly suggests, however, that it is possible to transfer the tolerance to herbicides from one plant to another.

The advantage of using plant genes is two-fold: i) the efficiency of the biotransformation with the plant P450 appears to be substantially greater than that obtained with the animal P450s tested, ii) the transformation of plants with plant genes is accepted better by public opinion.

The present invention is directed to purified CYP76B1 polypeptide and its biologically active fragments.

The invention further relates to nucleic acids fragments encoding the polypeptide or its biologically active fragments and specific oligonucleotides probes or primers which are obtained from these sequences.

A further object of the invention is to provide cloning and/or expression vectors comprising at least one of the said nuleic acid sequence, and host cells transformed with such cloning and/or expression vectors under conditions allowing the replication or/and the expression of said nucleic acid sequences. In another aspect, this invention provides methods for producing CYP76B1 recombinant polypeptides or their biologically active fragments by transformed host cells.

The invention is also directed to monoclonal and polyclonal antibodies or their fragments which are specific for the polypeptide defined above.

The invention further comprises methods for detecting abnormal expression or overexpression of the said polypeptide in biological plant samples comprising determining the accumulation of CYP76B1 polypeptides in accordance with immunological techniques or evaluating the accumulation of CYP76B1 mRNA transcripts accumulation in accordance with molecular hybridization techniques. The use of these methods for detecting environmental chemical pollution is also an aspect of this invention.

According to a further aspect, the invention relates to a method for producing organic compounds which are obtained by organic substrates biotransformation using the CYP76B1 oxygenase activities and a method for selecting organic compounds capable of being biotransformed by the polypeptides.

The present invention also concerns a method for screening organic compounds capable of being biotransformed by the CYP76B1 polypeptides oxygenase activities, especially for selecting herbicides or pesticides.

Furthermore the invention relates to a method for screening plant cells or plants which are resistant to a given herbicide or pesticide comprising transforming a plant cell or plant with a vector of the invention, testing the plant cell or plant for its ability to grow in the presence of normally inhibitory concentration of said herbicide or pesticide and selecting the plant cells or the plants which are resistant to the herbicide or to the pesticide.

The invention also comprises a transgenic plant having increased resistance to herbicides or pesticides wherein said plant is transformed by a vector according to the invention.

The invention finally relates to a method for the bioremediation comprising transgenic plants which express or overexpress the CYP76B1 gene.

The object of the present invention relates to a purified polypeptide which comprises an amino acid sequence selected from:
  a) the amino acid sequence SEQ ID NO 1,
  b) the amino acid sequence SEQ ID NO 2,
  c) a fragment of the amino acid sequence SEQ ID NO 1 or SEQ ID NO 2 which retains at least one of their biological activities,
  d) an amino acid sequence of a CYP76B1 polypeptide analogue.

In the description the following definitions are used:
CYP76B1 polypeptide or CYP76B1 protein: a polypeptide having amino acid sequence comprising all or part of the CYP76B1 or E3C amino acid sequences, respectively sequence SEQ ID NO 1 and sequence SEQ ID NO 2, or one of their fragments or derived fragments which are biologically active.
CYP76B1 analogue: a polypeptide or molecule which results from a genetic or chemical modification such as mutation, deletion, addition, substitution and/or chemical modification of at least one amino acid of the CYP76B1 polypeptide sequence, said polypeptide retaining at least one of the CYP76B1 polypeptide biological activities.
Biologically active: capable of providing enzymatic activity, especially oxygenase activities, and/or capable of being recognized by CYP76B1 polypeptide specific antibodies and/or capable of inducing antibodies which recognize these polypeptides.

Among the polypeptides of the invention, the polypeptide which has the amino acid SEQ ID NO 1 or SEQ ID NO 2, is preferred.

The invention further relates to a DNA sequence isolated encoding a polypeptide according to the invention.

In a preferred embodiment the invention relates to DNA sequence selected from:
  a) DNA sequence SEQ ID NO 1,
  b) DNA sequence SEQ ID NO 2,
  c) a DNA sequence capable of specifically hybridizing with DNA sequence SEQ ID NO 1 or DNA sequence SEQ ID NO 2, or with their complementary sequence or their corresponding mRNA sequence,
  d) a DNA sequence encoding a CYP76B1 analogue.

In a more preferred embodiment the invention comprises DNA sequence isolated of gene which encodes CYP76B1 or E3C polypeptide.

The different nucleic acid fragments of the invention can be obtained by screening cDNA or genomic DNA librairies using probes prepared from a DNA sequence encoding the CYP76B1 polypeptide. Such cDNA or genomic DNA libraries can be screened by standard molecular biological techniques. Oligonucleotide probes or primers which are capable of strongly and specifically hybridizing with any of the DNA sequences according to the invention, are included in the invention.

Oligonucleotides probes, primers or CYP76B1 polypeptides can also be obtained by chemical synthesis, and are included in the invention.

Preferably the probes or the primers according to the invention comprise at least 10 nucleotides and can be as long as the full-length sequence is encoding the CYP76B1 polypeptide. Among the shortest probes which contain about 10 to 20 nucleotides, the suitable conditions for hybridization correspond to stringent conditions which are normally used in standard methods, described for example in the experimental procedure. Preferentially the probes according to the invention are preliminary labeled before use, for example radio-labeled, chemiluminescent-labeled, fluorescent-labeled or enzyme-linked probes.

The present invention also comprises oligonucleotides primers which specifically hybridize with one of the DNA sequences according to the invention or which comprise the DNA sequence encoding one of the polypeptides and allows the amplification of the sequence by the PCR method or by one of its variants. Advantagously the oligonucleotide probes or primers comprise a sequence selected from:

a) sequence SEQ ID NO 3:
5'-ATATATGGATCCATGGATTTTCTTATAATAGTG AGTAC (sense), b) sequence SEQ ID NO 4:
5'-TATATAGAATTCATGCTAGTTCAATGGTATTG GAACAACAC (reverse).

The DNA sequence according to the invention can be used for the preparation of CPY76B1 polypeptides or analogues. Such recombinant polypeptides can be produced by standard recombinant DNA techniques. Effective production system of recombinant polypeptides requires to have at one's disposal a vector, i.e. plasmid or viral origin, and a compatible host cell. The vector comprises, at least a DNA sequence according to the invention under the control of element expression in the host cell. The host cell can be chosen among procaryote systems, such as bacteria, eucaryote systems, such as yeasts, in particular *Saccharomyces cerevisiae,* or plant cells, or any system which is advantageously available. Such vectors can be prepared in accordance with standard techniques, and the resulting clones can be introduced in the appropriate host cell by using well known methods such as electroporation.

The present invention comprises a vector for the cloning or/and the expression of a polypeptide according to the invention, containing a DNA sequence according to the invention.

In a preferred embodiment the vector is a plasmid vector.

The cells can be prepared by introducing a nucleotide sequence inserted in a vector, as defined above, into the host cells then these cells are cultured under conditions allowing the replication or/and the expression of transfected nucleic acid fragment. The invention also comprises host cell transformed by a vector according to the invention. Preferably the cell is *Saccharomyces cerevisiae* or a plant cell.

This invention further comprises methods for the production of a polypeptide comprising culturing cells according to the invention under conditions allowing the expression of polypeptide and recovering the said polypeptide from the culture medium. The polypeptide obtained by these methods, are also included in the invention.

The monoclonal or polyclonal antibodies or their fragments, labeled antibodies which specifically bind to a polypeptide according to the invention, are included in the invention.

Polyclonal antibodies can be prepared using standard methods from an animal which has been immunized against CYP76B1 polypeptide, produced for example by genetic recombination. Monoclonal antibodies can be prepared according to the standard method for culturing hybridomas described by Köhler and Milstein (Nature 1975). Antibodies according to the invention or their fragments, such as Fab or F(ab')2 fragments, can be labeled or immuno-conjugated. The invention comprises a method for the purification or the detection of a polypeptide according to the invention comprising using an antibody according to the invention. Biochemical pollution marker comprising an antibody or an oligonucleotide probe according to the invention are also included in the invention.

The invention furthermore comprises method for detecting abnormal expression or overexpression of polypeptides according to the invention from a biological plant sample comprising bringing said sample into contact with an antibody according to the invention under conditions allowing the formation of an immunological complex between said polypeptides and said antibody, and detecting the formation of an immunological complex.

The invention also comprises a method for detecting abnormal expression or overexpression of polypeptides according to the invention from a biological plant sample comprising bringing said sample into contact with an olignoucleotide probe according to the invention under conditions allowing the formation of an hybridization complex between said oligonucleotide probe and an mRNA sequence encoding said polypeptide, and detecting the formation of an hybridization complex.

These methods more especially allow the detection of abnormal accumulation of CYP76B1 polypeptides or their mRNA transcripts in a biological sample, abnormal accumulation which is induced by metals or organic compounds. More generally, antibodies and probes according to this invention can advantageously be used in any situation where expression or overexpression of CYP76B1 polypeptides must be examined. The invention also comprises the use of these methods for detecting environmental chemical pollution.

The expression of the CYP76B1 polypeptide in yeast has shown that it encoded an enzyme very actively catalyzing the dealkylation of exogenous substrates such as alkoxycoumarin, alkoxyresorufin or phenylurea herbicides. The CYP76B1 polypeptide oxygenase activities can therefore be used for biosynthetizing organic compounds such as medicaments, perfumes or pigments. This invention comprises method for biosynthetizing organic compound comprising bringing an organic substrate of the polypeptide according to the invention into contact with said polypeptide under conditions allowing the synthesis of said organic compound by biotransformation of the substrate, and recovering said organic compound.

CYP76B1 polypeptide very actively catalyzes the O-dealkylation of various exogenous compounds and the mono- and didealkylation of herbicides of the phenylurea family, such as chlortoluron or isoproturon. CYP76B1 polypeptide very effectively attacks the N-dimethyl group which it oxidizes into an amine. All the phenylureas, and numerous other pesticides, carry this functional group and are therefore potential substrates of CYP76B1 polypeptide. Such a metabolism abolishes the phytotoxicity of these herbicides or pesticides.

SUMMARY OF THE INVENTION

This invention comprises a method for screening organic compounds capable of being biotransformed by a polypeptide according to the invention comprising bringing said organic compounds into contact with said polypeptide under conditions allowing the biotransformation of said organic compound, analyzing the obtained compounds and selecting the biotransformed organic compounds.

In a preferred embodiment, the organic compound is an herbicide or a pesticide.

CYP76B1 polypeptide can consequently be used to alter the resistance of plants sensitive to this family of herbicides or pesticides which are metabolized by the CYP76B1 oxygenase activities. Methods of transforming plant cells or plants with a nucleic fragment encoding a given polypeptide and a regulatory sequence providing expression of the given polypeptide in the plant cells are well known. The nucleic acid fragments according to the invention can be used to transform a wide variety of agricultural plants including dicotyledons such as tobacco, cotton, soybean, melon, and monocotyledons such corn, wheat or rice.

The invention comprises a method for screening plant cells or plant which are resistant to a given herbicide or pesticide comprising transforming a plant cell or plant by a vector according to the invention, testing the plant cell or plant for its ability to grow in the presence of a normally inhibitory concentration of said herbicide or pesticide and selecting the plants cells or the plant which are resistant to the herbicide or to the pesticide.

Preferably, said herbicide or pesticide is of the phenylurea family. In a more preferred embodiment said herbicide is the chlortoluron or the isoproturon.

The invention also comprises transgenic plant having increased resistance to herbicides or pesticides wherein said plant is transformed by a vector according to the invention.

The invention finally comprises a method comprising transgenic plant according to the invention for the bioremediation and transgenic plant according to the invention which is an agricultural plant.

BRIEF DESCRIPTION OF THE DRAWINGS

FIG. 2: The nucleotide and deduced amino acid sequences of the *Helianthus tuberosus* CYP76B1 cDNAs, corresponding to the sequences SEQ ID NO 1 and SEQ ID NO 2. Nucleotides which differ in E3C from those in 76B1 are indicated above the 76B1 nucleotide sequence. The putative limits of the D and E helices are delineated.

FIG. 3: Amino acid alignment of CYP76B1 with the most closely related plant and animal P450s. CYP76A1 and CYP76A2 from *Solanum melanonga* (activity unknown, 41.1 and 38% amino acid identity, respectively), CYP71A1 from *Persea americana* (isoprenoid metabolizing, 38.5%), CYP75A1 from *Petunia hybrida* (flavonoid 3',5'-hydroxylase, 37.9%), CYP80 from *Berberis stolonifera* (berbamunine synthase, 35.5%), CYP73A1 from *Helianthus tuberosus* (cinnamate 4-hydroxylase, 31%), mouse CYP2D10 (testosterone 16α-hydroxylase, 28.8%), rat CYP1A1 (benzo(a)pyrene hydroxylase, 7-ethoxyresorufine O-deethylase, 7-ethoxycoumarine O-deethylase, 28.8%), human CYP17A1 (steroid 17α-hydroxylase, 27%), and rat CYP2A3 (coumarin 7-hydroxylase, 26.8%).

Table A gives the demethylase activities in the reference tissues (dormant, incubated in water or in the presence of DMSO, used as solvent for certain inducers).

Table B gives the meaning of the abbreviations, as well as the concentrations used.

Figure 9:
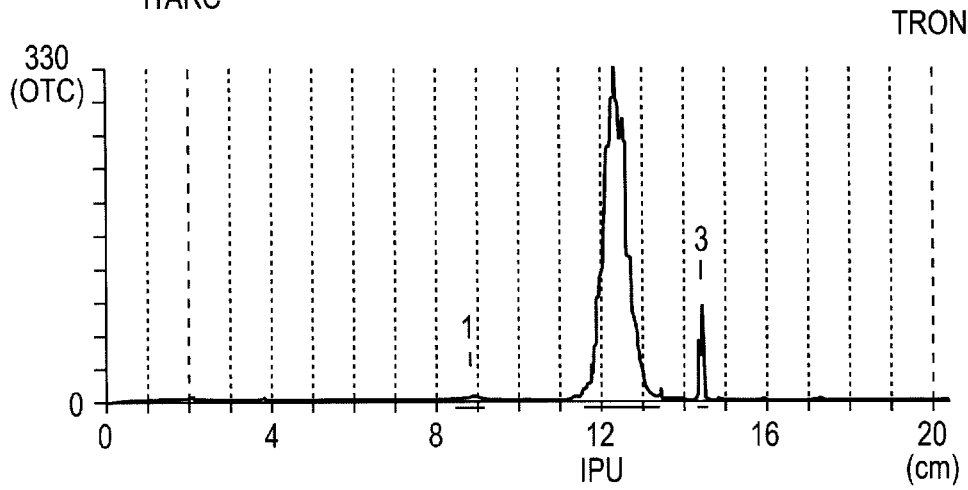
Figure 9:
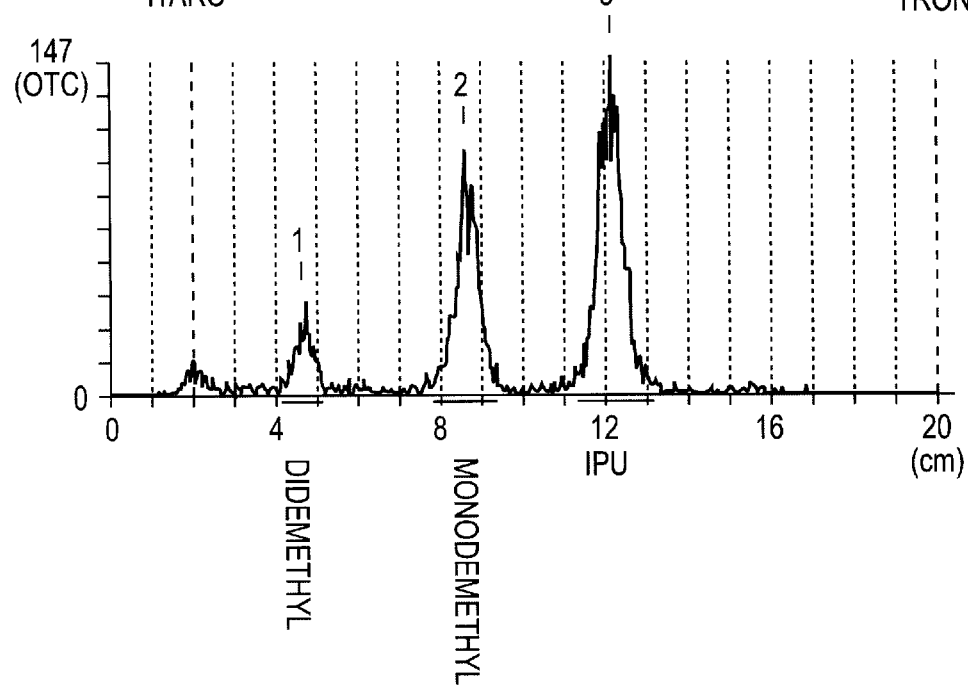

FIG. 9: Metabolism of isoproturon by CYP76B1 expressed in the yeast WAT11 (overexpressing cytochrome P450 reductase ATR1 of *Arabidopsis thaliana*). Substrate concentration: 200 µM [phenyl-U-$^{14}$C]isoproturon (IPU). Incubation time: 20 minutes in the presence of NADPH. 10 µl of yeast microsomes for a 200-µl assay. Analysis of the metabolites by thin-layer chromatography (identification by analogy with cold standards) from:

A—Control yeast: transformed with the empty plasmid pYeDP60

B—Yeast transformed with the plasmid pYeDP60 containing the coding sequence of CYP76B1.

Figure 10:
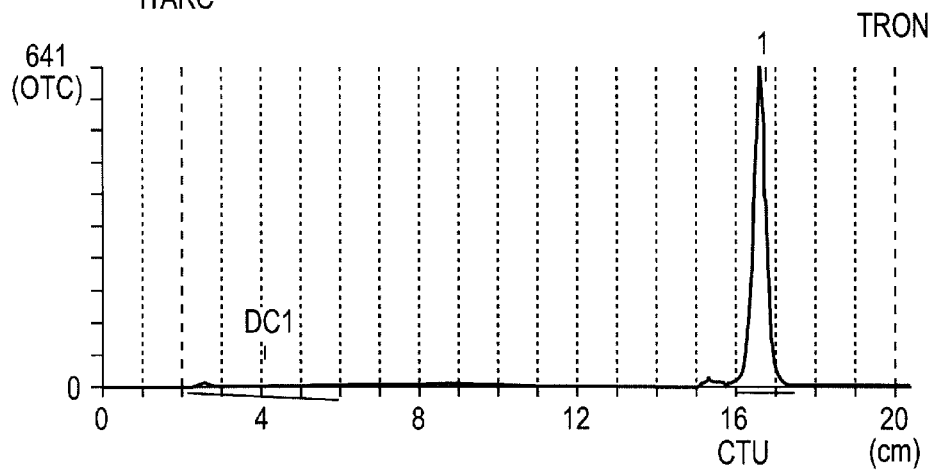
Figure 10:
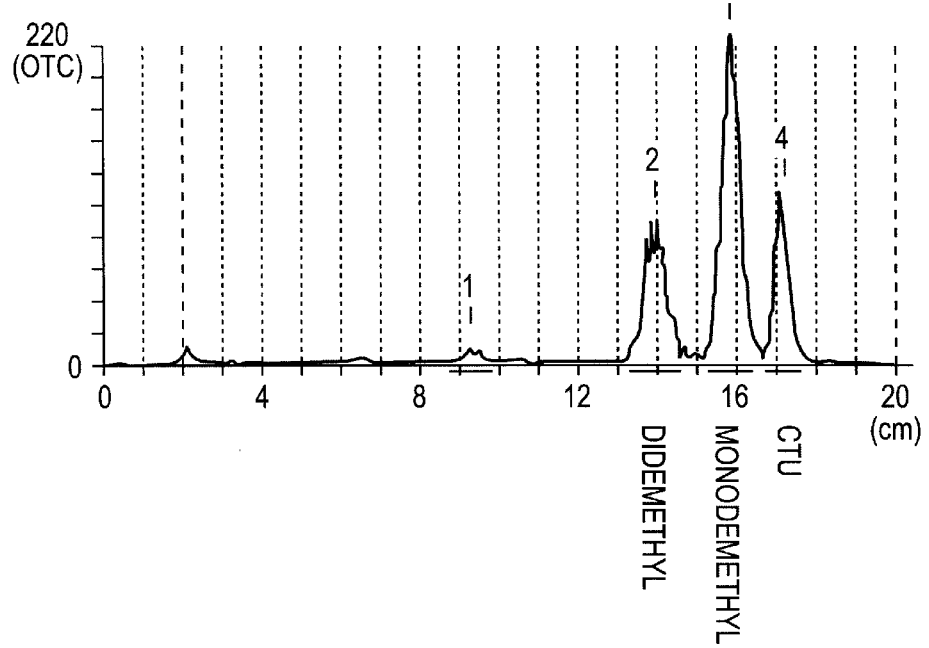

FIG. 10: Metabolism of chlortoluron by CYP76B1 expressed in the yeast WAT11 (overexpressing cytochrome P450 reductase ATR1 of *Arabidopsis thaliana*). Substrate concentration: 200 µM [phenyl-U-$^{14}$C]chlortoluron (CTU). Incubation time: 20 minutes in the presence of NADPH. 10 µl of yeast microsomes for a 200-µl assay. Analysis of the meabolites by thin-layer chromatography (identification by analogy with cold standards) from:

A—Control yeast: transformed with the empty plasmid pYeDP60

B—Yeast transformed with the plasmid pYeDP60 containing the coding sequence of CYP76B1.

Figure 11:
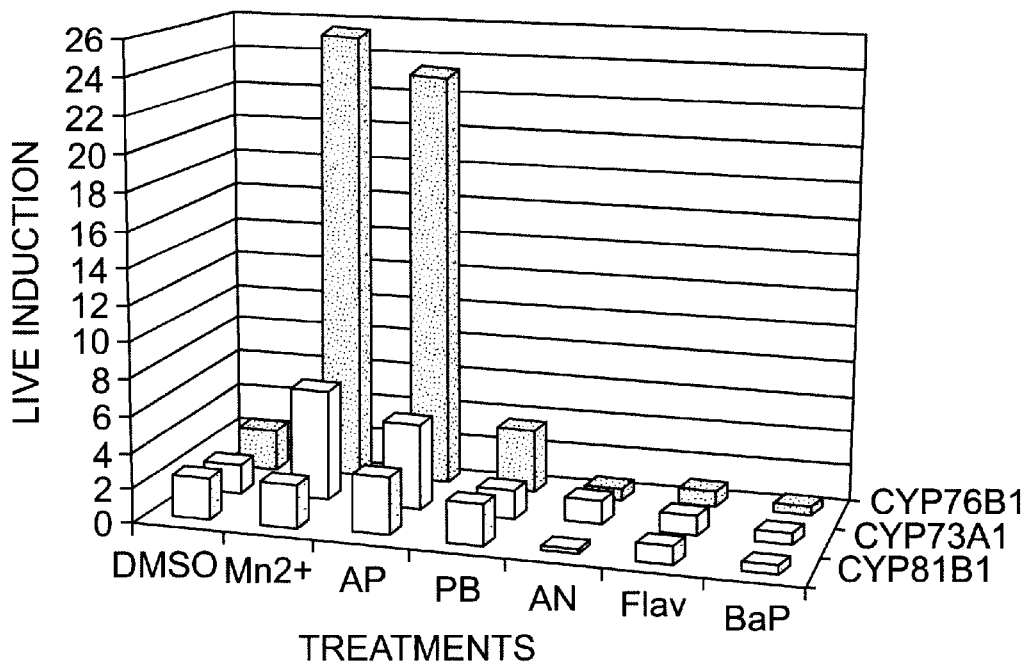

FIG. 11: Relative increase in steady state level of CYP76B1 CYP81B1 and CYP73A1 transcripts induced by xenobiotics. RNA were prepared from *H. tuberosus* tuber tissues, sliced and aged in water, or in solutions of different chemicals. The same RNA blot membrane (20 µg total RNA in each lane) was successively hybridized with CYP81B1, CYP73A1 and CYP76B1 $^{32}$P-radiolabeled probes. Hybridization signals were quantified with a phosphorimager. Induction is calculated by comparison to the signal recorded with RNA from tissues aged in water. Induction obtained with Fla, NA and B(a)P, which were dissolved in DMSO was compared to that obtained for tissues treated with DMSO alone.

Figure 12:
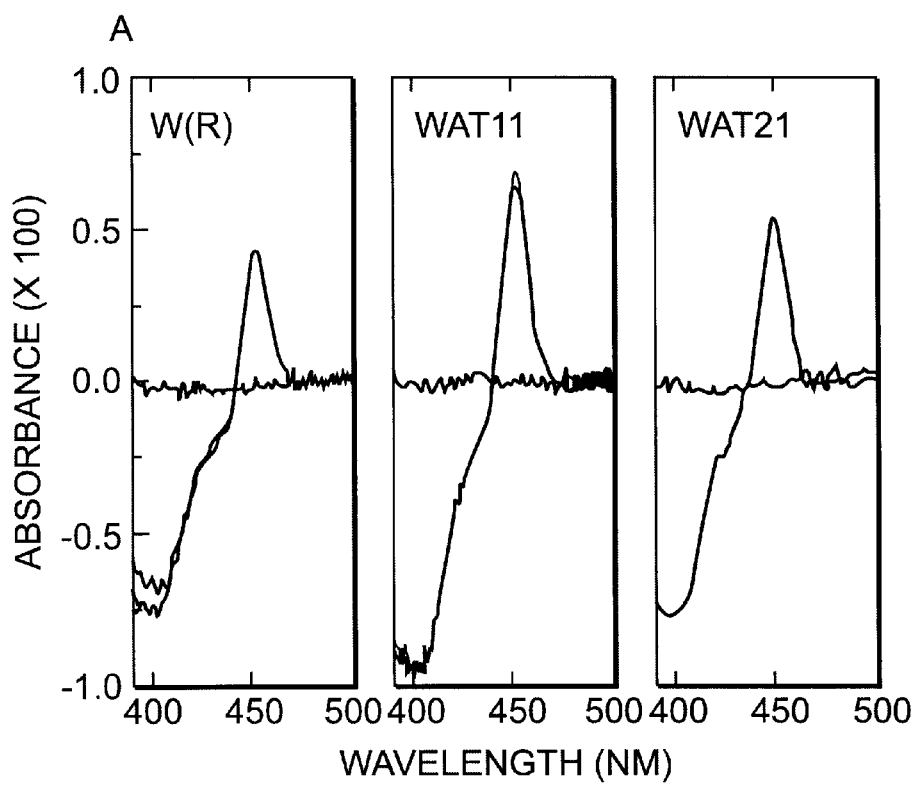

FIG. 12 Comparison of the expression of CYP76B1 in yeast strains coexpressing yeast (W(R)), *A. thaliana* ATR1 (WAT 11) or ATR2 (WAT21) reductases.

A. CO/reduced versus reduced difference spectra measured in microsomes of the three yeast strains after 16 hours of induction with galactose. Microsomal protein concentration in the cuvettes was 900 µg mL$^{-1}$. No P450 was detected in microsomes prepared from the same yeast strains transformed with a void plasmid.

B. Western blot analysis of the same microsomes.

M: molecular weight markers; HT: microsomes from *H. tuberosus* tuber treated with aminopyrine; V: microsomes from yeast transformed with a void plasmid; 76: microsomes from yeasts transformed with CYP76B1. Each lane was loaded with 20 µg microsomal protein.

Figure 13:
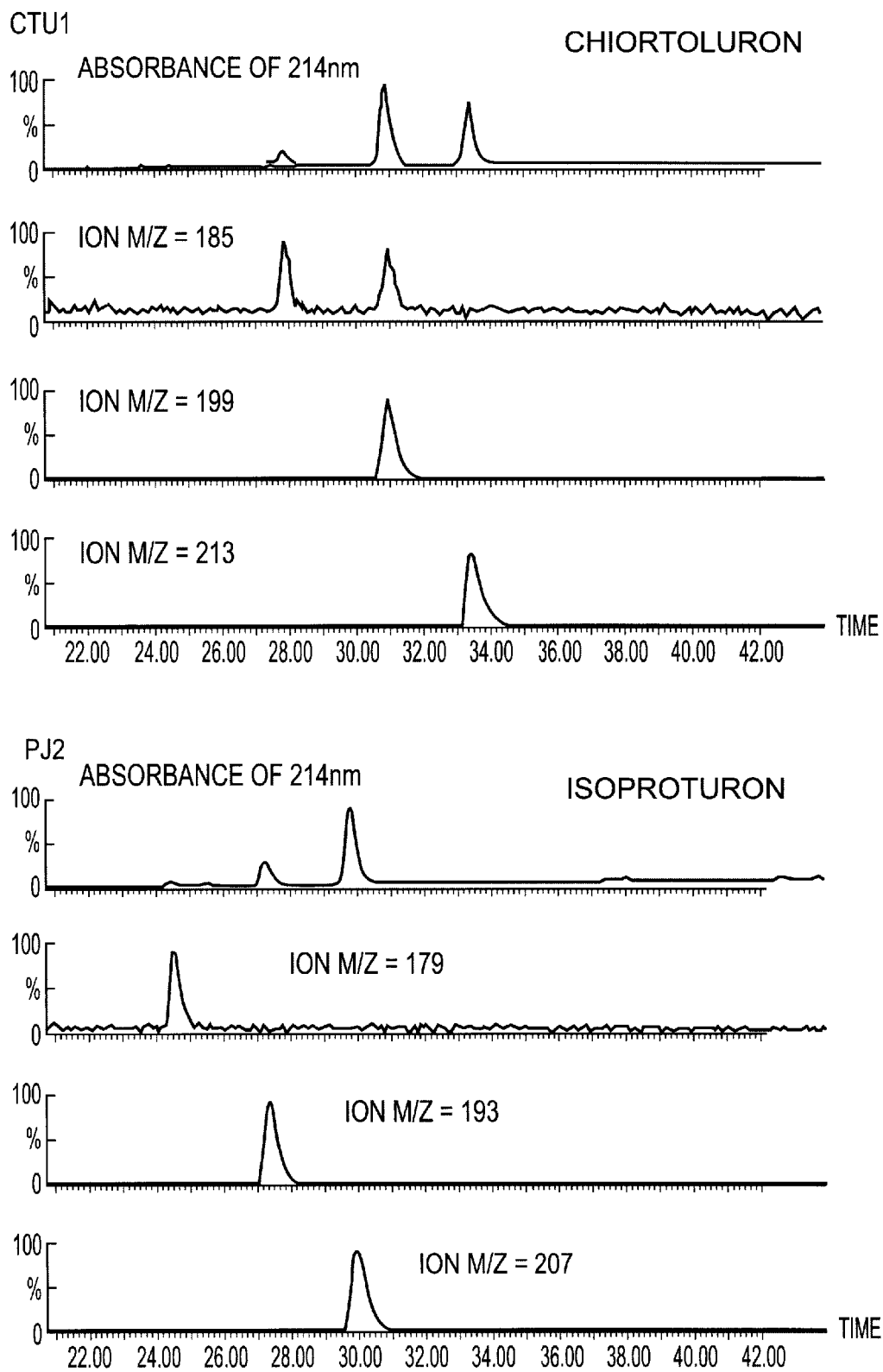

FIG. 13 : Products resulting from the CYP76B1-dependent metabolism of chlortoluron and isoproturon. Approximately 8 pmoles CYP76B1 in WAT11 yeast microsomes were incubated 60 min at 30° C. with 500 µM substrate, 500 µM NADPH, 1 mM glucose 6-phosphate and 0.5 units glucose 6-phosphate dehydrogenase in 200 µL 0.1 M sodium phosphate pH 7.4. Twenty µL of the acidified and centrifuged incubation medium were directly analyzed by LC-MS using a gradient of 3 to 60% B (100% acetonitrile, 0.08% TFA) in A (H$_2$O, 0.1% TFA) in 65 min. Absorbance was monitored at 214 nm.

Figure 14:
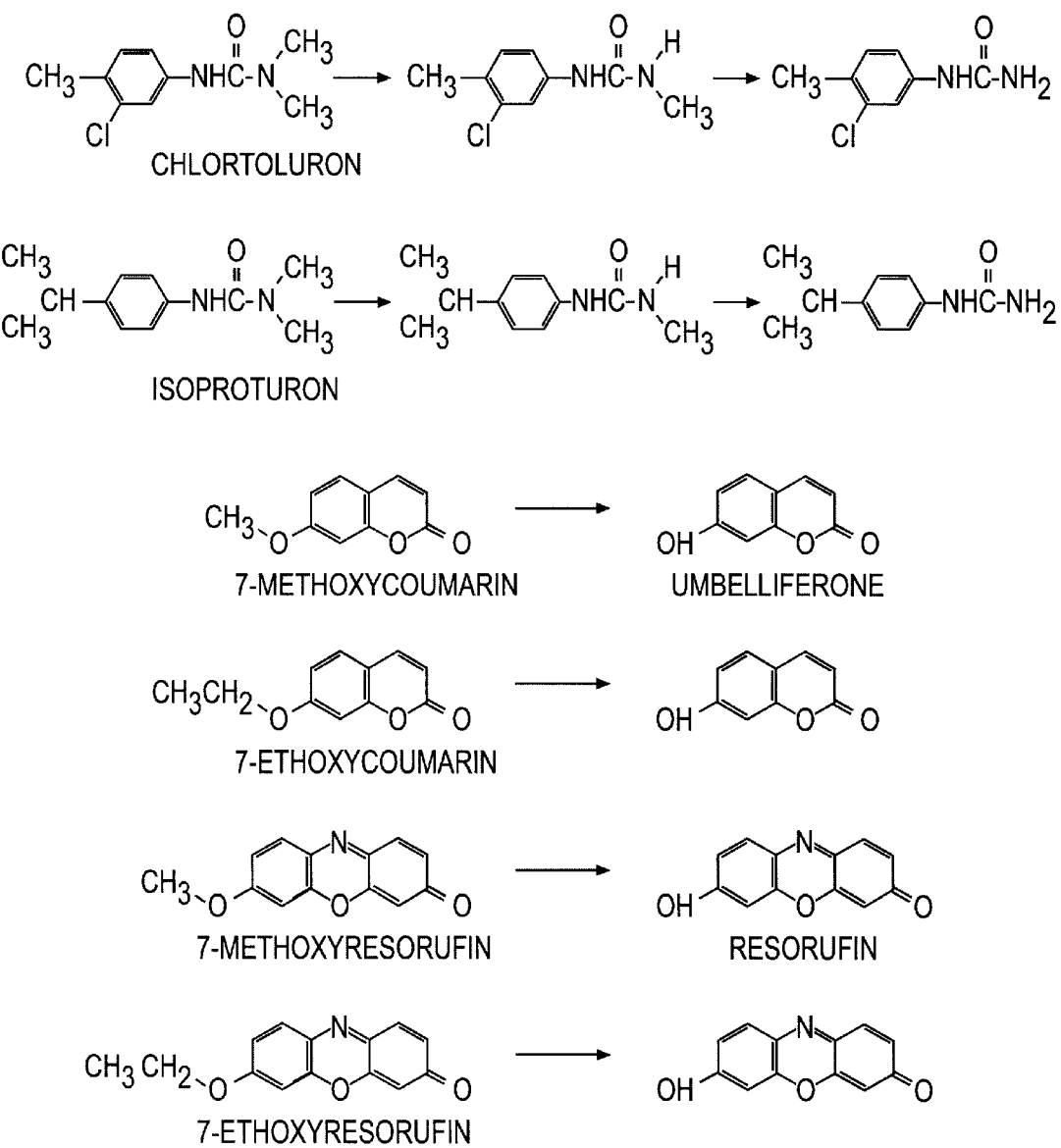

FIG. 14: Reactions catalyzed by CYP76B1.

Figure 15:
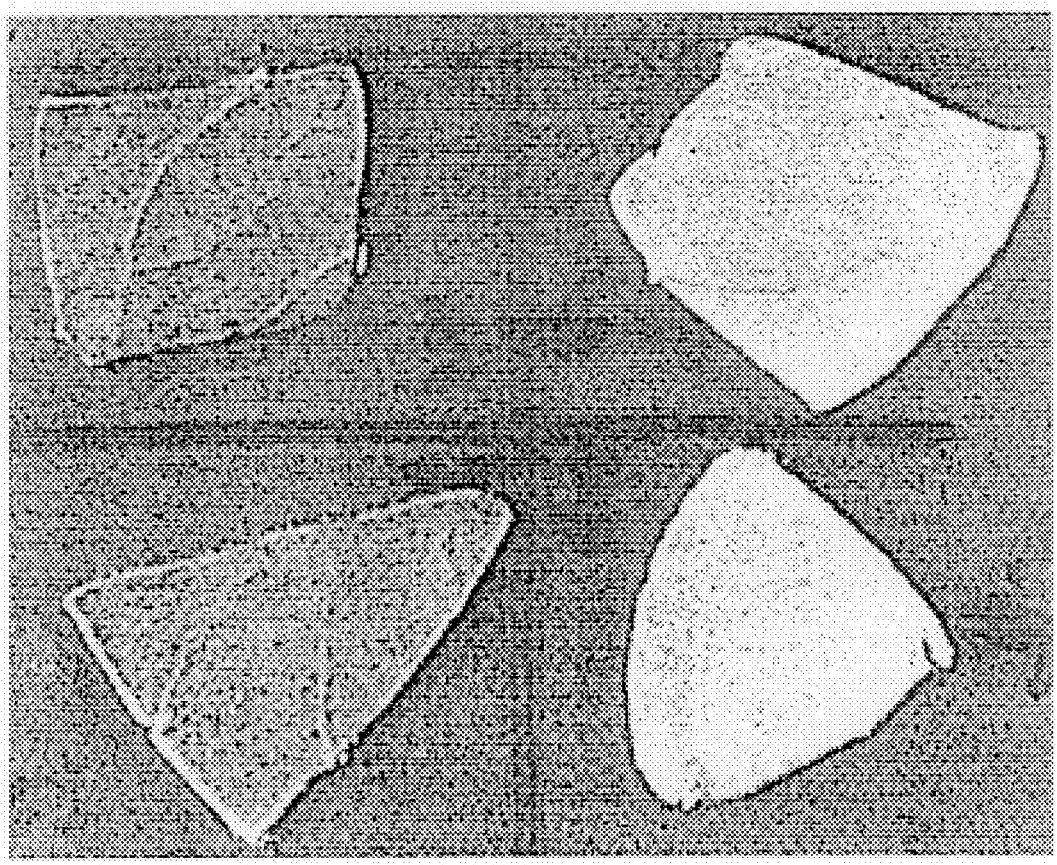

FIG. 15 : Leaf pieces from tobacco transformed with CYP76B1 (left) or with an empty plasmid (right) were aged for 10 days in Murashige and Skoog (MS) medium containing 0.5 µM linuron. CPYP76B1 expression in transgenic tobacco avoids chrorophyll destruction.

DETAILED DESCRIPTION OF THE INVENTION

Abbreviations

AP: aminopyrine; B(a)P: benzo(a)pyrene C4H: trans-cinnamate 4-hydroxylase [NADPH: oxygen oxidoreductase (4-hydroxylating), EC 1.14.13.11]; CTUDM: chlortoluton demethylase; DMSO: dimethylsulfoxide ECOD: 7-ethoxycoumarin O-deethylase; EROD: 7-ethoxyresorufin O-deethylase; Flav: flavone; IPUDM: isoproturon demethylase; MCOD: 7-methoxycoumarin O-deethylase; MROD: 7-methoxyresorufin O-deethylase NA: naphthalic anhydride, PB: phenobarbital.

Chemicals 1,8-Naphthalic anhydride was from Aldrich and phenobarbital (5-ethyl-5-phenyl-barbituric acid, sodium salt) from Fluka (St Quentin-Fallavier, France). Aminopyrine was from Merck (Darmstadt, Germany), benzoic acid, salicylic acid, coumarin, umbelliferone and 7-ethoxycoumarin were from Sigma (St Quentin-Fallavier, France). Other coumarin derivatives were gifts from Dr. J. L.

Riviére, Ecole Vétérinaire, Lyon, France. Resorufin derivatives were from Pierce.

Synthesis of [$^{14}$C]-ferulic acid, isoscopoietin and scopoletin was described by Cabello-Hurtado et al. (1998b). [3-$^{14}$C] trans-Cinnamic acid was from Isotopchim (Ganagobie, France), [1-$^{14}$C]lauric acid from CEA (Gif-sur-Yvette, France), [1-$^{14}$C]capric acid and [phenyl-U-$^{14}$C]2, 4dichlorophenoxyacetic acid were from Sigma. [7$^{14}$C]-Benzoic acid, [1-$^{14}$C]myristic acid, [1-$^{14}$C]palmitic acid, [1-$^{14}$C]stearic acid, [1-$^{14}$C]oleic acid and [1-$^{14}$C]linoleic acid were from DuPont (NEN-England). [$^{14}$C]Geraniol and [$^{14}$C]-S-naringenin were kindly provided by Dr. D. Hallahan (IACR-Roathamsted, UK) and Dr. G. Kochs (Institut für Biologie II, Freiburg, Germany), respectively. [dichlorophenyl-U-$^{14}$C]Diclofop was kindly provided by Hoechst (Frankfurt, Germany), [triazine-2-$^{14}$C] chlorsulfuron by Du Pont de Nemours (Wilmington, Del.), and [phenyl-U-$^{14}$C]bentazon by BASF (Ludwigshafen, Germany). [phenyl-U-$^{14}$C]Chlortoluron, [phenyl-U$^{14}$C] isoproturon, [triazine-U-$^{14}$C]simazine, as well as reference metabolites, were generous gifts from Novartis (Basel, Swizerland).

Plant Material

Jerusalem artichoke (*Helianthus tuberosus* L. var. Blanc commun) tubers were grown in open field, harvested in November and stored in plastic bags at 4° C. in the dark. For aging experiments, tubers were sliced (1.5 mm thick), washed and aged for 48 h in aerated (4 L.min$^{-1}$) distilled water containing various chemicals as described previously (13). The MnCl$_2$ solution was adjusted to pH 7. Water-insoluble compounds (β-naphthoflavone, naphthalic anhydride and benzo(a)pyrene) were first dissolved in 4 mL of dimethylsulfoxyde (DMSO) and then added to the aging medium (1.5 L). A control was performed with DMSO alone.

RNA Isolation and RNA Blot Hybridization

Total RNA was isolated as described by Lesot et al. (30). Denatured RNA was separated in the presence of formaldehyde through a 1.2% agarose gel and transferred onto a nylon membrane Hybond N$^+$, Amersham. RNA blots prehybridization and hybridization with a full-length CYP76B1 probe, radiolabeled with 50 µCi [α-$^{32}$P]dCTP by random priming, were carried out at 65° C. according to established procedures (31). Membranes were washed twice for 10 min with 2×SSC, 0.1% SDS and once for 10 min with 0.2×SSC, 0.1% SDS at room temperature, then twice for 30 min with 0.2×SSC, 0.1% SDS at 55° C. Hybridization signal was recorded by autoradiography and transcripts were quantified using a phosphorimager (Fuji BAS1000). RNA amounts were standardized by hybridization at 55° C. to a 300 pb *Capiscum annuum* 25S rRNA probe. The same membrane was successively hybridized with the CYP81 B1 (46% GC), CYP73A1 (47% GC), CYP76B1 (43% GC), again CYP81 B1, and 25S rRNA probes (45×10$^6$ cpm in each case). It was stripped by boiling in 0.1% SSC between successive hybridizations. Slot blot analysis was performed in the same conditions using 10 µg total RNA in each slot.

cDNA Library and Screening

Poly(A)$^+$RNA were prepared from *H. tuberosus* tuber tissues sliced and aged 24 h in the presence of 20 mM aminopyrine (30). A cDNA library was constructed in the vector λ-ZAPII (Stratagene), starting from 5 µg polyadenylated RNA, according to the manufacturer's instructions. Degenerate primers were designed (FIG. 1) from peptides isolated of a partially purified P450 fraction with ECOD activity (1). PCR was performed using 4 μL of amplified library (6×10⁷ pfu) as a template, 600 pmol of the degenerate primers and 20 pmol of a vector specific primer. The reaction mixture, containing 300 μM of each dNTP in reaction buffer (Tris-HCI 100 μM pH 8.3, KCI 110 μM, MgCl$_2$ 16 μM), was heated 2 minutes at 94° C. before addition of 0.1 unit of Taq DNA polymerase (Goldstar). After 3 min at 94° C., 30 cycles of amplification were carried out as follows: 1 min denaturation at 94° C., 1.5 min annealing at 53° C., 2.3 min extension at 72° C. The reaction was completed by 10 min extension at 72° C.

The 1.3 kb fragment amplified was electroeluted (31), cloned in a pGEM-T vector (Promega) according to the manufacturer's instructions, sequenced and characterized as a P450 fragment. It was then used as probe to screen approximately 2×10⁵ plaques from the aminopyrine-induced tuber cDNA library. Radiolabeling, prehybridization and hybridization were carried out as described for RNA blots. The insert length of 21 of the 95 positive clones was determined by PCR performed directly on the phage suspension using 20 pmoles of the SK and T7 vector-specific primers. Four clones were selected, purified by low-density screening, before rescuing pBluescript phagemids. Nucleotides missing at the 5'-end of the longest insert were obtained using the 5'-AmpliFINDER RACE kit from Clontech according to the manufacturer's instructions. The 5'-amplified fragment was digested by EcoRI and NheI, and subcloned in pBS containing the longest cDNA digested by the same enzymes.

Expression in Yeast

BamHI and EcoRI sites were introduced by PCR just upstream of the ATG and downstream of the stop codon of the CYP76B1 coding sequence, using the primers 5'-ATATATGGATCCATGGATTTTCTTATAATAGTGAGTAC (sense) 5'-TATATAGAATTCATGCTAGTTCAATGGTATTGGAACAACAC (reverse) (SEQ ID NO 3 and SEQ ID NO 4 respectively). The PCR mixture was preheated for 2 min at 92° C. before addition of 1 unit of Pfu DNA polymerase (Stratagene). After 3 min additional heating at 92° C., 30 cycles of amplification were carried out as follows 1 min denaturation at 92° C., 1 min annealing at 52° C., 2 min extension at 72° C. The reaction was completed by 10 min extension at 72° C. After BamHI/EcoRI digestion, the 1470 bp coding sequence was inserted into the vector pYeDP60 (32). Transformation of *Saccharomyces cerevisiae* W(R), WAT11 and WAT21, and yeast growth were conducted according to Pompon et al. (32). Yeast microsomes were prepared as described in Pierrel et al. (33) with addition of 1% SAB, 2 mM β-mercaptoethanol, 10 mM sodium disulfite and 1 mM PMSF to the extraction buffer. When indicated, 0.5 mM δ-aminolevulinic acid methyl ester (Sigma) was added to the induction medium, or cells were stored at 4° C. for 24 h before preparation of the microsomes.

Production of Antibodies and Western Blot Analysis

CYP76B1 4-His-tagged at the C-terminus was generated by PCR-modification of its coding sequence using the reverse primer 5'-TATATAGAATTCATGCTAATGATGATGATGGTTCAATGGTATTGGAACAACAC (SEQ ID NO: 27) with sense primer and PCR conditions as above. The modified protein was expressed in yeast using the same procedure as for the wild type. Microsomes were solubilized in 2% Triton X-114 followed by phase-partitioning as described previously (Gabriac et al., 1991). The protein was purified on a Ni$^{2+}$-loaded HiTrap Chelating column (Pharmacia Biotech) using the procedure recommended by the manufacturer, with elution in sodium phosphate 50 mM pH 7.4 containing 0.5 M NaCl and 1 M imidazole. Polyclonal antibodies were raised in rabbits by successive injections of once 16 μg and 5 times 8 μg purified protein emulsified in Freund's complete and incomplete adjuvants, respectively, and used for western blot analysis as in (Werck-Reichhart et al, 1993).

Analytical Methods and Enzyme Assay

LC-MS was performed by coupling a HPLC system (140A Perkin Elmer, Applied Biosystems Division, Foster City, Calif.) on a VG BioQ triple quadrupole. The separation on a reversed phase column (Macherey-Nagel 300-5 C18 2×125 mm) was flow splitted via a stainless steel Tee with approximately ⅟₁₅ of column effluent being directed towards the mass spectrometer, the ¹⁴⁄₁₅ being directed towards UV detector (Waters 496). The mass spectra were obtained by scanning from m/z 300–1800 in 6 seconds with a cone voltage of 50V.

Spectrophotometric measurements of P450 content and substrate binding were performed as in (Gabriac et al., 1991) and SDS-PAGE was performed as in Gabriac et al. (34). Gels were stained with Coomassie Blue R-250. Alkoxycoumarins and alkoxyresorufins O-dealkylation was measured by fluorometry (Werck-Reichhart et al., 1990). The data are means ± S.D. of triplicates.

The conversion of other molecules was assayed by TLC or HPLC analysis of polar metabolites formed from radiolabeled compounds (Cabello-Hurtado et al., 1998a, b). NADPH-cytochrome c reductase was assayed according to (Benveniste et al., 1986). Kinetic data were fitted using the nonlinear regression program DNRPEASY (Duggleby, 1984).

Proteins were quantified using the BCA Protein Assay from Pierce or the Bio-Rad Protein Assay.

Sequence Analysis and Comparison

Double-stranded pBluescript subclones were sequenced using the prism Ready Reaction Dye Deoxy Terminator Cycle method of Applied Biosystems Inc. The sequence data were analyzed using the GCG Sequence Analysis Software Package version 8.1 (35). Sequences were first aligned using ClustalW (35), the alignment refined by hand and diplayed using SeqVu 1.0.1. (Garvan Institute, Sydney). Phylogenies were calculated using programs Protdist and Neighbor from the Phylip package (36). The tree was drawn using Treeview (37).

EXAMPLES

Example 1

Cloning of the CYP76B1 cDNA

Figure 1:
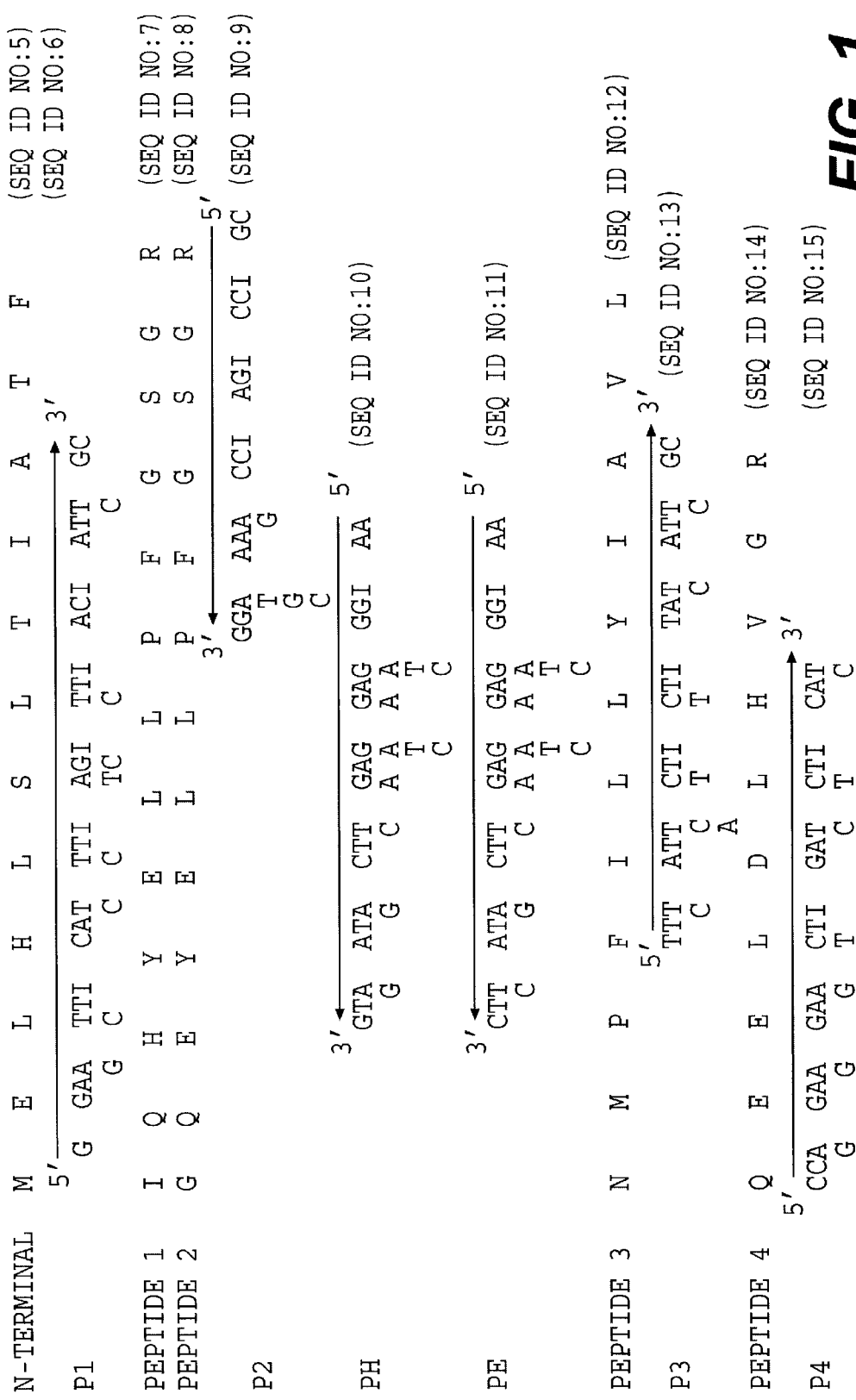
FIG. 1: Primers used for PCR amplification. An ECOD-enriched protein fraction was digested with trypsin and the resulting peptides were microsequenced. Some peptides, showing typical P450 features, were used to design sense or reverse primers for PCR amplification.

As previously reported (1), thirty peptides resulting from the trypsin digestion of an ECOD-enriched fraction isolated from Mn⁺⁺-induced *H. tuberosus* tuber tissues were microsequenced using the 473 A sequence analyzer of Applied Biosystem. Some of them clearly corresponded to P450 sequences: peptides 1 and 2, were different and both homologous to the heme-binding site; peptide 3, was homologous to a sequence located around residue 380 in enzymes of the animal CYP4 family; peptide 4, corresponded to a sequence located around residue 330 in enzymes of the plant CYP75 family (FIG. 1). Since these results suggested that our purified fraction was actually a mixture of different P450 isoforms, we decided to try the isolation of the corresponding cDNAs using a PCR approach.

Several degenerate primers were, therefore, designed (FIG. 1): i) three sense primers (P1, P3 and P4), corresponding to the N-terminus (which sequenced as a single peptide) and to peptides 3 and 4, ii) three reverse primers (P2, PH and PE) corresponding to the conserved and specific segments of peptides 1 and 2. A λ-ZAPII library of cDNA from aminopyrine-induced *H. tuberosus* tuber tissues was used as a template for the PCR experiments. Repeated attempts, using different annealing temperatures only led to amplification from primers P2 and SK under the conditions described in Material and Methods. The 1.3 kbp DNA fragment obtained was isolated and subcloned into a T-tailed vector. Sequencing showed that it coded for a typical P450 protein. Its hybridization on total RNA isolated from dormant tubers, wounded and aminopyrine-induced tissues, revealed a transcript of approximatly 1.6 kb, strongly expressed after aminopyrine treatment. To obtain a full-length cDNA, approximately $2 \times 10^5$ plaques of the cDNA library were then screened with this probe. Four clones of around 1.6 kb were selected and purified. They were all found to contain only partial coding sequences. Three of them were fully sequenced. Sequence analysis and alignment with other P450 sequences revealed that the longest of the inserts (2DD) was missing around 25 nucleotides. The missing 5'-sequence was obtained by 5'-RACE and a 1470 bp full-length cDNA reconstituted.

Figure 2:
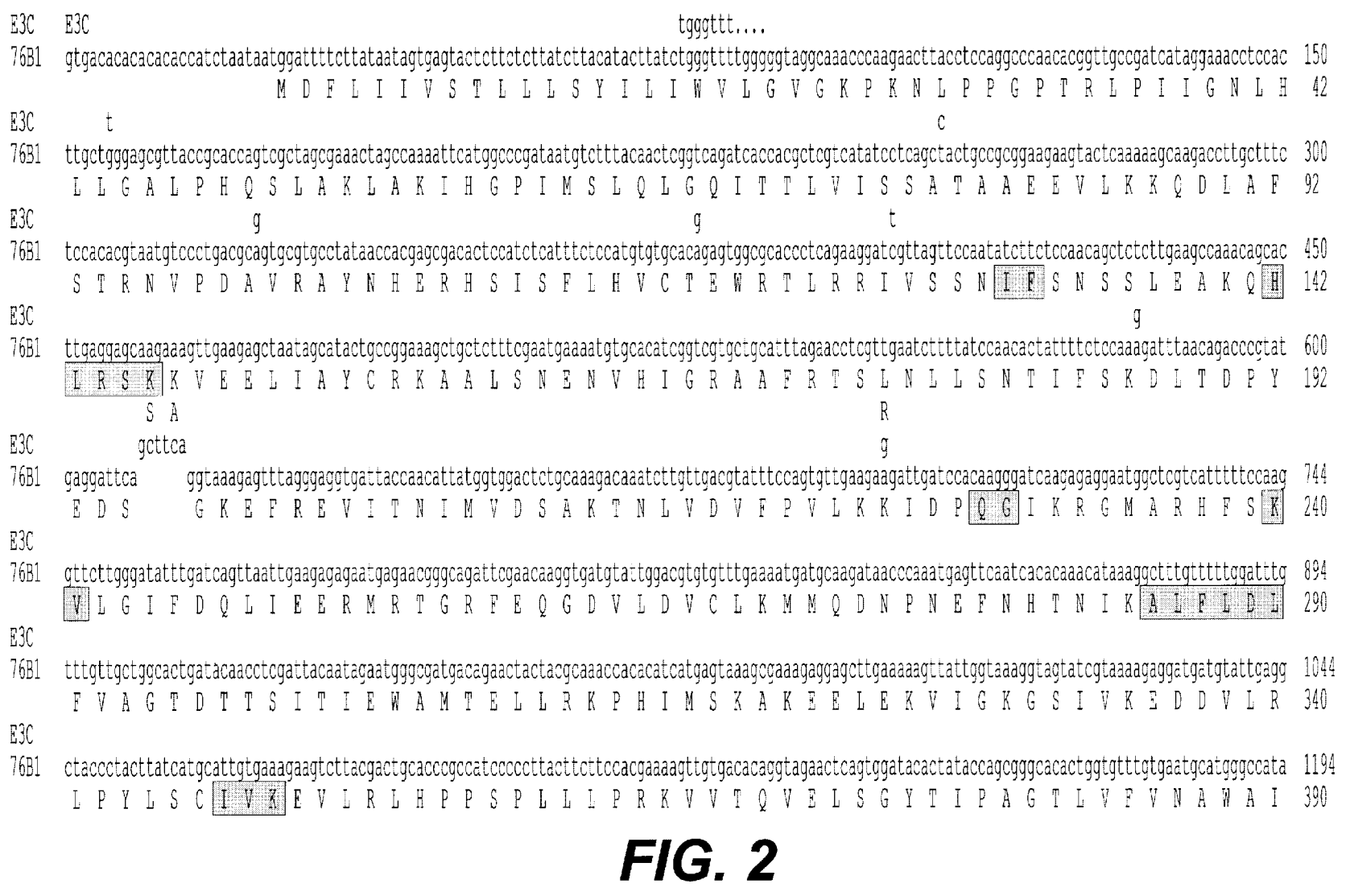

From the other inserts fully sequenced, one was found completely identical to 2DD, the other, E3C, differed from the 2DD clone by 7 conservative and one non-conservative replacements and by an insertion of two codons (FIG. 2). Minor differences were also observed in the 3' non-coding sequences. The overall nucleotide identity between the two cDNAs being higher than 98%, they very likely correspond to allelic variants.

Example 2

Characteristics of the CYP76B1 Protein

Figure 3:
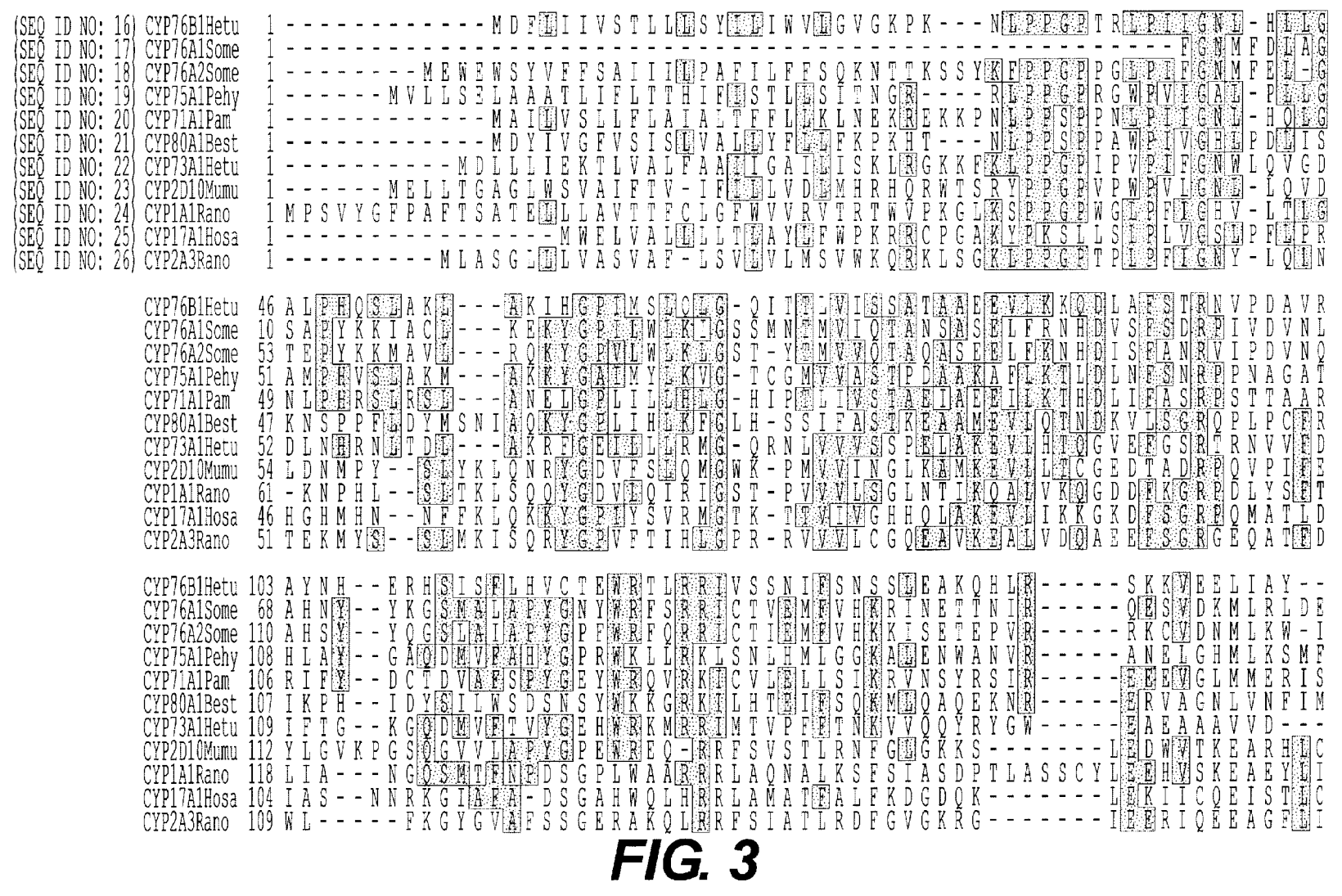
Figure 3:
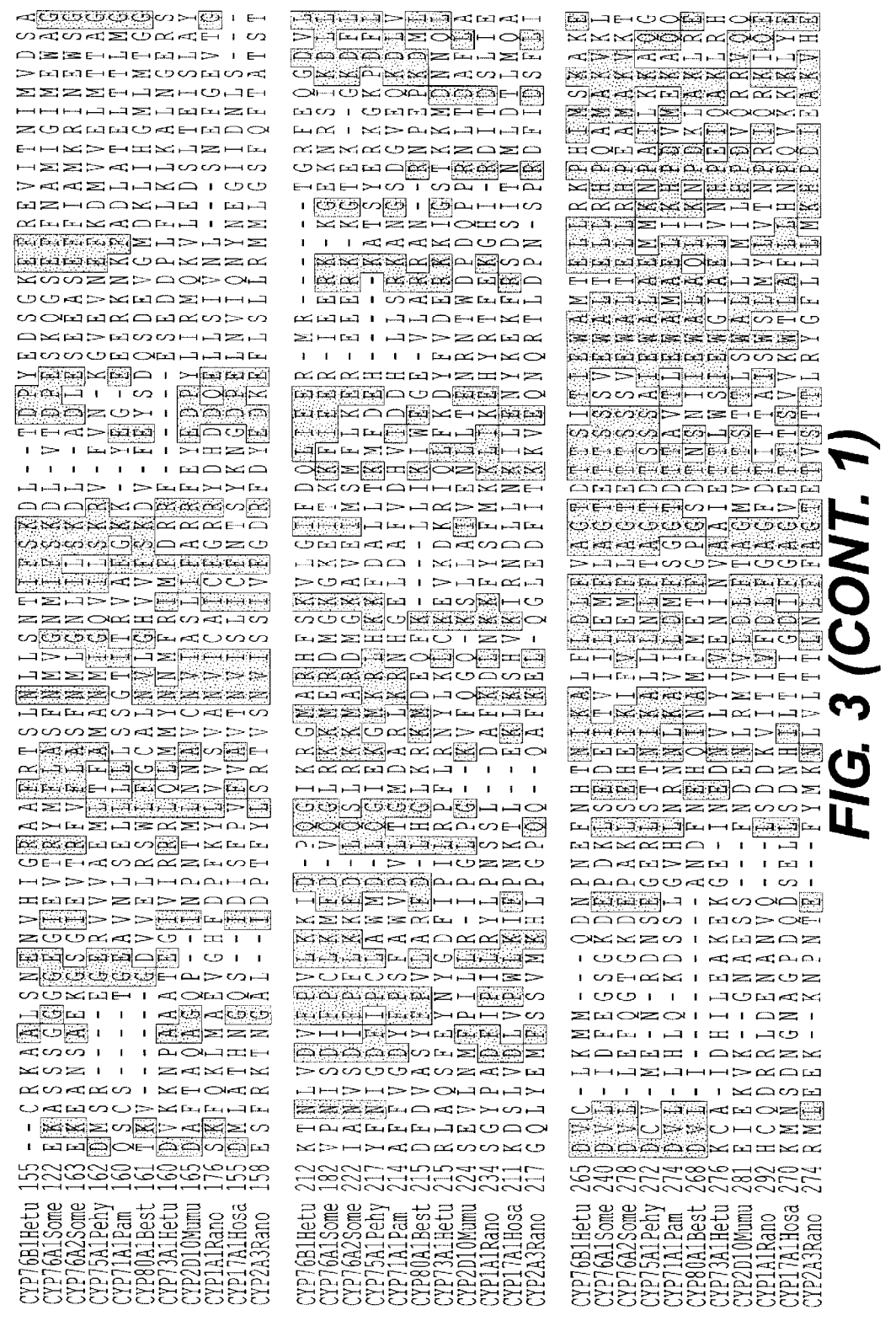
Figure 3:
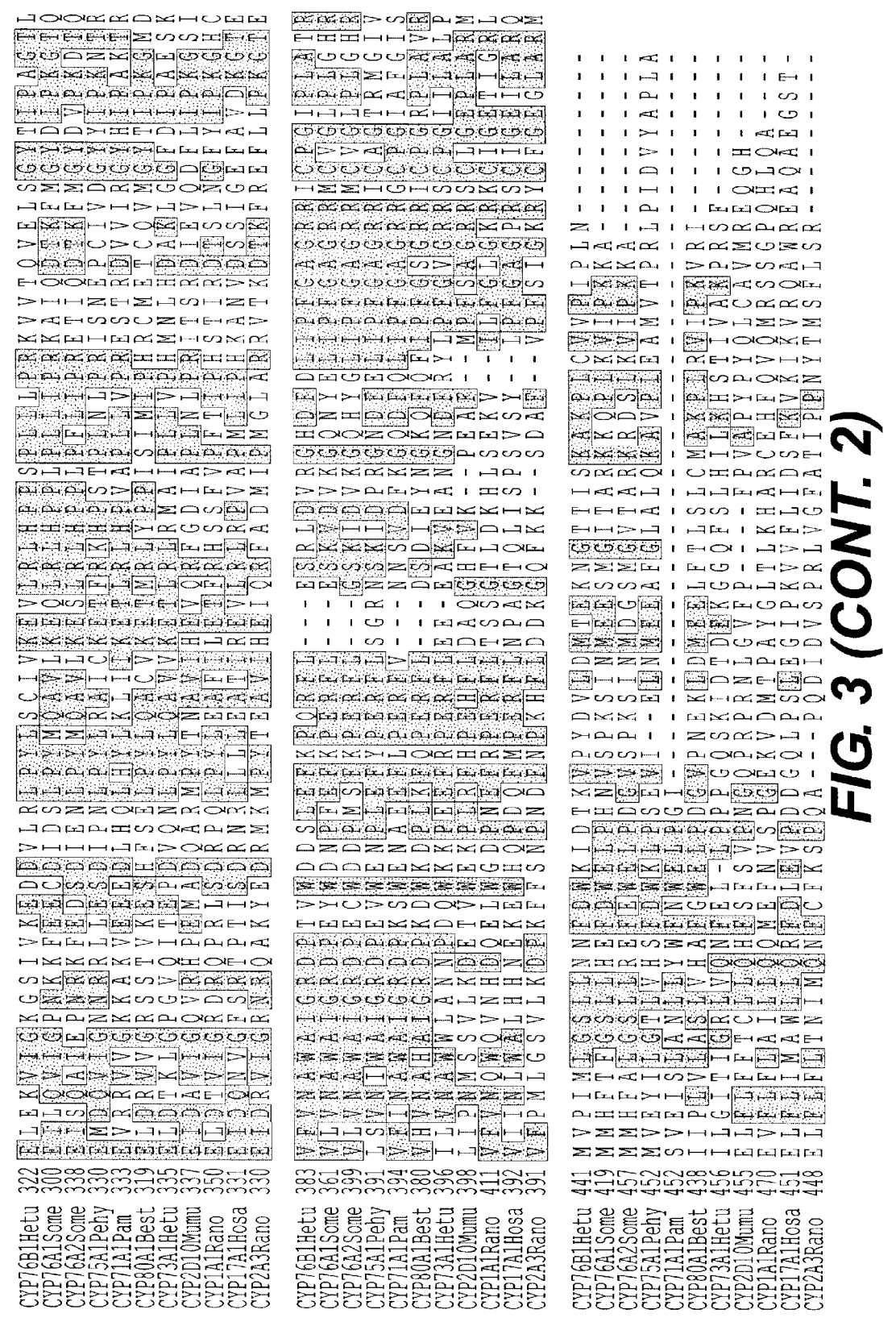

The full-length cDNA (SEQ ID NO 1) has non-coding sequences of 24 bp and 240 bp at the 5' and 3' ends, respectively, and codes a protein of 490 amino acids (SEQ ID NO 1) (FIG. 2), with an Mr of 54 956, and a relatively acidic pI of 6.06. Comparison to other P450 sequences reveals a high overall amino acid identity to the CYP71, CYP76 and CYP75 families (FIG. 3): 38.5% to the avocado CYP71A1, 38% to the *Solanum melanonga* CYP76A2, 37.9% to the *Petunia hybrida* CYP75A1 (a 3',5'-flavonoid hydroxylase). Highest identity (i.e. 41.1%) is observed with CYP76A1. Elongated 2DD was thus recorded as the first member of a new 76 subfamily and termed CYP76B1 by the P450 nomenclature committee (c/o Dr. D. R. Nelson, University of Tennessee, Memphis). CYP76B1 also shows high identity to the plant CYP80, involved in the biosynthesis of the alkaloid berbamunine (35.5%), CYP83 catalyzing the 5-hydroxylation of ferulic acid (34.6%) and CYP73 catalysing the 4-hydroxylation of cinnamic acid (30.1%). Most closely related animal P450s are steroids, drugs or coumarins metabolizing enzymes: CYP2D10 (28.8%), CYP1A1 with 7-ethoxycoumarin O-deethylase activity (28.8%), CYP2D3 (28.4%), CYP17A1 (27%), CYP2A3 with coumarin 7-hydroxylase activity (26.8%).

Figure 4:
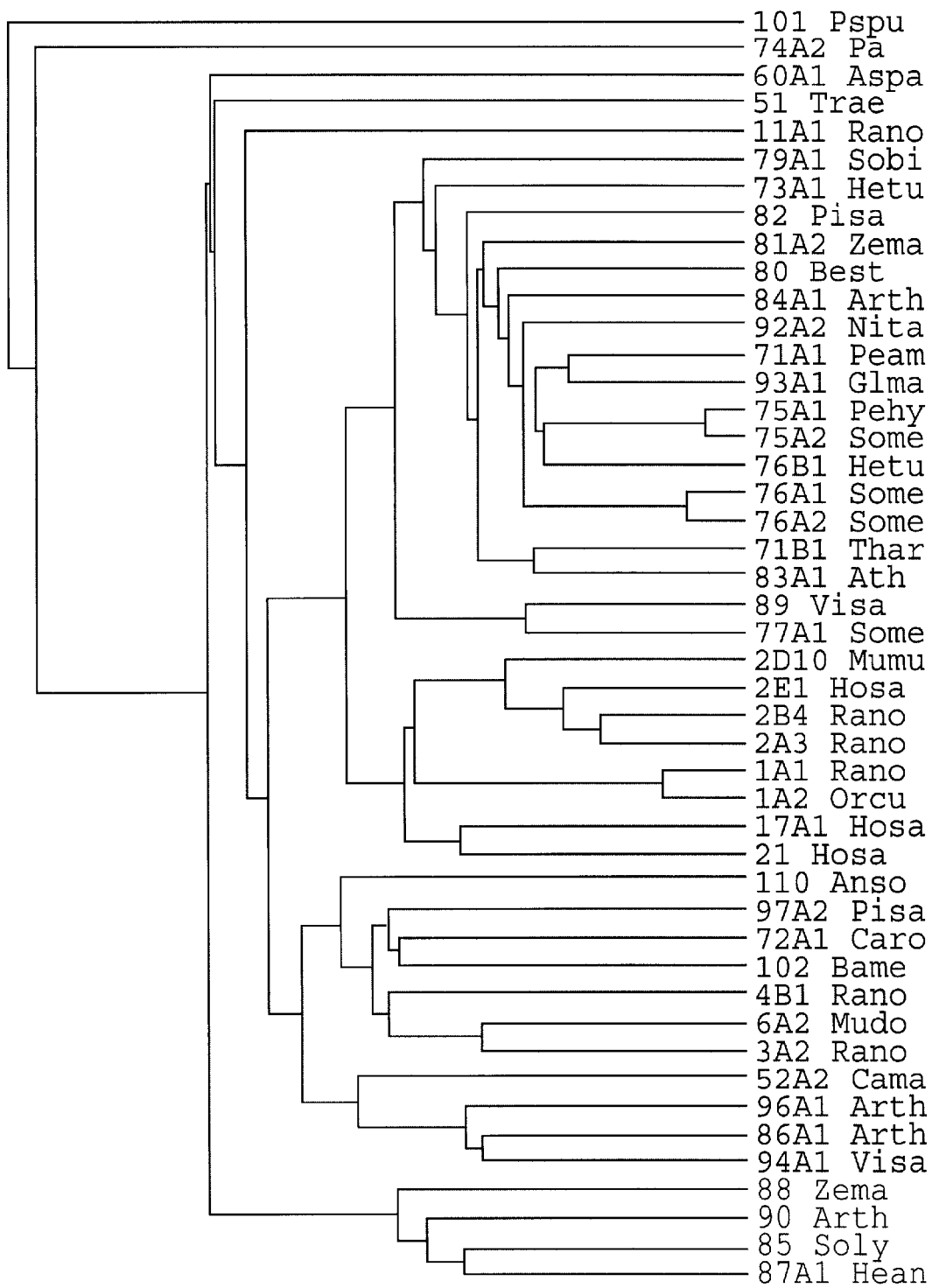
FIG. 4: Position of CYP76B1 in a phylogenic tree of the P450s superfamily. The tree shown here results from the alignment of the last 250 amino acids of each P450 protein, approx. from I helix to C-terminus.

CYP76A1 is missing around 40 amino acids at its N-terminus. N-terminus is the less conserved segment of the P450 proteins. Evaluation of the identity of CYP76B1 to CYP76A1 is thus slightly biased. CYP76B1 could actually be considered as the first member of a new plant P450 family, according to the criteria defined by Nelson et al. (38), its overall amino acid identity to any other full-length P450 being lower than 40%. Phylogenetic analysis provides different results, depending on whether the analysis is performed using different methods, with the whole sequence or using the most conserved 250 last amino acids. In most cases, it indicates (FIG. 4) that CYP76B1 is more closely related to CYP75 proteins than to CYP76A1 or A2, and also questions the classification of CYP76B1 in the CYP76 family. CYP76B1 is thus a good illustration of the difficulty of use the 40%–55% rule, although efficient in the case of animal enzymes, to delimit families and subfamillies in the case of plant P450s. The phylogram in FIG. 4 also shows that CYP76B1 shares common ancestors with CYP93, CYP71, CYP92, CYP84, CYP80, CYP81 and CYP83 enzymes, but is more distantly related to CYP73 and CYP79 proteins. CYP76B1 clearly belongs to the A group of plant P450s (39) deriving from a common ancestor and related to the main families of xenobiotic-detoxifying animal P450.

Example 3

Optimized Expression of CYP76B1 in Yeast

The CYP76B1 coding sequence was expressed in three engineered yeast strains, W(R), WAT11 and WAT21, which also expressed respectively yeast or *A. thaliana* P450 reductases ATR1 and ATR2 under the transcriptional control of the same galactose-inducible promoter GAL10-CYC1 (Urban et al., 1997). The levels of expression of CYP76B1 were compared in the different yeast strains after 12 h, 16 h, 24 h, and 36 h induction with galactose, or continuously grown in the presence of galactose. Highest expression was obtained using the WAT11 strain continuously grown in the presence of galactose, reaching 157 pmol $mg^{-1}$ microsomal protein (0.86% of microsomal protein). Contrary to CYP81 B1 (Cabello-Hurtado et al., 1998a), CYP76B1 was expressed at a significant level in the presence of yeast reductase, but its expression was consistently 15 to 40% lower in WAT21 or W(R) than in WAT11 (FIG. 12). Expression did not increase when δ-aminolevulinic acid was added to the growth medium, and significantly decreased when cells were grown at 25° C. or stored for 24 h at 4° C. before extraction.

Example 4

Accumulation of the CYP76B1 Transcripts in Xenobiotics-Treated Plant Tissues

Figure 5:
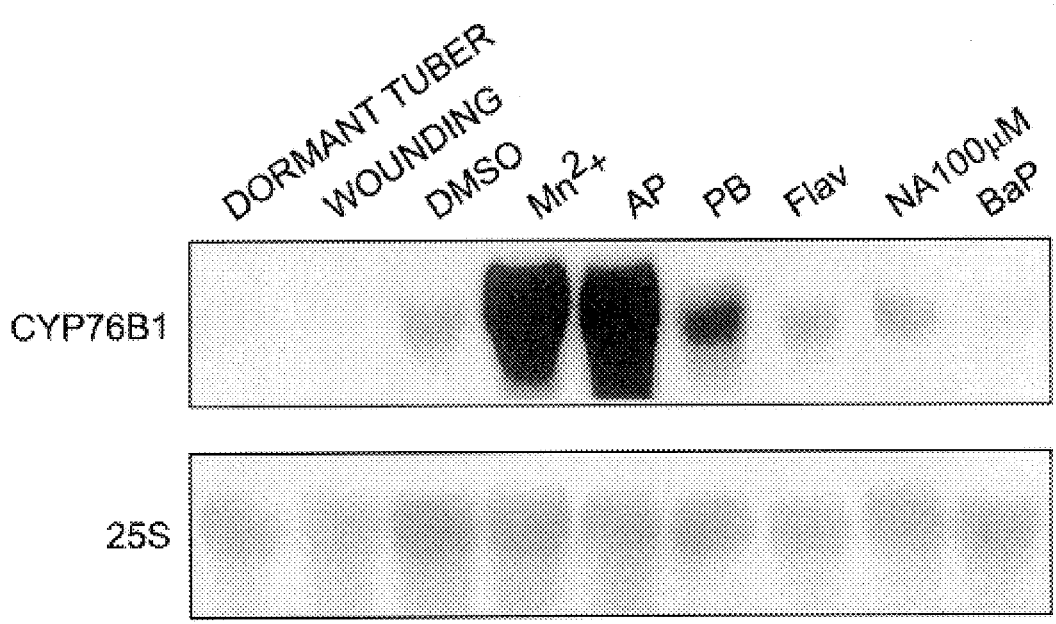
FIG. 5: Steady-state level of the CYP76B1 transcripts in *H. tuberosus* tuber tissues wounded and treated with xenobiotics. 20 µg of total RNA extracted from tubers, dormant, or aged 48 h in water ($H_2O$) or in solutions of chemicals (0.25% (v/v) DMSO, 25 mM $MnCl_2$, 20 mM aminopyrine (AP), 8 mM phenobarbital (PB), 1.7 mM flavone (Flav), 100 µM naphthalic anhydride (NA), or 260 µM benzo(a)pyrene (BaP) were analysed in a denaturing formaldehyde gel and transferred by capillary action onto nylon membrane. The RNA blot was successively hybridized with a full-length CYP76B1 DNA probe at high stringency, and with a 300 bp pepper probe coding for a 25S rRNA at low stringency as described in Material and Methods.

The steady-state level of the CYP76B1 transcripts in the *H. tuberosus* tuber dormant, wounded or treated with different chemicals was compared by RNA blot hybridization (FIG. 5). CYP76B1 mRNA were not detected in dormant tubers. Very low levels were found in wounded tissues. High levels of CYP76B1 transcripts, however, accumulated when the tuber tissues were incubated in the presence of xenobiotics: DMSO (3×the level detected in the control), phenobarbital (×6), manganese (×37) or aminopyrine (×44). By contrast, treatment with planar aromatic molecules, including benzo(a)pyrene, flavone and naphthalic anhydride, did not seem to affect or slightly reduce CYP76B1 mRNA accumulation.

CYP76B1 Induction by Xenobiotics Compared to Other P450s

Two other P450 cDNAs have been also isolated from *H. tuberosus*, a cinnamate 4-hydroxylase CYP73A1 (Teutsch et al., 1993) and a fatty acid in-chain hydroxylase CYP81B1 (Cabello-Hurtado et al., 1998 a). Increased accumulation of all three P450 mRNAs was detected following treatment of tuber tissues with xenobiotics. However, successive hybridizations of CYP76B1, CYP73A1, and CYP81B1 probes with the same RNA gel blot prepared with tuber tissues treated with different chemicals (DMSO, MnCl$_2$, AP, PB, Fla, NA, and B(a)P) indicated that by far the highest increase in steady state level of P450 transcripts was achieved in the case of CYP76B1 (FIG. 11). Similar results were obtained by parallel slot-blot hybridization analysis of the same set of total RNA. Tuber tissues treated with chemicals, in particular Mn$^2$+ and AP accumulated 2 to 6 fold more transcripts coding for CYP76B1 than for CYP73A1 or CYP81B1.

Example 5

CYP76B1 Codes for a P450 with O-dealkylase and N-dealkylase Activities

CYP76B1 Expression in Yeast

Figure 6:
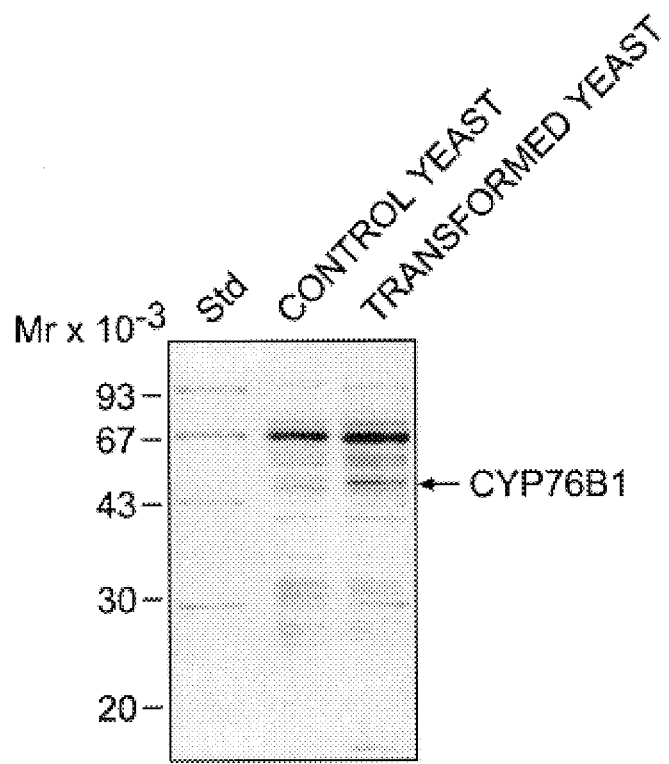
FIG. 6: SDS-PAGE analysis of the microsomes of yeast W(R) transformed with the CYP76B1/pYeDP60 construct and void pYeDP60. Microsomes were prepared from yeast continuously grown in the presence of galactose. Each lane contains 10 µg of microsomal protein.
Figure 7:
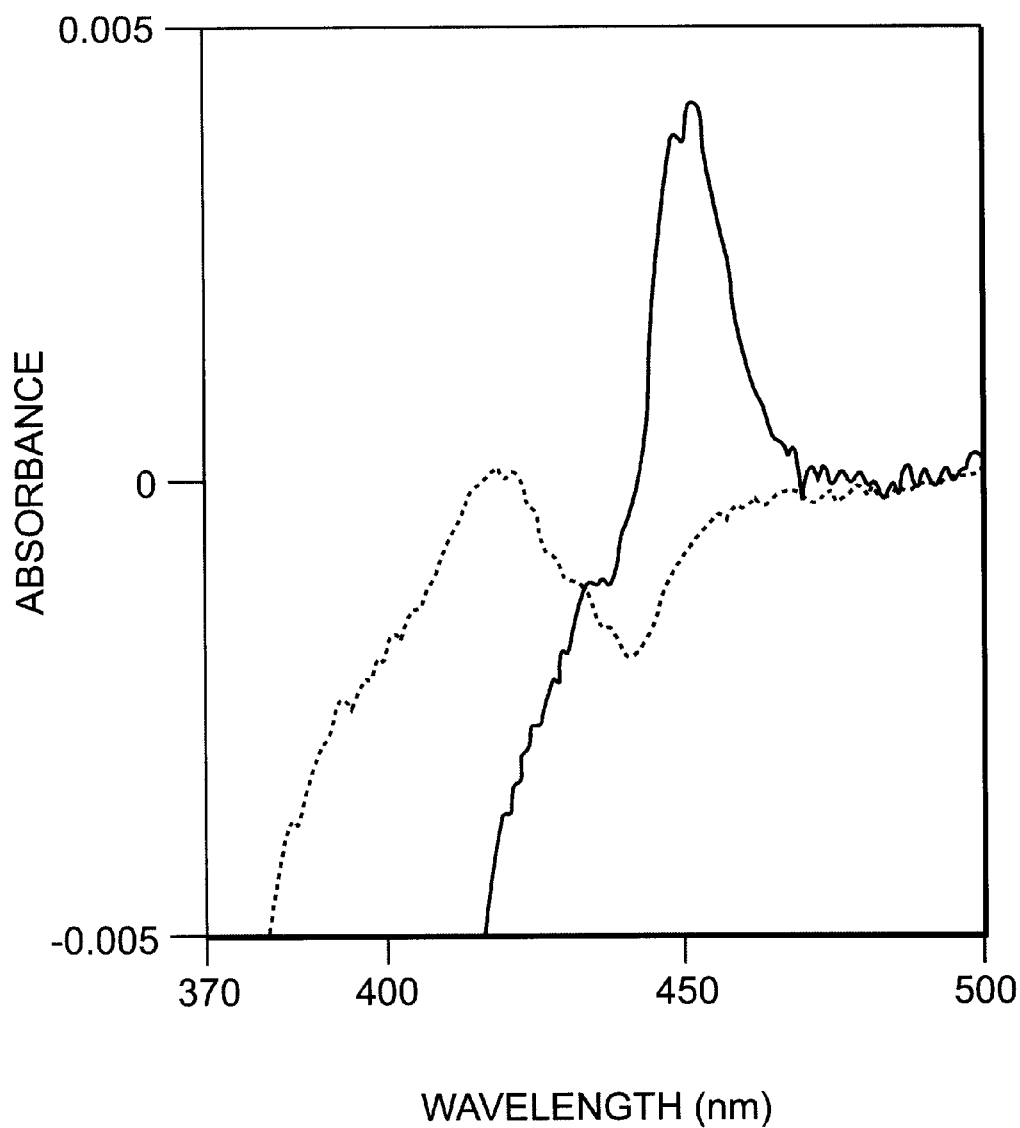
FIG. 7: Difference spectra induced by addition of carbon monoxide to reduced yeast microsomes. Spectra were recorded with 0.75 mg/mL microsomal protein in Tris-HCl 50 mM pH 7.5, containing 1 mM EDTA and 20% glycerol. A base-line was recorded after addition of an excess of sodium dithionite to both cuvettes. The difference spectra were obtained after bubbling carbon monoxide for one minute in the sample cuvette. Dotted line: control yeast microsomes. Solid line: CYP76B1-expressing yeast microsomes.

The CYP76B1 coding sequence devoid of its non coding sequences was inserted into the pYeDP60 shuttle vector and expressed in the engineered yeast strains W(R) and WAT11, overexpressing respectively yeast or *A. thaliana* reductases, to determine its catalytic activity. Using this plasmid and yeast strains, the expression of both P450 and yeast P450-reductases are under the control of the same galactose-inducible GAL10-CYC1 promoter (32). Yeasts transformed with the void pYeDP60 plasmid construct were used as control. In microsomes of CYP76B1/pYeDP60 transformed yeasts continuously grown in the presence of galactose, an over-expressed protein of approximately 54 kDa was clearly detectable (FIG. 6). In W(R) spectrally detectable P450 content was about 70 pmoles.mg$^{-1}$ protein (FIG. 7). No P450 was detected in control yeast transformed with the void pYeDP60.

CYP76B1 ECOD Activity

Microsomes from the control and CYP76B1-expressing W(R) yeasts were tested for ECOD activity (Table 1). No activity was detected in the control. Microsomes of yeast expressing CYP76B1 actively catalyzed NADPH-dependent O-deethylation of the fluorescent substrate. The reaction proceeded with a K$_{m,app}$ of 74 mM and a V$_{max}$ of 600 pkat.pmole$^{-1}$ P450. The activity, however, was not inhibited by polyclonal antibodies raised against the ECOD-enriched fraction previously purified in the laboratory. In addition, no activity was observed in the presence of cumene hydroperoxide.

In contrast, microsomes from aminopyrine-treated tuber tissue were capable of cumene hydroperoxide-dependent 7-ethoxycoumarin dealkylation and their NADPH-dependent deethylase activity was inhibited about 50% by the anti-ECOD antibodies.

TABLE 1

| Microsomes | ECOD activity (pkat · mg$^{-1}$ protein) | | |
|---|---|---|---|
| | NADPH | NADPH + anti-ECOD antibodies (inhibition) | cumene hydroperoxide |
| Aminopyrine-induced tissues | 5.2 ± 0.1 | 2.6 ± 0.1 (50%) | 2.5 ± 0.09 |
| Control yeast | n.d. | — | n.d. |
| Transformed yeast | 8.4 ± 0.05 | 7.5 ± 0.2 (10.7%) | n.d. |

Table 1: NADPH- and cumene hydroperoxide-dependent ECOD activity in microsomes from aminopyrine-induced *H. tuberosus* tuber tissues and in microsomes from control and CYP76B1-transformed yeast. Immunoinhibition by anti-ECOD antibodies.

Fluormetric assays contained 400 µM 7-ethoxycoumarin and were performed with 50 µM NADPH or 125 µM cumene hydroperoxide as electron donor. 10 µL of non-immune serum or of serum raised against purified ECOD fraction were preincubated 2 min at room temperature with 10 µL of microsomes before addition of the reaction mix. n.d.: not detectable.

Other CYP76B1 O-dealkylase Activities

The O-dealkylation of various other substrates of exogenous origin has also been performed with the microsomes prepared from W(R) and WAT11 transformed yeast strains. The turnover of the dealkylation are:

methoxycoumarin: 13 min$^{-1}$ (W(R)) and 31 min$^{31\ 1}$ (WAT11)

ethoxycoumarin: 10 min$^{-1}$ (W(R)) and 30 min$^{-1}$ (WAT11)

methoxyresorufin: 15 min$^{-1}$ (W(R)) and 41 min$^{31\ 1}$ (WAT11)

ethoxyresorufin: 6 min$^{-1}$ (W(R)) and 22 min$^{-1}$ (WAT11).

Example 6

Figure 8:
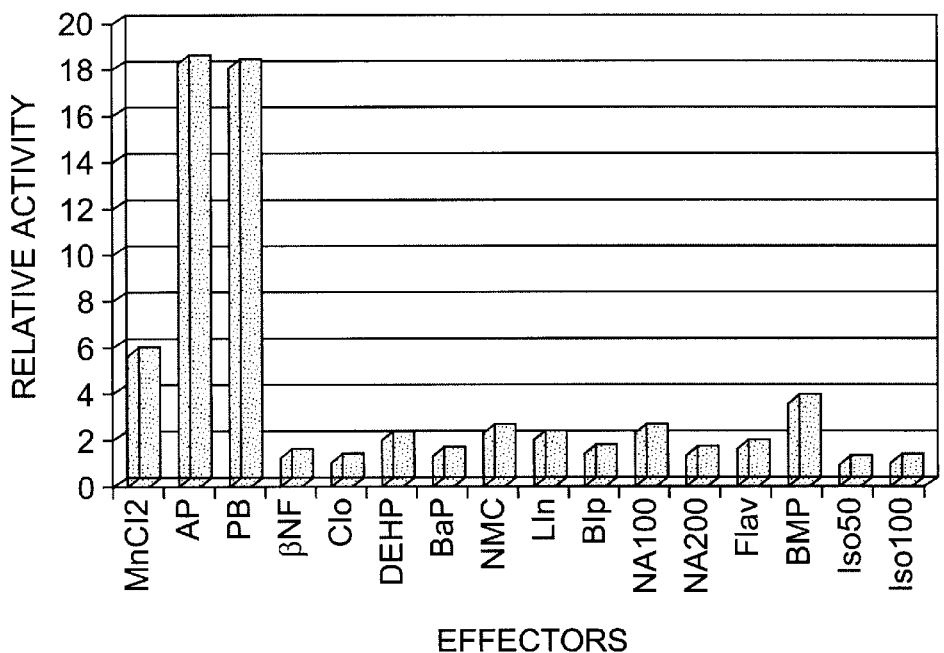
FIG. 8: Induction of the 7-methoxyresorufin O-demethylase activity by metals, pollutants and other exogenous organic molecules. Slices of dormant tuber of *Helianthus tuberosus* were placed under survival conditions in oxygenated distilled water and stirred with a current of compressed air in the presence of various metals or organic compounds (effectors). The dealkylase activity, expressed in relative activity, is measured in the microsomes prepared from these tissues after 48 hours of treatment (see Batard et al., 1995).

Induction of the MROD Activity by Metals, Pollutants and Other Exogenous Organic Molecules CYP76B1 very effectively catalyzes the O-dealkylation of 7-methoxyresorufin (see above). It has been shown in the laboratory that the 7-methoxyresorufin O-dealkylase activity is very strongly induced in the tuber of *H. tuberosus* brought into contact with metals (manganese, mercury) or with exogenous organic molecules (aminopyrine, phenobarbital, benzo(a)pyrene, 3-methylcholanthrene, lindane, 8-methoxypsoralen, diethylhexylphthalate, naphthalic anhydride and the like) (FIG. 8).

CYP76B1 N-dealkylase Activities

Mono- and didealkylation of herbicides of the phenylurea class by CYP76B1 expressed in W(R) and WAT11 yeast strains Mono- and didealkylation of isoproturon In the W(R) strain, the turnover of the first dealkylation of isoproturon is 40 min$^{-1}$. In the WAT11 strain, it is 147 min$^{31\ 1}$ (FIG. 9).

Mono- and didealkylation of chlortorulon

In the W(R) strain, the turnover of the first dealkylation of chlortorulon is about 376 min$^{-1}$. In the WAT11 strain, it is 803 min$^{-1}$ (FIG. 10).

No metabolism is detected in the yeasts transformed with the vector lacking the CYP76B1 sequence.

Example 7

Classes of Exogenous Molecules Metabolized by CYP76B1

Using transformed WAT11 yeast microsomes, we first assayed metabolism of endogenous molecules known or suspected to be substrates of P450 oxygenases from *H. tuberosus* tuber tissues: phenolics (cinnamate, benzoate, ferulate, naringenin, scopoletin, isoscopoletin), isoprenoids (geraniol, abcisic acid, obtusifoliol), and fatty acids (capric, lauric, myristic, palmitic, oleic, linoleic and linolenic acids). No metabolite of any of these molecules could be detected. We then tested different classes of foreign compounds, including molecules previously shown to be metabolized by the plant tuber microsomes (Higashi et al., 1981; Fonné, 1985; Fonné-Pfister et al., 1988 Werck-Reichhart et al., 1990; Batard et al., 1995): B(a)P and the drug aminopyrine, fluorescent alkoxycoumarins (7-methoxycoumarin, 7-propoxycoumarin, 7-butoxycoumarin) and alkoxyphenoxazones (7-methoxy-resorufin, 7-ethoxyresorufin, 7-pentoxyresorufin, and 7-benzyloxyresorufin), and representative members of different classes of herbicides (2,4-D, diclofop, chlorsulfuron, bentazon, dicamba, chlortoluron and isoproturon). In addition to 7-ethoxycoumarin, five xenobiotics were actively converted into more polar metabolites (Table 2). No metabolism was detected in the absence of NADPH or in control microsomes prepared from yeast transformed with a void plasmid.

TABLE 2

CYP76B1-dependent metabolism of xenobiotics.

| Strain | NADPH | Activity (pkat mg-1 protein) | | | | | |
|---|---|---|---|---|---|---|---|
| | | MCOD | ECOD | MROD | EROD | CT-UDM | IP-UDM |
| Control | + | n.d. | n.d. | n.d. | n.d. | n.d. | n.d. |
| W(R) | + | 10.9 ± 0.3 | 8.4 ± 1.5 | 12.6 ± 1.6 | 5.1 ± 0.2 | 1223 ± 63 | 128 ± 2 |
| WAT11 | + | 16.4 ± 0.4 | 15.9 ± 0.25 | 18.6 ± 0.6 | 11.6 ± 0.8 | 4258 ± 24 | 475 ± 3 |
| WAT11 | − | n.d. | n.d. | n.d. | n.d. | n.d. | n.d. |

Legend of Table 2

7-Methoxycoumarin-(MCOD), 7-ethoxycoumarin-(ECOD), 7-methoxyresorufin-(MROD) and 7-ethoxyresorufin-O-dealkylase (EROD) activities were determined fluorometrically using 16 pmol CYP76B1 per 2 mL assay. Demethylation of chlortoluron (CTUDM) and isoproturon (IPUDM) was tested using: $^{14}$C-labelled substrates with approximately 3 pmol CYP76B1 in the 200 µL assays. Conversion was estimated from the sum of the two polar metabolites detected after TLC analysis. Data are means + S.D. of two to four determinations. n.d.: not detected.

Example 8

Characterization of the Phenylurea Metabolites

Microsomes from AP-treated *H. tuberosus* tuber, when incubated with NADPH and chlortoluron, produce principally mono- and di-N-dealkylated metabolites and minor amounts of the ring-methyl hydroxylated compound (Fonné, 1985). It was unclear whether these different metabolites were generated by a single or several P450 enzymes. The products of CYP76B1-dependent metabolism of chlortoluron and isoproturon were thus extensively characterized. Both TLC and HPLC analysis of the metabolites, including co-chromatography with reference standards (not shown), suggested a sequential conversion of the herbicide to mono- and di-dealkylated derivatives. This was further confirmed by LC-MS analysis (FIG. 13). For both chlortoluron and isoproturon, time dependent and sequential formation of m/z −14 and −28 molecular ions was observed. To confirm the capacity of CYP76B1 to catalyze the double dealkylation of chlortoluron, the mono-demethylated derivative was purified by TLC from large scale incubations of transformed yeast microsomes with NADPH and $^{14}$C-chlortoluron. In the absence of chlortoluron, its mono-N-demethylated derivative was actively dealkylated by CYP76B1.

From fluorescence emission spectra of the products of alkoxycoumarins and alkoxyresorufins metabolism, with maxima at 460 (excitation at 380 nm) and 585 nm (ex: 530 nm) respectively, it was assumed that all compounds were O-dealkylated to form umbelliferone or 7-hydroxyresorufin.

Example 9

Catalytic Parameters of the CYP76B1-Dependent Reactions

Methoxy- and ethoxyresorufins were the best substrates of CYP76B1, with very high $k_{cat}/K_m$ of 237 and 165 min$^{-1}$ µM$^{-1}$, respectively in microsomes from the WAT11 yeast strain (Table 3). The next best substrate was chlortoluron, the first dealkylation proceeding significantly faster than the second. The first demethylation of isoproturon was slower than that of chlortoluron. 7-ethoxycoumarin and 7-methoxycoumarin turned out as the poorest substrates of CYP76B1. In terms of turnover number, phenylureas were the fastest metabolized substrates of CYP76B1 ($k_{cat}$ of 803 and 147 min$^{-1}$ for the first demethylation of chlortoluron and isoproturon, respectively), the second demethylation ($k_{cat}$= 46 min$^{-1}$ for monodemethyl-chlortoluron) being the rate limiting step for total detoxification of the herbicides.

TABLE 3

Catalytic parameters of the reactions catalyzed by CYP76B1 in the presence of different P450 reductases.

| Activity | Coexpressed reductase | $K_m$ (µM) | $K_{cat}$ (min$^{-1}$) | $K_{cat}/K_m$ (min$^{-1}$ µM$^{-1}$) |
|---|---|---|---|---|
| MCOD | yeast | 899 | 13 | 0.01 |
| | ATR1 | 808 | 31 | 0.04 |
| ECOD | yeast | 74 | 10 | 0.13 |
| | ATR1 | 60 | 30 | 0.5 |
| MROD | yeast | 0.23 | 15 | 64 |
| | ATR1 | 0.17 | 41 | 237 |
| EROD | yeast | 0.49 | 6 | 12 |
| | ATR1 | 0.17 | 28 | 165 |
| IPUDM | yeast | 361 | 40 | 0.11 |
| | ATR1 | 289 | 147 | 0.51 |
| CTUDM | yeast | 202 | 376 | 1.8 |
| | ATR1 | 179 | 803 | 4.5 |
| monodemethyl-CTU DM | ATR1 | 81 | 46 | 0.57 |

Legend of Table 3

CYP76B1 concentrations in the MCOD, ECOD, MROD and EROD fluorometric assays were 1.5 nM or 2.1 nM, depending on the coexpressed ATR1 or yeast reductases. In the CTUDM assays, CYP76B1 concentrations were 1.7 nM (ATR1) and 8 nM (yeast), respectively. It was 12 nM for the determination of the catalytic parameters of monodemethyl-CTUDM, and 1.7 nM (ATR1) or 20 nM (yeast) in the IPUDM assays. Products were quantified by direct TLC analysis of 100 µL of the acidified incubation medium after 6 min incubation at 30° C. for the CTUDM and IPUDM assays, and after 9 min incubation for the monodemethyl-CTUDM.

Example 10

Influence of the P450 Reductases on CYP76B1 Activity

Preliminary results (Table 2) having indicated that differences in catalytic activity were larger than difference in P450 expression in the three yeast strains, the catalytic parameters of xenobiotic metabolism were determined with CYP76B1 expressed in both W(R) and WAT11 microsomes (Table 2). The nature of the coexpressed reductase did not much influence the $K_m$ of the reactions, although $K_m$ values measured in the presence of the *A. thaliana* reductase ATR1 were consistently lower than those determined in the presence of yeast reductase. However, large changes in $k_{cat}$ were observed depending on the origin of the coexpressed reductase. The maximum velocities of oxygenation of all six substrates were about three times higher in the presence of ATR1. Catalytic parameters were also measured in the presence of the other *A. thaliana* reductase ATR2 with methoxyresorufin as substrate. They were not significantly different ($K_m$=0.185 µM; $k_{cat}$=43 min$^{-1}$) from those determined with microsomes from WAT11.

The observed variations in $k_{cat}$ could result from differences in reductase expression in W(R) and WAT yeast strains. We thus compared the velocities of NADPH-dependent cytochrome c reduction in microsomes from the three strains. The reductase activity in microsomes from 76B1W(R) (0.74±0.057 μmol min$^{-1}$ mg$^{-1}$) was higher than in microsomes from transformed WAT11 and WAT21 (0.61±0.023 and 0.60±0.01 μmol min$^{-1}$ mg$^{-1}$, respectively). Differences in $k_{cat}$ observed in our experiments are thus likely to result from faster electron transfer between plant enzymes, or from a plant reductase-induced change in CYP76B1 conformation or stability.

Example 11

Other Phenylurea Herbicides

Metabolism of both chlortoluron and isoproturon suggests that other herbicides of the class of phenylurea could be substrates as well, therefore we tested the binding of a set of related molecules in the active site of CYP76B1. The binding of substrates into the catalytic site of a P450 usually induces a shift of its maximum of absorbance, redox potential and iron spin state (Raag and Poulos, 1989) resulting from the displacement of the water sixth ligand of the heme iron. It is easily detected by differential spectrophotometry as a so-called type I spectrum with a peak at 390 nm and a trough at 420 nm (Jefcoate, 1978). The variation of the differential absorbance $\Delta A_{390-420}$ versus substrate concentration allows the calculation of an apparent dissociation constant ($K_s$). A high $\Delta A_{max}$ induced by the ligand is usually an indication of correct positioning for catalysis. Therefore, the high $\Delta A_{max}$ induced by the binding of the molecules in Table 4 suggests that a similar positioning of the dimethylurea function close to heme iron and favorable to catalysis is maintained for many phenylureas. Affinity for the active site seems to be largely governed by the substituents on the phenyl ring, the presence of ring-deactivating halogens being more favorable than methyl or other potentially activating substituents. Replacement of one of the N-methyls by a hydroxymethyl group also seems to favor the binding of the molecules in the active site of CYP76B1.

TABLE 4

Binding parameters of the spectra induced upon fixation of phenylureas in the active site of CYP76B1.

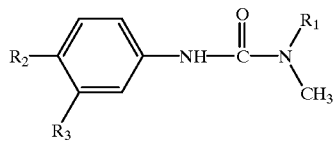

| Name | $R_1$ | $R_2$ | $R_3$ | $K_s$ (μM) | $\Delta A_{max} \times 10^{-3}$ |
|---|---|---|---|---|---|
| Monolinuron | —OCH$_3$ | —Cl | —H | 4.8 | 6.6 |
| Chlorbromuron | —OCH$_3$ | —Br | —Cl | 5.3 | 6.7 |
| Metobromuron | —OCH$_3$ | —Br | —H | 6.2 | 7.6 |
|  | —CH$_3$ | —Cl | —CH$_3$ | 14.5 | 5.4 |
| Diuron | —CH$_3$ | —Cl | —Cl | 20 | 4.8 |
| Chlortoluron | —CH$_3$ | —CH$_3$ | —Cl | 24 | 5.1 |
| Isoproturon | —CH$_3$ | —CH(CH$_3$)$_2$ | —H | 55 | 8.2 |
|  | —CH$_3$ | —CH$_3$ | —CH$_3$ | 60 | 6.6 |
| Metoxuron | —CH$_3$ | —OCH$_3$ | —H | 117 | 6.1 |

Legend of Table 4

CYP76B1 was 60 nM in the assays. Difference spectra were recorded after the addition of increasing concentrations of ligands to the sample cuvette. An equal volume of the herbicide solvent (DMSO) was added to the reference. $K_s$ and $\Delta A_{max}$ at saturating ligand concentration were calculated from the double-reciprocal plots of $\Delta A_{(390-420\ nm)}$ versus substrate concentrations.

Example 12

CYP76B1 Expression in Transgenic Tobacco Avoids Chlorophylls Destruction

The CYP76B1 cDNA was inserted in vector pBDX (Gachotte D., 1995). The resulting vector was mobilized into *Agrobacterium tumefaciens* strain LBA4404 by triparental mating (Ditta G. et al., 1980). Plant transformation was realized according to Horsch et al. (1985): tobacco leaf disks were soaked for 10 minutes in an Agrobacterium solution, blotted dry and placed on MS callus-inducing medium containing 500 μg/ml cefotaxime and 100 μg/ml kanamycin. After four to six weeks, shoots were transferred on MS-rooting medium containing 100 μg/ml cefotaxime and 100 μg/ml kanamycin. After rooting, plants were transferred in soil.

CYP76B1 is a new plant P450 that has been classified in the same family as CYP76A1 and CYP76A2 previously isolated from *Solanum melanonga* seedlings (40). No information is available concerning the possible function of these two eggplant P450s. CYP76B1 also shares relatively high sequence identity to CYP75s which are 3' and 5'-hydroxylases of the flavonoid B-ring, involved in the synthesis of anthocyanin (41). All enzymes most closely related the CYP76s belong to the A group of plant P450s, and are known or suspected to catalyze oxidation steps of plant secondary metabolism (39). CYP76B1 is thus likely to catalyze an oxygenation reaction in the synthesis of some pigment or defense related molecule. Expressed in yeast, CYP76B1 is able to catalyze the O-deethylation of the model fluorescent substrate 7-ethoxycoumarin. The reaction proceeds with a $V_{max}/K_m$ of 0.13, i. e. much more efficiently than when catalyzed by the *H. tuberosus* CYP73A1 or by the tobacco cTBP, which were previously shown to O-deethylate 7-ethoxycoumarin with a $V_{max}/K_m$ of 0.011 and 0.0023, respectively (29, 33). CYP76B1 is also an efficient catalyst compared to animal P450s reported to dealkylate 7-ethoxycoumarin like CYP1A1 ($V_{max}/K_m$ = 0.66), CYP1A2 (0.02) or CYP2E1 (0.03) (24). Most known substrates of all these 7-ethoxycoumarin metabolizing P450s are planar aromatic molecules. This may indicate that physiological or other good alternate substrates of CYP76B1 could be planar aromatic compounds. It would be further confirmed by the fact that all substrates of CYP76B1 identified so far are also planar aromatic molecules (FIG. 14). The high catalytic efficiency of 7-alkoxycoumarins and 7-alkoxyresorufins metabolisms compared to other animal and plant P450s also suggests that CYP76B1 has a less stringent substrate specificity than most plant enzymes, and is maybe a good metabolizer of exogenous molecules and a potential tool for bioremediation. CYP76B1-dependent metabolism of xenobiotics will, therefore, be further investigated.

Two allelic variants of CYP76B1, E3C and 2DD, were isolated. High gene polymorphism has been reported in the case of some families of rapidly evolving mammalian or insect P450s important for the detoxification of drugs or insecticides (42, 43). In the context of the plant-pathogen warfare, a similar polymorphism and rapid evolution would be expected for enzymes directly participating in plant defense against pathogen attack. On the basis of sequence alignments, the insertion in E3C can be predicted to be located in the β sheet at the junction between helices D and E, or at the beginning of the E helix. This region is not likely to participate to the binding of substrate according to the multiple homology alignments (44) or mutant analysis (45) performed on animal enzymes. Only 2DD was expressed in yeast. Possible differences in substrate specifity or catalytic efficiency between the two variants could be nevertherless interesting to investigate, once more substrates of the enzyme are identified. On a genomic Southern blot analyzed with CYP76B1 (not shown) a complex pattern of strongly and more weakly hybridizing bands was detected. This seems to indicate that additional variants or closely related genes may be present in *H. tuberosus*.

We show here that CYP76B1 catalyzes the mono- and di-N-demethylation of both chlortoluron and isoproturon. Other phenylureas bind its active site with high affinity. Their positioning close to the heme iron is favorable to catalysis. Such binding parameters together with preliminary analysis of metabolites (not shown) indicate that CYP76B1 dealkylates most phenylureas, including the methoxylated forms like monolinuron or chlorbromuron. The $K_s$ of CYP76B1 for diuron (20 $\mu$M), is very similar to the $K_m$ previously reported for diuron demethylation (15 $\mu$M) in cotton seedling hypocotyl microsomes (Frear et al., 1969). This suggests that CYP76B1 is the *H. tuberosus* orthologue of the phenylurea dealkylase originally characterized by Frear et al. (1969) in cotton.

A few other P450s have previously been reported to metabolize chlortoluron. Recombinant human CYP1A1 (Shiota et al., 1994) and CYP3A4 (Mehmood et al., 1995) have low regiospecificity and catalyze both N-demethylation and ring-methyl hydroxylation of the herbicide. Although turnover numbers were not reported, data available indicate moderate efficiency. Two yeast-expressed plant enzymes, CYP73A1 (Pierrel et al., 1994) and CYP81 B1 (Cabello-Hurtado et al., 1998a), were also reported to catalyze ring-methyl hydroxylation of chlortoluron. In both cases, however, the reaction was extremely slow. This contrasts with very fast N-demethylation observed with CYP76B1. Turnover rates found for the first demethylation of chlortoluron and isoproturon (803 and 147 $min^{-1}$) very favorably compare to the turnover measured with physiological substrates. Even the second demethylation which is the slow step for complete detoxification of chlortoluron proceeds with a relatively high kCat of 46 $min^{-1}$. CYP76B1 is thus expected to be a major phenylurea metabolizing P450 in higher plants, and probably plays a significant role in the detoxification and selectivity of this broad class of photosystem II inhibitors. Phenylureas have been widely used for selective weed control in cereal crops and are considered as serious environmental contaminants. It may thus provide a strategy for bioremediation of contaminated sites.

Results from RNA blot hybridization show that the expression of CYP76B1 is strongly induced by different categories of xenobiotics, including low molecular weight solvent (DMSO), metal salt ($MnCl_2$), and globular organic molecules (i.e. drugs like aminopyrine or phenobarbital). The best inducer was the antipyretic drug aminopyrine, which is also a P450 substrate in *H. tuberosus* (17). Planar compounds like benzo(a)pyrene, naphthalic anhydride and flavone were ineffective or slightly reduced CYP76B1 expression.

Taken as a whole, our results suggest that the induction of alkoxycoumarin and alkoxyresorufin O-dealkylase activities in *H. tuberosus* provides a general marker of contamination by metals, solvents, as well as globular and planar organic molecules. The NADPH-dependent enzymic activity reflects the increased expression of several P450 proteins. CYP76B1 specific probes, however, seem to constitute more selective and sensitive tools, very responsive to some metals or to globular organic contaminants. The increase in alkoxycoumarin and alkoxyresorufin O-dealkylase activities, the increase in the CYP76B1 protein or the increase in the CYP76B1 transcripts in plant tissues can therefore be used as markers of chemical pollution of the atmosphere, of waters or of soils.

The expression of this sequence in yeast has shown that it encoded an enzyme very actively catalyzing the mono- and didealkylation of the two herbicides of the phenylurea family, chlortoluron and isoproturon. CYP76B1 very effectively attacks the N-dimethyl group which it oxidizes into an amine. All the phenylureas, and numerous other pesticides, carry this functional group and are therefore potential substrates of CYP76B1. Such a metabolism abolishes the phytotoxicity of these herbicides. CYP76B1 can consequently be used to manipulate the tolerance of plants sensitive to this family of herbicides. In the plant, CYP76B1 therefore appears to play an important role for the detoxification of herbicides.

On the other hand, the animal gene used by Shiota et al. CYP1A1) metabolizes chlortoluron with a fairly low efficiency, mainly by hydroxylation on the methyl at position 4 of the aromatic ring. This type of metabolism cannot be applied to the other phenylureas which are differently substituted at the level of the aromatic ring. CYP1A1 has, moreover, a major disadvantage for an agricultural use: it catalyzes the activation of very common industrial pollutants, such as benzo(a)pyrene, into carcinogenic compounds.

The cytochrome P450s require, for their function, the involvement of a reductase. The reductases of a given plant efficiently reduce the P450s of another plant. The reduction occurs less efficiently between reductases and P450s of different phyla. It is impossible between plant reductases and bacterial P450s. The plant transformations carried out up until now with bacterial or animal P450s (48, 50) were carried out after alteration of the sequences to promote the reduction of the enzyme. CYP76B1 being a plant microsomal enzyme, which is easily reduced by the plant microsomal P450 reductases (see above), no alteration of its sequence should be necessary in order to obtain a completely functional enzyme.

Plants being sedentary, having a large surface area of contact with their surroundings, and being capable of accumulating certain metals or organic compounds, they constitute a material more suited to the detection of environmental pollution. In a bioremediation perspective, i.e. soils or waters contaminated by organic pollutants, it is also possible to envisage producing transgenic plants overexpressing CYP76B1. The accumulation of deactivated residues in the aerial parts would allow their elimination by cutting and incineration.

References
1. Batard, Y., Zimmerlin, A., Le Ret, M., Durst, F., and Werck-Reichhart, D. (1995) *Plant Cell Environ.* 18, 523–533.
2. Sandermann, H. Jr. (1992) *Trends Biochem. Sci.* 17, 82–84.
3. Cunningham, S. D., and Ow, D. W. (1996) *Plant Physio.* 10, 715–719.
4. Sandermann, H. Jr. (1994) *Pharmacogenetics.* 4, 225–241.
5. Farago, S., Brunold, C., and Kreuz, K.(1994) *Physiol Plantarum.* 91, 537–542.

6. Cole, D. J. (1994) *Pestic. Sci.* 42, 209–222.
7. Kreuz, K., Tommasini, R., and Martinoia, E. (1996) *Plant Physiol.* 111, 349–353.
8. Bolwell, G. P., Bozac, K., and Zimmerlin, A. (1994) *Phytochemistry.* 37, 1491–1506.
9. Durst, F., and O'Keefe, D. (1995) *Drug Metab. Drug Interact.* 12, 171–187.
10. Barrett, M. (1995) *Drug Metab. Drug Interact.* 12, 299–315.
11. Frear, D. S. (1995) *Drug Metab. Drug Interact.* 12, 329–357.
12. Werck-Reichhart, D. (1995) In *Brighton Crop Protection Conference-Weeds*-1995, vol 3, pp 813–822.
13. Reichhart, D., Salaun, J. P., Benveniste, I., and Durst F. (1980) *Plant Physiol.* 66, 600–604.
14. Adelé, P., Reichhart, D., Salaün. J. P., Benveniste, I., and Durst, F. (1981) *Plant. Sci. Lett.* 22, 39–46.
15. Fujita, M. (1985) *Agric. Biol. Chem.* 49, 3045–3047.
16. Salaün, J. P., Simon, A., and Durst, F. (1986) *Lipids.* 21, 776–779.
17. Fonné-Pfister, R., Simon, A., Salaün, J. P., and Durst, F. (1988) *Plant Sci.* 55, 9–20.
18. McFadden, J. J., Gronwald, J. W., and Eberlein, C. V. (1990) *Biochem. Res. Comm.* 168, 206–213.
19. Mougin, C., Polge, N., Scalla, R., and Cabanne, F. (1991) *Pestic. Biochem. Physiol.* 40, 1–11.
20. Moreland, D. E., and Corbin, F. T. (1991) *Z. Naturforsch.* 46c, 906–914.
21. Persan, M. W., and Schuler, M. A. (1995) *Plant Physiol.* 109, 1483–1490.
22. Batard, Y., Schalk, M., Pierrel, M. A., Zimmerlin, A., Durst, F. and Werck-Reichhart, D. (1997) *Plant Physiol.,* 113, 951–959.
23. Ullrich, V., Frommer, U., and Weber, P. (1973) *Hoppe-Seyler's Z. Physiol. CHem.* 354, 514–520.
24. Yamazaki, H., Inoue, K., Mimura, M., Oda, Y., Guengerich, F. P., and Shimada T. (1996) *Biochemical Pharmacol.* 51, 313–319.
25. Stegeman, J. J., and Lech, J. J. (1991) *Environ. Health Perspectives.* 90, 101–109.
26. Nims, R. W. and Lubet, R. A. (1995) *J. Toxicol. Env. Health.* 46, 271–292.
27. Werck-Reichhart, D., Gabriac, B., Teutsch, H., and Durst, F. (1990) *Biochem. J.* 270, 729–735.
28. Marabini, L., Radice, S., Cipeletti, B., and Chiesara, E. (1994) *Plant Sci.* 99, 135–140.
29. Sugiura, M., Sakaki, T., Yabusaki, Y., and Ohkawa, H. (1996) *Biochim. Biophys. Acta.* 1308, 231–240.
30. Lesot, A., Benveniste, I., Hasenfratz, M. P., and Durst, F. (1990) *Plant Cell Physiol.* 31, 1177–1182.
31. Sambrook, J., Fritsch, E. F., and Maniatis, T. (1989) *Molecular cloning: a laboratory manual,* 2nd Ed., Cold Spring Harbor Lab. Press Plainview, N.Y.
32. Pompon, D., Louerat, B., Bronine, A., and Urban, P. (1996) *Methods Enzymol.* 272, 51–64.
33. Pierrel, M. A., Batard, Y., Kazmaier, M., Mignotte-Vieux, C., Durst, F., and Werck-Reichhart, D. (1994) *Eur. J. Biochem.* 224, 835–844.
34. Gabriac, B., Werck-Reichhart, D., Teutsch, H., and Durst, F. (1990) *Arch. Biochem. Biophys.* 288, 302–309.
35. Devereux, J., Heaberlin, P., and Smithies, O. (1984) *Nucleic Acids Res.* 12, 387–395.
36. Felsenstein, J. (1989) *Cladistics* 5, 164–166.
37. Page, R. D. M. (1996) *Comp. Applic. Biosci.* 12, 357–358.
38. Nelson, D. R., Kamataki, T., Waxman, D. J., Guengerich, F. P., Estabrook, R. W., Feyereisen, R., Gonzalez, F. J., Coon, M. J., Gunsalus, I. C., Gotoh, O., Okuda, K., Nebert, D. W. (1993) *DNA and Cell Biology.* 12, 1–51.
39. Durst, F., and Nelson, D. R. (1995) *Drug Metab. Drug Interact.* 12, 189–206.
40. Toguri, T., Kobayashi, O., and Umemoto, N. (1993) *Biochim. Biophys. Acta. 1216,* 165–169.
41. Holton, T., Brugliera, F., Lester, D. R., Tanaka, Y., Hyland, C. D., Menting, J. G. T., Lu, C. Y., Farcy, E., Srevenson, T. W., and Cornish, E. C. (1993) *Nature.* 366, 276–279.
42. Heim, M. H., and Meyer, U. A. (1992) *Genomics.* 14, 49–58.
43. Dunkov, B. C., Rodriguez-Arnaiz, R., Pittendrigh, B., Ffrench-Constant, R. H., and Feyereisen, R. (1996) *Mol. Gen. Genet.* 251, 290–297.
44. Gotoh, O. (1992) *J. Biol. Chem.* 267, 83–90.
45. Negishi, M., Uno, T., Darden, T. A., Sueyoshi, T., and Pederesen, L. G. (1996) *FASEB J.* 10, 683–689.
46. Stegeman, J. J. and Lech J. J. (1991) *Environm. Health Perspectives,* 90, 101–109,
47. Garriges, Ph., Narbonne, J. F., Lafaurie, M., Ribera, D., Lemaire, P., Raoux, C., Michel, X., Salaun, J. P., Monod, J. L. & Romeo, M. (1993) *The Science of the Total Environment* 139/140, 225–236.
48. Shiota, N., Nagasawa, A., Sakaki, T., Yabusaki, Y., Ohkawa, H. (1994) *Plant Physiol.* 106, 17–23.
49. Shiota.N., Inui, H. and Okhawa, H. (1996) *Pestic. biochem. Physiol.* 54, 190–198.
50. O'Keefe, D. P., Tepperman, J. M., Dean, C., Leto, K. J., Erbes, D., Odell. J. T. (1994) *Plan Physiol* 105, 473–482.
51. Benveniste, I., Gabriac, B., Durst, F. (1986) Purification and characterization of the NADPH-cytochrome P450 (cytochrome c) reductase from higher-plant microsomal faction. *Biochem. J.* 235, 365–373.
52. Cabello-Hurtado, F., Batard, Y., Salaün, J. P., Durst, F., Pinot, F., Werck-Reichhard, D. (1998a) Cloning, expresion in yeast and functional characterization of CYP81 B1, a plant P450 which catalyzes in-chain hydroxylation of fatty acids. *J. Biol. Chem.* 273, 7260–7267.
53. Cabello-Hurtado, F., Durst, F., Jorrin, J. V., Werck-Reichhard, D. (1998b) Coumarins in *Helianthus tuberosus:* characterization, induced accumulation and biosynthesis. *Phytochemistry* in press.
54. Duggleby, R. G. (1984) Regression analysis of nonlinear Arrhenius plots an empirical model and a computer program. *Comput. Biol. Med.* 14, 447–455.
55. Fonné, R. (1985) Intervention du cytochrome P450 des végétaux supérieurs dans l'oxydation de composés exogénes: l'aminopyrine et le chlortoluron. PhD Thesis, Université Louis Pasteur, Strasbourg.
56. Frear, D. S. Swanson, H. R., Tanaka, F. S. (1969) N-demethylation of substituted 3-(phenyl)-1-methylureas: isolation and characterization of a microsomal mixed function oxidase from cotton. *Phytochemistry* 8, 2157–2169.
57. Gabriac, B., Werck-Reichhart, D., Teutsch, G. H., Durst, F. (1991) Purification and immunocharacterization of a plant cytochrome P450: the cinnamic acid 4-hydroxylase. *Arch. Biochem. Biophys.* 288, 302–309.
58. Higashi, K., Nakashima, K., Karasaki, Y., Fukunaga, M., Mizuguchi, Y. (1981) Activation of benzo(a)pyrene by microsomes of higher plant tissues and their mutagenesis. *Biochem. Internat.* 2, 373–380.
59. Jefcoate, C. R. (1978) Measurement of substrate and inhibitor binding to microsomal cytochrome P450 by optical-difference spectroscopy. *Methods Enzymol.* 52, 258–279.

60. Mehmoud, Z., Kelly, D. E., Kelly, S. L. (1995) Metabolism of the herbicide chlortoluron by human cytochrome P4503A4. *Chemosphere* 11/12, 4515–4529.
61. Raag, R., Poulos, T. L. (1989) The structural basis for substrate-induced changes in redox potential and spin equilibrium in cytochrome P450$_{CAM}$. *Biochemistry* 28, 917–922.
62. Teutsch, G. H., Hasenfratz, M. P., Lesot, A., Stotitz, C., Garnier, J. M., Jeltsch, J. M., Durst, F., Werck-Reichhart, D. (1993) Isolation and sequence of a cDNA encoding the Jerusalem artichoke cinnamate hydroxylase, a major plant cytochrome P450 involved in the general phenylpropanoid pathway. *Proc. Natl. Acad. Sci. USA* 90, 4102–4106.
63. Urban, P., Mignotte, C., Kazmaier, M., Delorme, F., Pompon, D. (1997) Cloning, yeast expression, and characterization of the coupling of two distantly related *Arabidopsis thaliana* NADPH-cytochrome P450 reductases with P450 CYP73A5. *J. Biol. Chem.* 272, 19176–19186.
64. Werck-Reichhart, D., Batard, Y., Kochs, G., Lesot, A., Durst, F. (1993) Monospecific polyclonal antibodies directed against purified cinnamate 4-hydroxylase from *Helianthus tuberosus* : immunopurification, immunoquantitation, interspecies cross-reactivity. *Plant Physiol.* 102, 1291–1298.
65. Gachotte, D. (1995) PhD thesis.
66. Ditta, G., Stanfield, S., Corbin, D., Helsinki, D. R. (1980) Broad host range DNA cloning system for gram-negative bacteria: construction of a gene bank of *Rhizobium meliloti. Proc. Natl. Acad. Sci. USA* 77, 7347–7351.
67. Horsch, R. B., Fry, J. E., Hoffmann, N. L., Wallroth, M., Eichholtz, D., Rogers, S. G., Fraley, R. T. (1985) A simple and general method for transferring genes into plants. *Science* 227, 1229–1231.

What is claimed is:

1. An isolated DNA encoding a polypeptide, wherein said polypeptide comprises an amino acid sequence selected from the group consisting of:
   a) the amino acid sequence of SEQ ID NO:1, and
   b) the amino acid sequence of SEQ ID NO:2.

2. An isolated nucleic acid selected from the group consisting of:
   a) SEQ ID NO:1,
   b) SEQ ID NO:2,
   c) a DNA having a sequence fully complementary to the sequence of SEQ ID NO:1 or SEQ ID NO:2,
   d) SEQ ID NO:3,
   e) SEQ ID NO:4, and
   f) an mRNA encoded by SEQ ID NO:1 or SEQ ID NO:2.

3. A vector comprising a DNA sequence as claimed in claim 1.

4. The vector as claimed in claim 3, wherein said vector is a plasmid.

5. A host cell, which has been transformed by a vector as claimed in claim 3.

6. The host cell as claimed in claim 5, wherein said host cell is *Saccharomyces cerevisiae*.

7. The host cell as claimed in claim 5, wherein said host cell is a plant cell.

8. A transgenic plant having increased resistance phenylurea to herbicides, wherein said plant is transformed by a vector as claimed in claim 3.

9. The transgenic plant as claimed in claim 8, wherein said plant is selected from the group consisting of tobacco, cotton, soybean, melon, corn, wheat, and rice.

10. The isolated DNA sequence as claimed in claim 2, which is selected from the group consisting of:
    a) SEQ ID NO 1, and
    b) SEQ ID NO 2.

* * * * *

SEQUENCE LISTING

<160> NUMBER OF SEQ ID NOS: 27

<210> SEQ ID NO 1
<211> LENGTH: 1737
<212> TYPE: DNA
<213> ORGANISM: Helianthus tuberosus
<220> FEATURE:
<221> NAME/KEY: CDS
<222> LOCATION: (25)..(1494)

<400> SEQUENCE: 1

```
gtgacacaca cacaccatct aata atg gat ttt ctt ata ata gtg agt act       51
                          Met Asp Phe Leu Ile Ile Val Ser Thr
                           1               5 ctt ctc tta tct tac ata ctt atc tgg gtt ttg ggg gta ggc aaa ccc       99
Leu Leu Leu Ser Tyr Ile Leu Ile Trp Val Leu Gly Val Gly Lys Pro
 10              15                  20                  25 aag aac tta cct cca ggc cca aca cgg ttg ccg atc ata gga aac ctc      147
Lys Asn Leu Pro Pro Gly Pro Thr Arg Leu Pro Ile Ile Gly Asn Leu
             30                  35                  40 cac ttg ctg gga gcg tta ccg cac cag tcg cta gcg aaa cta gcc aaa      195
His Leu Leu Gly Ala Leu Pro His Gln Ser Leu Ala Lys Leu Ala Lys
         45                  50                  55 att cat ggc ccg ata atg tct tta caa ctc ggt cag atc acc acg ctc      243
Ile His Gly Pro Ile Met Ser Leu Gln Leu Gly Gln Ile Thr Thr Leu
     60                  65                  70 gtc ata tcc tca gct act gcc gcg gaa gaa gta ctc aaa aag caa gac      291
Val Ile Ser Ser Ala Thr Ala Ala Glu Glu Val Leu Lys Lys Gln Asp
 75                  80                  85 ctt gct ttc tcc aca cgt aat gtc cct gac gca gtg cgt gcc tat aac      339
Leu Ala Phe Ser Thr Arg Asn Val Pro Asp Ala Val Arg Ala Tyr Asn
 90                  95                 100                 105 cac gag cga cac tcc atc tca ttt ctc cat gtg tgc aca gag tgg cgc      387
His Glu Arg His Ser Ile Ser Phe Leu His Val Cys Thr Glu Trp Arg
            110                 115                 120 acc ctc aga agg atc gtt agt tcc aat atc ttc tcc aac agc tct ctt      435
Thr Leu Arg Arg Ile Val Ser Ser Asn Ile Phe Ser Asn Ser Ser Leu
        125                 130                 135 gaa gcc aaa cag cac ttg agg agc aag aaa gtt gaa gag cta ata gca      483
Glu Ala Lys Gln His Leu Arg Ser Lys Lys Val Glu Glu Leu Ile Ala
    140                 145                 150 tac tgc cgg aaa gct gct ctt tcg aat gaa aat gtg cac atc ggt cgt      531
Tyr Cys Arg Lys Ala Ala Leu Ser Asn Glu Asn Val His Ile Gly Arg
```

-continued

```
               155                 160                 165
gct gca ttt aga acc tcg ttg aat ctt tta tcc aac act att ttc tcc    579
Ala Ala Phe Arg Thr Ser Leu Asn Leu Leu Ser Asn Thr Ile Phe Ser
170                 175                 180                 185 aaa gat tta aca gac ccg tat gag gat tca ggt aaa gag ttt agg gag    627
Lys Asp Leu Thr Asp Pro Tyr Glu Asp Ser Gly Lys Glu Phe Arg Glu
                190                 195                 200 gtg att acc aac att atg gtg gac tct gca aag aca aat ctt gtt gac    675
Val Ile Thr Asn Ile Met Val Asp Ser Ala Lys Thr Asn Leu Val Asp
            205                 210                 215 gta ttt cca gtg ttg aag aag att gat cca caa ggg atc aag aga gga    723
Val Phe Pro Val Leu Lys Lys Ile Asp Pro Gln Gly Ile Lys Arg Gly
        220                 225                 230 atg gct cgt cat ttt tcc aag gtt ctt ggg ata ttt gat cag tta att    771
Met Ala Arg His Phe Ser Lys Val Leu Gly Ile Phe Asp Gln Leu Ile
    235                 240                 245 gaa gag aga atg aga acg ggc aga ttc gaa caa ggt gat gta ttg gac    819
Glu Glu Arg Met Arg Thr Gly Arg Phe Glu Gln Gly Asp Val Leu Asp
250                 255                 260                 265 gtg tgt ttg aaa atg atg caa gat aac cca aat gag ttc aat cac aca    867
Val Cys Leu Lys Met Met Gln Asp Asn Pro Asn Glu Phe Asn His Thr
                270                 275                 280 aac ata aag gct ttg ttt ttg gat ttg ttt gtt gct ggc act gat aca    915
Asn Ile Lys Ala Leu Phe Leu Asp Leu Phe Val Ala Gly Thr Asp Thr
            285                 290                 295 acc tcg att aca ata gaa tgg gcg atg aca gaa cta cta cgc aaa cca    963
Thr Ser Ile Thr Ile Glu Trp Ala Met Thr Glu Leu Leu Arg Lys Pro
        300                 305                 310 cac atc atg agt aaa gcg aaa gag gag ctt gaa aaa gtt att ggt aaa    1011
His Ile Met Ser Lys Ala Lys Glu Glu Leu Glu Lys Val Ile Gly Lys
    315                 320                 325 ggt agt atc gta aaa gag gat gat gta ttg agg cta ccc tac tta tca    1059
Gly Ser Ile Val Lys Glu Asp Asp Val Leu Arg Leu Pro Tyr Leu Ser
330                 335                 340                 345 tgc att gtg aaa gaa gtc tta cga ctg cac ccg cca tcc ccc tta ctt    1107
Cys Ile Val Lys Glu Val Leu Arg Leu His Pro Pro Ser Pro Leu Leu
                350                 355                 360 ctt cca cga aaa gtt gtg aca cag gta gaa ctc agt gga tac act ata    1155
Leu Pro Arg Lys Val Val Thr Gln Val Glu Leu Ser Gly Tyr Thr Ile
            365                 370                 375 cca gcg ggc aca ctg gtg ttt gtg aat gca tgg gcc ata gga aga gac    1203
Pro Ala Gly Thr Leu Val Phe Val Asn Ala Trp Ala Ile Gly Arg Asp
        380                 385                 390 cca acc gta tgg gat gac tca cta gag ttc aag cca caa cga ttt ttg    1251
Pro Thr Val Trp Asp Asp Ser Leu Glu Phe Lys Pro Gln Arg Phe Leu
    395                 400                 405 gag tcc agg ctt gat gtc cga ggt cat gat ttc gat tta atc ccg ttt    1299
Glu Ser Arg Leu Asp Val Arg Gly His Asp Phe Asp Leu Ile Pro Phe
410                 415                 420                 425 ggt gct gga cga aga ata tgc cct ggc ata cca ctt gca aca cgt atg    1347
Gly Ala Gly Arg Arg Ile Cys Pro Gly Ile Pro Leu Ala Thr Arg Met
                430                 435                 440 gtc cct atc atg ttg ggc tca tta ctc aat aat ttt gac tgg aaa att    1395
Val Pro Ile Met Leu Gly Ser Leu Leu Asn Asn Phe Asp Trp Lys Ile
            445                 450                 455 gac act aag gtt cca tat gat gtt ttg gac atg act gag aaa aat gga    1443
Asp Thr Lys Val Pro Tyr Asp Val Leu Asp Met Thr Glu Lys Asn Gly
        460                 465                 470 acc act ata tcc aag gcc aaa cct ctg tgt gtt gtt cca ata cca ttg    1491
```

-continued

```
Thr Thr Ile Ser Lys Ala Lys Pro Leu Cys Val Val Pro Ile Pro Leu
    475                 480                 485 aac tagcatccat tcatcttgtt tgaagtccga taatcaagcg caaccgagtt             1544
Asn
490 ggaagaagaa gaaaaaacgc agcaaccttt tatttgttta tttattagtc taatgggtca     1604 aattgtttac tgtttatatt ttatttagaa cttggccgta ggccatgtcc agtgggtcaa     1664 acaattagtt gtccagtagg gttaatatta tgtaatttgc ttttgggccc taacatgtga     1724 accggttgtt ggc                                                        1737

<210> SEQ ID NO 2
<211> LENGTH: 1634
<212> TYPE: DNA
<213> ORGANISM: Helianthus tuberosus
<220> FEATURE:
<221> NAME/KEY: CDS
<222> LOCATION: (1)..(1425)
<223> OTHER INFORMATION: E3C

<400> SEQUENCE: 2 tgg gtt ttg ggg gta ggc aaa ccc aag aac tta cct cca ggc cca aca        48
Trp Val Leu Gly Val Gly Lys Pro Lys Asn Leu Pro Pro Gly Pro Thr
 1               5                  10                  15 cgg ttg ccg atc ata gga aac ctc cac ttg ctt gga gcg tta ccg cac        96
Arg Leu Pro Ile Ile Gly Asn Leu His Leu Leu Gly Ala Leu Pro His
            20                  25                  30 cag tcg cta gcg aaa cta gcc aaa att cat ggc ccg ata atg tct tta       144
Gln Ser Leu Ala Lys Leu Ala Lys Ile His Gly Pro Ile Met Ser Leu
        35                  40                  45 caa ctc ggt cag atc acc acg ctc gtc ata tcc tca gcc act gcc gcg       192
Gln Leu Gly Gln Ile Thr Thr Leu Val Ile Ser Ser Ala Thr Ala Ala
    50                  55                  60 gaa gaa gta ctc aaa aag caa gac ctt gct ttc tcc aca cgt aat gtc       240
Glu Glu Val Leu Lys Lys Gln Asp Leu Ala Phe Ser Thr Arg Asn Val
65                  70                  75                  80 cct gac gcg gtg cgt gcc tat aac cac gag cga cac tcc atc tca ttt       288
Pro Asp Ala Val Arg Ala Tyr Asn His Glu Arg His Ser Ile Ser Phe
                85                  90                  95 ctc cat gtg tgc acg gag tgg cgc acc ctc aga agg att gtt agt tcc       336
Leu His Val Cys Thr Glu Trp Arg Thr Leu Arg Arg Ile Val Ser Ser
            100                 105                 110 aat atc ttc tcc aac agc tct ctt gaa gcc aaa cag cac ttg agg agc       384
Asn Ile Phe Ser Asn Ser Ser Leu Glu Ala Lys Gln His Leu Arg Ser
        115                 120                 125 aag aaa gtt gaa gag cta ata gca tac tgc cgg aaa gct gct ctt tcg       432
Lys Lys Val Glu Glu Leu Ile Ala Tyr Cys Arg Lys Ala Ala Leu Ser
    130                 135                 140 aat gaa aat gtg cac atc ggt cgt gct gca ttt aga acc tcg ttg aat       480
Asn Glu Asn Val His Ile Gly Arg Ala Ala Phe Arg Thr Ser Leu Asn
145                 150                 155                 160 ctt tta tcc aac act att ttc tcc aag gat tta aca gac ccg tat gag       528
Leu Leu Ser Asn Thr Ile Phe Ser Lys Asp Leu Thr Asp Pro Tyr Glu
                165                 170                 175 gat tca gct tca ggt aaa gag ttt agg gag gtg att acc aac att atg       576
Asp Ser Ala Ser Gly Lys Glu Phe Arg Glu Val Ile Thr Asn Ile Met
            180                 185                 190 gtg gac tct gca aag aca aat ctt gtt gac gta ttt cca gtg ttg aag       624
Val Asp Ser Ala Lys Thr Asn Leu Val Asp Val Phe Pro Val Leu Lys
        195                 200                 205
```

-continued

| | |
|---|---|
| agg att gat cca caa ggg atc aag aga gga atg gct cgt cat ttt tcc<br>Arg Ile Asp Pro Gln Gly Ile Lys Arg Gly Met Ala Arg His Phe Ser<br>210             215             220 | 672 |
| aag gtt ctt ggg ata ttt gat cag tta att gaa gag aga atg aga acg<br>Lys Val Leu Gly Ile Phe Asp Gln Leu Ile Glu Glu Arg Met Arg Thr<br>225             230             235             240 | 720 |
| ggc aga ttc gaa caa ggt gat gta ttg gac gtg tgt ttg aaa atg atg<br>Gly Arg Phe Glu Gln Gly Asp Val Leu Asp Val Cys Leu Lys Met Met<br>             245             250             255 | 768 |
| caa gat aac cca aat gag ttc aat cac aca aac ata aag gct ttg ttt<br>Gln Asp Asn Pro Asn Glu Phe Asn His Thr Asn Ile Lys Ala Leu Phe<br>260             265             270 | 816 |
| ttg gat ttg ttt gtt gct ggc act gat aca acc tcg att aca ata gaa<br>Leu Asp Leu Phe Val Ala Gly Thr Asp Thr Thr Ser Ile Thr Ile Glu<br>275             280             285 | 864 |
| tgg gcg atg aca gaa cta cta cgc aaa cca cac atc atg agt aaa gcg<br>Trp Ala Met Thr Glu Leu Leu Arg Lys Pro His Ile Met Ser Lys Ala<br>290             295             300 | 912 |
| aaa gag gag ctt gaa aaa gtt att ggt aaa ggt agt atc gta aaa gag<br>Lys Glu Glu Leu Glu Lys Val Ile Gly Lys Gly Ser Ile Val Lys Glu<br>305             310             315             320 | 960 |
| gat gat gta ttg agg cta ccc tac tta tca tgc att gtg aaa gaa gtc<br>Asp Asp Val Leu Arg Leu Pro Tyr Leu Ser Cys Ile Val Lys Glu Val<br>             325             330             335 | 1008 |
| tta cga ctg cac ccg cca tcc ccc tta ctt ctt cca cga aaa gtt gtg<br>Leu Arg Leu His Pro Pro Ser Pro Leu Leu Leu Pro Arg Lys Val Val<br>340             345             350 | 1056 |
| aca cag gta gaa ctc agt gga tac act ata cca gcg ggc aca ctg gtg<br>Thr Gln Val Glu Leu Ser Gly Tyr Thr Ile Pro Ala Gly Thr Leu Val<br>355             360             365 | 1104 |
| ttt gtg aat gca tgg gct ata gga aga gac cca acc gta tgg gat gac<br>Phe Val Asn Ala Trp Ala Ile Gly Arg Asp Pro Thr Val Trp Asp Asp<br>370             375             380 | 1152 |
| tca cta gag ttc aag cca caa cga ttt ttg gag tcc agg ctt gat gtc<br>Ser Leu Glu Phe Lys Pro Gln Arg Phe Leu Glu Ser Arg Leu Asp Val<br>385             390             395             400 | 1200 |
| cga ggt cat gat ttc gat tta atc ccg ttt ggt gct gga cga aga ata<br>Arg Gly His Asp Phe Asp Leu Ile Pro Phe Gly Ala Gly Arg Arg Ile<br>             405             410             415 | 1248 |
| tgc cct ggc ata cca ctt gca aca cgt atg gtc cct atc atg ttg ggc<br>Cys Pro Gly Ile Pro Leu Ala Thr Arg Met Val Pro Ile Met Leu Gly<br>420             425             430 | 1296 |
| tca tta ctc aat aat ttt gac tgg aaa att gac act aag gtt cca tat<br>Ser Leu Leu Asn Asn Phe Asp Trp Lys Ile Asp Thr Lys Val Pro Tyr<br>435             440             445 | 1344 |
| gat gtt ttg gac atg act gag aaa aat gga acc act ata tcc aag gcc<br>Asp Val Leu Asp Met Thr Glu Lys Asn Gly Thr Thr Ile Ser Lys Ala<br>450             455             460 | 1392 |
| aaa cct ctg tgt gtt gtt cca ata cca ttg aac tagcatccat tcatcttgtt<br>Lys Pro Leu Cys Val Val Pro Ile Pro Leu Asn<br>465             470             475 | 1445 |
| tgaagtccga taatcaagcg caaccgagtt cgaagaagaa gaaaaaacgc agcagccttt | 1505 |
| tatttgttta tttattagtc taatgggtca aattgtttac tgtttatatt ttatttagaa | 1565 |
| cttgggccgt aggccatgtc cagtgggtca aacaattagt agtccagtag ggttaatatt | 1625 |
| atgtaattt | 1634 |

<210> SEQ ID NO 3
<211> LENGTH: 38

```
<212> TYPE: DNA
<213> ORGANISM: Artificial Sequence
<220> FEATURE:
<223> OTHER INFORMATION: Description of Artificial Sequence: Sense
      primer derived from Helianthus tuberosus CYP76B1 nucleic acid
      sequence.

<400> SEQUENCE: 3
atatatggat ccatggattt tcttataata gtgagtac                         38

<210> SEQ ID NO 4
<211> LENGTH: 41
<212> TYPE: DNA
<213> ORGANISM: Artificial Sequence
<220> FEATURE:
<223> OTHER INFORMATION: Description of Artificial Sequence: Reverse
      primer derived from Helianthus tuberosus CYP76B1 nucleic acid
      sequence

<400> SEQUENCE: 4
tatatagaat tcatgctagt tcaatggtat tggaacaaca c                     41

<210> SEQ ID NO 5
<211> LENGTH: 12
<212> TYPE: PRT
<213> ORGANISM: Helianthus tuberosus

<400> SEQUENCE: 5

Met Glu Leu His Leu Ser Leu Thr Ile Ala Thr Phe
 1               5                   10

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Sense
      primer derived from Helianthus tuberosus cytochrome P450
      polypeptide coding sequence.
<221> NAME/KEY: modified_base
<222> LOCATION: (7)
<223> OTHER INFORMATION: i
<221> NAME/KEY: modified_base
<222> LOCATION: (13)
<223> OTHER INFORMATION: i
<221> NAME/KEY: modified_base
<222> LOCATION: (16)
<223> OTHER INFORMATION: i
<221> NAME/KEY: modified_base
<222> LOCATION: (19)
<223> OTHER INFORMATION: i
<221> NAME/KEY: modified_base
<222> LOCATION: (22)
<223> OTHER INFORMATION: i

<400> SEQUENCE: 6
ggarytncay ytnwsnytna cnatygc                                     27

<210> SEQ ID NO 7
<211> LENGTH: 13
<212> TYPE: PRT
<213> ORGANISM: Helianthus tuberosus

<400> SEQUENCE: 7

Ile Gln His Tyr Glu Leu Leu Pro Phe Gly Ser Gly Arg
 1               5                   10

<210> SEQ ID NO 8
<211> LENGTH: 13
```

```
<212> TYPE: PRT
<213> ORGANISM: Helianthus tuberosus

<400> SEQUENCE: 8

Gly Gln Glu Tyr Glu Leu Leu Pro Phe Gly Ser Gly Arg
  1               5                  10

<210> SEQ ID NO 9
<211> LENGTH: 17
<212> TYPE: DNA
<213> ORGANISM: Artificial Sequence
<220> FEATURE:
<223> OTHER INFORMATION: Description of Artificial Sequence: Reverse
      primer derived form Helianthus tuberosus cytochrome P450
      polypeptide coding sequence
<221> NAME/KEY: modified_base
<222> LOCATION: (3)
<223> OTHER INFORMATION: i
<221> NAME/KEY: modified_base
<222> LOCATION: (6)
<223> OTHER INFORMATION: i
<221> NAME/KEY: modified_base
<222> LOCATION: (9)
<223> OTHER INFORMATION: i

<400> SEQUENCE: 9
cgnccnganc craangg                                                17

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Reverse
      primer derived from Helianthus tuberosus cytochrome P450
      polypeptide coding sequence
<221> NAME/KEY: modified_base
<222> LOCATION: (3)
<223> OTHER INFORMATION: i

<400> SEQUENCE: 10
aanggnarna rytcrtartg                                             20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Reverse
      primer derived from Helianthus tuberosus cytochrome P450
      polypeptide coding sequence
<221> NAME/KEY: modified_base
<222> LOCATION: (3)
<223> OTHER INFORMATION: i

<400> SEQUENCE: 11
aanggnarna rytcrtaytc                                             20

<210> SEQ ID NO 12
<211> LENGTH: 12
<212> TYPE: PRT
<213> ORGANISM: Helianthus tuberosus

<400> SEQUENCE: 12

Asn Met Pro Phe Ile Leu Leu Tyr Ile Ala Val Leu
  1               5                  10

<210> SEQ ID NO 13
<211> LENGTH: 20
```

```
<212> TYPE: DNA
<213> ORGANISM: Artificial Sequence
<220> FEATURE:
<223> OTHER INFORMATION: Description of Artificial Sequence: Sense
      primer derived from Helianthus uberosus cytochrome 450 polypeptide
      coding sequence
<221> NAME/KEY: modified_base
<222> LOCATION: (9)
<223> OTHER INFORMATION: i
<221> NAME/KEY: modified_base
<222> LOCATION: (12)
<223> OTHER INFORMATION: i

<400> SEQUENCE: 13
ttyathytny tntayatygc                                            20

<210> SEQ ID NO 14
<211> LENGTH: 10
<212> TYPE: PRT
<213> ORGANISM: Helianthus tuberosus

<400> SEQUENCE: 14

Gln Glu Glu Leu Asp Leu His Val Gly Arg
 1               5                  10

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Sense
      primer derived from Helianthus tuberosus cytochrome P450
      polypeptide coding sequence
<221> NAME/KEY: modified_base
<222> LOCATION: (12)
<223> OTHER INFORMATION: i
<221> NAME/KEY: modified_base
<222> LOCATION: (18)
<223> OTHER INFORMATION: i

<400> SEQUENCE: 15
ccrgargary tngayytnca y                                          21

<210> SEQ ID NO 16
<211> LENGTH: 490
<212> TYPE: PRT
<213> ORGANISM: Helianthus tuberosus

<400> SEQUENCE: 16

Met Asp Phe Leu Ile Ile Val Ser Thr Leu Leu Ser Tyr Ile Leu
 1               5                  10                  15

Ile Trp Val Leu Gly Val Gly Lys Pro Lys Asn Leu Pro Pro Gly Pro
                20                  25                  30

Thr Arg Leu Pro Ile Ile Gly Asn Leu His Leu Leu Gly Ala Leu Pro
                35                  40                  45

His Gln Ser Leu Ala Lys Leu Ala Lys Ile His Gly Pro Ile Met Ser
        50                  55                  60

Leu Gln Leu Gly Gln Ile Thr Thr Leu Val Ile Ser Ser Ala Thr Ala
65                  70                  75                  80

Ala Glu Glu Val Leu Lys Lys Gln Asp Leu Ala Phe Ser Thr Arg Asn
                85                  90                  95

Val Pro Asp Ala Val Arg Ala Tyr Asn His Glu Arg His Ser Ile Ser
                100                 105                 110

Phe Leu His Val Cys Thr Glu Trp Arg Thr Leu Arg Arg Ile Val Ser
            115                 120                 125
```

```
Ser Asn Ile Phe Ser Asn Ser Ser Leu Glu Ala Lys Gln His Leu Arg
    130                 135                 140
Ser Lys Lys Val Glu Glu Leu Ile Ala Tyr Cys Arg Lys Ala Ala Leu
145                 150                 155                 160
Ser Asn Glu Asn Val His Ile Gly Arg Ala Ala Phe Arg Thr Ser Leu
                165                 170                 175
Asn Leu Leu Ser Asn Thr Ile Phe Ser Lys Asp Leu Thr Asp Pro Tyr
            180                 185                 190
Glu Asp Ser Gly Lys Glu Phe Arg Glu Val Ile Thr Asn Ile Met Val
        195                 200                 205
Asp Ser Ala Lys Thr Asn Leu Val Asp Val Phe Pro Val Leu Lys Lys
    210                 215                 220
Ile Asp Pro Gln Gly Ile Lys Arg Gly Met Ala Arg His Phe Ser Lys
225                 230                 235                 240
Val Leu Gly Ile Phe Asp Gln Leu Ile Glu Glu Arg Met Arg Thr Gly
                245                 250                 255
Arg Phe Glu Gln Gly Asp Val Leu Asp Val Cys Leu Lys Met Met Gln
            260                 265                 270
Asp Asn Pro Asn Glu Phe Asn His Thr Asn Ile Lys Ala Leu Phe Leu
        275                 280                 285
Asp Leu Phe Val Ala Gly Thr Asp Thr Thr Ser Ile Thr Ile Glu Trp
    290                 295                 300
Ala Met Thr Glu Leu Leu Arg Lys Pro His Ile Met Ser Lys Ala Lys
305                 310                 315                 320
Glu Glu Leu Glu Lys Val Ile Gly Lys Gly Ser Ile Val Lys Glu Asp
                325                 330                 335
Asp Val Leu Arg Leu Pro Tyr Leu Ser Cys Ile Val Lys Glu Val Leu
            340                 345                 350
Arg Leu His Pro Pro Ser Pro Leu Leu Pro Arg Lys Val Val Thr
    355                 360                 365
Gln Val Glu Leu Ser Gly Tyr Thr Ile Pro Ala Gly Thr Leu Val Phe
    370                 375                 380
Val Asn Ala Trp Ala Ile Gly Arg Asp Pro Thr Val Trp Asp Asp Ser
385                 390                 395                 400
Leu Glu Phe Lys Pro Gln Arg Phe Leu Glu Ser Arg Leu Asp Val Arg
                405                 410                 415
Gly His Asp Phe Asp Leu Ile Pro Phe Gly Ala Gly Arg Arg Ile Cys
            420                 425                 430
Pro Gly Ile Pro Leu Ala Thr Arg Met Val Pro Ile Met Leu Gly Ser
        435                 440                 445
Leu Leu Asn Asn Phe Asp Trp Lys Ile Asp Thr Lys Val Pro Tyr Asp
    450                 455                 460
Val Leu Asp Met Thr Glu Lys Asn Gly Thr Thr Ile Ser Lys Ala Lys
465                 470                 475                 480
Pro Leu Cys Val Val Pro Ile Pro Leu Asn
                485                 490

<210> SEQ ID NO 17
<211> LENGTH: 467
<212> TYPE: PRT
<213> ORGANISM: Solanum melongena

<400> SEQUENCE: 17

Phe Gly Asn Met Phe Asp Leu Ala Gly Ser Ala Pro Tyr Lys Lys Ile
```

```
  1               5               10              15
Ala Cys Leu Lys Glu Lys Tyr Gly Pro Ile Leu Trp Leu Lys Ile Gly
                20              25              30
Ser Ser Met Asn Thr Met Val Ile Gln Thr Ala Asn Ser Ala Ser Glu
                35              40              45
Leu Phe Arg Asn His Asp Val Ser Phe Ser Asp Arg Pro Ile Val Asp
                50              55              60
Val Asn Leu Ala His Asn Tyr Tyr Lys Gly Ser Met Ala Leu Ala Pro
 65              70              75                              80
Tyr Gly Asn Tyr Trp Arg Phe Ser Arg Arg Ile Cys Thr Val Glu Met
                        85              90              95
Phe Val His Lys Arg Ile Asn Glu Thr Thr Asn Ile Arg Gln Glu Ser
                100             105             110
Val Asp Lys Met Leu Arg Leu Asp Glu Glu Lys Ala Ser Ser Ser Gly
                115             120             125
Gly Gly Gly Glu Gly Ile Glu Val Thr Arg Tyr Met Phe Leu Ala Ser
                130             135             140
Phe Asn Met Val Gly Asn Met Ile Phe Ser Lys Asp Leu Val Thr Asp
145             150             155                             160
Pro Glu Ser Lys Gln Gly Ser Glu Phe Asn Ala Met Ile Gly Ile
                        165             170             175
Met Glu Trp Ala Gly Val Pro Asn Ile Ser Asp Ile Phe Pro Cys Leu
                180             185             190
Lys Met Phe Asp Val Gln Gly Leu Arg Lys Met Glu Arg Asp Met
                        195             200             205
Gly Lys Gly Lys Glu Ile Thr Lys Lys Phe Ile Glu Glu Arg Ile Glu
                210             215             220
Glu Arg Lys Lys Gly Glu Lys Asn Arg Ser Ile Lys Asp Leu Leu Asp
225             230             235                             240
Val Leu Ile Asp Phe Glu Gly Ser Gly Lys Asp Glu Pro Asp Lys Leu
                        245             250             255
Ser Glu Asp Glu Ile Ile Val Ile Ile Leu Glu Met Phe Leu Ala Gly
                260             265             270
Thr Glu Thr Thr Ser Ser Ser Val Glu Trp Ala Leu Thr Glu Leu Leu
                275             280             285
Arg His Pro Gln Ala Met Ala Lys Val Lys Leu Glu Ile Leu Gln Val
                290             295             300
Ile Gly Pro Asn Lys Lys Phe Glu Glu Cys Asp Ile Asp Ser Leu Pro
305             310                     315                     320
Tyr Val Gln Ala Val Leu Lys Glu Gln Leu Arg Leu His Pro Pro Leu
                        325                     330             335
Pro Leu Leu Ile Pro Arg Lys Ala Ile Gln Asp Thr Lys Phe Met Gly
                340                     345             350
Tyr Asp Ile Pro Lys Gly Thr Gln Val Leu Val Asn Ala Trp Ala Ile
                355             360             365
Gly Arg Asp Pro Glu Tyr Trp Asp Asn Pro Phe Glu Phe Lys Pro Glu
                370             375             380
Arg Phe Leu Glu Ser Lys Val Asp Val Lys Gly Gln Asn Tyr Glu Leu
385             390             395                             400
Ile Pro Phe Gly Ala Gly Arg Arg Met Cys Val Gly Leu Pro Leu Gly
                        405             410             415
His Arg Met Met His Phe Thr Phe Gly Ser Leu Leu His Glu Phe Asp
                420             425             430
```

```
Trp Glu Leu Pro His Asn Val Ser Pro Lys Ser Ile Asn Met Glu Glu
            435                 440                 445

Ser Met Gly Ile Thr Ala Arg Lys Lys Gln Pro Leu Lys Val Ile Pro
    450                 455                 460

Lys Lys Ala
465

<210> SEQ ID NO 18
<211> LENGTH: 504
<212> TYPE: PRT
<213> ORGANISM: Solanum melongena

<400> SEQUENCE: 18

Met Glu Trp Glu Trp Ser Tyr Val Phe Phe Ser Ala Ile Ile Ile Leu
 1               5                  10                  15

Pro Ala Phe Ile Leu Phe Phe Ser Gln Lys Asn Thr Thr Lys Ser Ser
            20                  25                  30

Tyr Arg Pro Pro Gly Pro Pro Gly Leu Pro Ile Phe Gly Asn Met Phe
        35                  40                  45

Glu Leu Gly Thr Glu Pro Tyr Lys Lys Met Ala Val Leu Arg Gln Lys
    50                  55                  60

Tyr Gly Pro Val Leu Trp Leu Lys Glu Gly Ser Thr Tyr Thr Met Val
65                  70                  75                  80

Val Gln Thr Ala Gln Ala Ser Glu Glu Leu Phe Lys Asn His Asp Ile
            85                  90                  95

Ser Phe Ala Asn Arg Val Ile Pro Asp Val Asn Gln Ala His Ser Tyr
            100                 105                 110

Tyr Gln Gly Ser Leu Ala Ile Ala Pro Tyr Gly Pro Phe Trp Arg Phe
        115                 120                 125

Gln Arg Arg Ile Cys Thr Ile Glu Met Phe Val His Lys Lys Ile Ser
    130                 135                 140

Glu Thr Glu Pro Val Arg Arg Lys Cys Val Asp Asn Met Leu Lys Trp
145                 150                 155                 160

Ile Glu Lys Glu Ala Asn Ser Ala Glu Lys Gly Ser Gly Ile Glu Val
                165                 170                 175

Thr Arg Phe Val Phe Leu Ala Ser Phe Asn Met Leu Gly Asn Leu Ile
            180                 185                 190

Leu Ser Lys Asp Leu Ala Asp Leu Glu Ser Glu Glu Ala Ser Glu Phe
        195                 200                 205

Phe Ile Ala Met Lys Arg Ile Asn Glu Trp Ser Gly Ile Ala Asn Val
    210                 215                 220

Ser Asp Ile Phe Pro Phe Leu Lys Lys Phe Asp Leu Gln Ser Leu Arg
225                 230                 235                 240

Lys Lys Met Ala Arg Asp Met Gly Lys Ala Val Glu Ile Met Ser Met
                245                 250                 255

Phe Leu Lys Glu Arg Glu Glu Arg Lys Lys Gly Thr Glu Lys Gly
            260                 265                 270

Lys Asp Phe Leu Asp Val Leu Leu Glu Phe Gln Gly Thr Gly Lys Asp
        275                 280                 285

Glu Pro Ala Lys Leu Ser Glu His Glu Ile Lys Ile Phe Val Leu Glu
    290                 295                 300

Met Phe Leu Ala Gly Thr Glu Thr Thr Ser Ser Ser Val Glu Trp Ala
305                 310                 315                 320

Leu Thr Glu Leu Leu Arg His Pro Glu Ala Met Ala Lys Val Lys Thr
```

```
                    325                 330                 335
Glu Ile Ser Gln Ala Ile Glu Pro Asn Arg Lys Phe Glu Asp Ser Asp
                340                 345                 350
Ile Glu Asn Leu Pro Tyr Met Gln Ala Val Leu Lys Glu Ser Leu Arg
                355                 360                 365
Leu His Pro Pro Leu Pro Phe Leu Ile Pro Arg Glu Thr Ile Gln Asp
            370                 375                 380
Thr Lys Phe Met Gly Tyr Asp Val Pro Lys Asp Thr Gln Val Leu Val
385                 390                 395                 400
Asn Ala Trp Ala Ile Gly Arg Asp Pro Glu Cys Trp Asp Asp Pro Met
                405                 410                 415
Ser Phe Lys Pro Glu Arg Phe Leu Gly Ser Lys Ile Asp Val Lys Gly
                420                 425                 430
Gln His Tyr Gly Leu Ile Pro Phe Gly Ala Gly Arg Arg Met Cys Val
            435                 440                 445
Gly Leu Pro Leu Gly His Arg Met Met His Phe Ala Leu Gly Ser Leu
        450                 455                 460
Leu Arg Glu Phe Glu Trp Glu Leu Pro Asp Gly Val Ser Pro Lys Ser
465                 470                 475                 480
Ile Asn Met Asp Gly Ser Met Gly Val Thr Ala Arg Lys Arg Asp Ser
                485                 490                 495
Leu Lys Val Ile Pro Lys Lys Ala
            500

<210> SEQ ID NO 19
<211> LENGTH: 508
<212> TYPE: PRT
<213> ORGANISM: Petunia x hybrida

<400> SEQUENCE: 19

Met Val Leu Leu Ser Glu Leu Ala Ala Ala Thr Leu Ile Phe Leu Thr
  1               5                  10                  15
Thr His Ile Phe Ile Ser Thr Leu Leu Ser Ile Thr Asn Gly Arg Arg
                20                  25                  30
Leu Pro Pro Gly Pro Arg Gly Trp Pro Val Ile Gly Ala Leu Pro Leu
            35                  40                  45
Leu Gly Ala Met Pro His Val Ser Leu Ala Lys Met Ala Lys Lys Tyr
        50                  55                  60
Gly Ala Ile Met Tyr Leu Lys Val Gly Thr Cys Gly Met Val Val Ala
 65                  70                  75                  80
Ser Thr Pro Asp Ala Ala Lys Ala Phe Leu Lys Thr Leu Asp Leu Asn
                85                  90                  95
Phe Ser Asn Arg Pro Pro Asn Ala Gly Ala Thr His Leu Ala Tyr Gly
                100                 105                 110
Ala Gln Asp Met Val Phe Ala His Tyr Gly Pro Arg Trp Lys Leu Leu
            115                 120                 125
Arg Lys Leu Ser Asn Leu His Met Leu Gly Gly Lys Ala Leu Glu Asn
        130                 135                 140
Trp Ala Asn Val Arg Ala Asn Glu Leu Gly His Met Leu Lys Ser Met
145                 150                 155                 160
Phe Asp Met Ser Arg Glu Gly Glu Arg Val Val Ala Glu Met Leu
                165                 170                 175
Thr Phe Ala Met Ala Asn Met Ile Gly Gln Val Ile Leu Ser Lys Arg
            180                 185                 190
```

-continued

```
Val Phe Val Asn Lys Gly Val Glu Val Asn Glu Phe Lys Asp Met Val
            195                 200                 205

Val Glu Leu Met Thr Thr Ala Gly Tyr Phe Asn Ile Gly Asp Phe Ile
        210                 215                 220

Pro Cys Leu Ala Trp Met Asp Leu Gln Gly Ile Glu Lys Gly Met Lys
225                 230                 235                 240

Arg Leu His Lys Lys Phe Asp Ala Leu Leu Thr Arg Met Phe Asp Glu
                245                 250                 255

His Lys Ala Thr Ser Tyr Glu Arg Lys Gly Lys Pro Asp Phe Leu Asp
            260                 265                 270

Cys Val Met Glu Asn Arg Asp Asn Ser Glu Gly Glu Arg Leu Ser Thr
        275                 280                 285

Thr Asn Ile Lys Ala Leu Leu Leu Asn Leu Phe Thr Ala Gly Thr Asp
    290                 295                 300

Thr Ser Ser Ser Ala Ile Glu Trp Ala Leu Ala Glu Met Met Lys Asn
305                 310                 315                 320

Pro Ala Ile Leu Lys Lys Ala Gln Gly Glu Met Asp Gln Val Ile Gly
                325                 330                 335

Asn Asn Arg Arg Leu Leu Glu Ser Asp Ile Pro Asn Leu Pro Tyr Leu
            340                 345                 350

Arg Ala Ile Cys Lys Glu Thr Phe Arg Lys His Pro Ser Thr Pro Leu
        355                 360                 365

Asn Leu Pro Arg Ile Ser Asn Glu Pro Cys Ile Val Asp Gly Tyr Tyr
    370                 375                 380

Thr Pro Lys Asn Thr Arg Leu Ser Val Asn Ile Trp Ala Ile Gly Arg
385                 390                 395                 400

Asp Pro Glu Val Trp Glu Asn Pro Leu Glu Phe Tyr Pro Glu Arg Phe
                405                 410                 415

Leu Ser Gly Arg Asn Ser Lys Ile Asp Pro Arg Gly Asn Asp Phe Glu
            420                 425                 430

Leu Ile Pro Phe Gly Ala Gly Arg Arg Ile Cys Ala Gly Thr Arg Met
        435                 440                 445

Gly Ile Val Met Val Glu Tyr Ile Leu Gly Ile Leu Val His Ser Phe
    450                 455                 460

Asp Trp Lys Leu Pro Ser Glu Val Ile Glu Leu Asn Met Glu Glu Ala
465                 470                 475                 480

Phe Gly Leu Ala Leu Gln Lys Ala Val Pro Leu Glu Ala Met Val Ile
                485                 490                 495

Pro Arg Leu Pro Ile Asp Val Tyr Ala Pro Leu Ala
            500                 505
```

<210> SEQ ID NO 20
<211> LENGTH: 471
<212> TYPE: PRT
<213> ORGANISM: Persea americana

<400> SEQUENCE: 20

```
Met Ala Ile Leu Val Ser Leu Leu Phe Leu Ala Ile Ala Leu Thr Phe
1               5                   10                  15

Phe Leu Leu Lys Leu Asn Glu Lys Arg Glu Lys Lys Pro Asn Leu Pro
            20                  25                  30

Pro Ser Pro Pro Asn Leu Pro Ile Ile Gly Asn Leu His Gln Leu Gly
        35                  40                  45

Asn Leu Pro His Arg Ser Leu Arg Ser Leu Ala Asn Glu Leu Gly Pro
    50                  55                  60
```

-continued

```
Leu Ile Leu Leu His Leu Gly His Ile Pro Thr Leu Ile Val Ser Thr
 65                  70                  75                  80

Ala Glu Ile Ala Glu Glu Ile Leu Lys Thr His Asp Leu Ile Phe Ala
                 85                  90                  95

Ser Arg Pro Ser Thr Thr Ala Ala Arg Arg Ile Phe Tyr Asp Cys Thr
            100                 105                 110

Asp Val Ala Phe Ser Pro Tyr Gly Glu Tyr Trp Arg Gln Val Arg Lys
        115                 120                 125

Ile Cys Val Leu Glu Leu Leu Ser Ile Lys Arg Val Asn Ser Tyr Arg
    130                 135                 140

Ser Ile Arg Glu Glu Glu Val Gly Leu Met Met Glu Arg Ile Ser Gln
145                 150                 155                 160

Ser Cys Ser Thr Gly Glu Ala Val Asn Leu Ser Glu Leu Leu Leu Leu
                165                 170                 175

Leu Ser Ser Gly Thr Ile Thr Arg Val Ala Phe Gly Lys Lys Tyr Glu
            180                 185                 190

Gly Glu Glu Glu Arg Lys Asn Lys Phe Ala Asp Leu Ala Thr Glu Leu
        195                 200                 205

Thr Thr Leu Met Gly Ala Phe Phe Val Gly Asp Tyr Phe Pro Ser Phe
    210                 215                 220

Ala Trp Val Asp Val Leu Thr Gly Met Asp Ala Arg Leu Lys Arg Asn
225                 230                 235                 240

His Gly Glu Leu Asp Ala Phe Val Asp His Val Ile Asp Asp His Leu
                245                 250                 255

Leu Ser Arg Lys Ala Asn Gly Ser Asp Gly Val Glu Gln Lys Asp Leu
            260                 265                 270

Val Asp Val Leu Leu His Leu Gln Lys Asp Ser Ser Leu Gly Val His
        275                 280                 285

Leu Asn Arg Asn Asn Leu Lys Ala Val Ile Leu Asp Met Phe Ser Gly
    290                 295                 300

Gly Thr Asp Thr Thr Ala Val Ile Leu Glu Trp Ala Met Ala Glu Leu
305                 310                 315                 320

Ile Lys His Pro Asp Val Met Glu Lys Ala Gln Gln Glu Val Arg Arg
                325                 330                 335

Val Val Gly Lys Lys Ala Lys Val Glu Glu Glu Asp Leu His Gln Leu
            340                 345                 350

His Tyr Leu Lys Leu Ile Ile Lys Glu Thr Leu Arg Leu His Pro Val
        355                 360                 365

Ala Pro Leu Leu Val Pro Arg Glu Ser Thr Arg Asp Val Val Ile Arg
    370                 375                 380

Gly Tyr His Ile Pro Ala Lys Thr Arg Val Phe Ile Asn Ala Trp Ala
385                 390                 395                 400

Ile Gly Arg Asp Pro Lys Ser Trp Glu Asn Ala Glu Glu Phe Leu Pro
                405                 410                 415

Glu Arg Phe Val Asn Asn Ser Val Asp Phe Lys Gly Gln Asp Phe Gln
            420                 425                 430

Leu Ile Pro Phe Gly Ala Gly Arg Arg Gly Cys Pro Gly Ile Ala Phe
        435                 440                 445

Gly Ile Ser Ser Val Glu Ile Ser Leu Ala Asn Leu Leu Tyr Trp Phe
    450                 455                 460

Asn Trp Glu Leu Pro Gly Ile
465                 470
```

<210> SEQ ID NO 21
<211> LENGTH: 487
<212> TYPE: PRT
<213> ORGANISM: Berberis stolonifera

<400> SEQUENCE: 21

```
Met Asp Tyr Ile Val Gly Phe Val Ser Ile Ser Leu Val Ala Leu Leu
 1               5                  10                  15

Tyr Phe Leu Leu Phe Lys Pro Lys His Thr Asn Leu Pro Pro Ser Pro
            20                  25                  30

Pro Ala Trp Pro Ile Val Gly His Leu Pro Asp Leu Ile Ser Lys Asn
        35                  40                  45

Ser Pro Pro Phe Leu Asp Tyr Met Ser Asn Ile Ala Gln Lys Tyr Gly
    50                  55                  60

Pro Leu Ile His Leu Lys Phe Gly Leu His Ser Ser Ile Phe Ala Ser
65                  70                  75                  80

Thr Lys Glu Ala Ala Met Glu Val Leu Gln Thr Asn Asp Lys Val Leu
                85                  90                  95

Ser Gly Arg Gln Pro Leu Pro Cys Phe Arg Ile Lys Pro His Ile Asp
            100                 105                 110

Tyr Ser Ile Leu Trp Ser Asp Ser Asn Ser Tyr Trp Lys Lys Gly Arg
        115                 120                 125

Lys Ile Leu His Thr Glu Ile Phe Ser Gln Lys Met Leu Gln Ala Gln
    130                 135                 140

Glu Lys Asn Arg Glu Arg Val Ala Gly Asn Leu Val Asn Phe Ile Met
145                 150                 155                 160

Thr Lys Val Gly Asp Val Val Glu Leu Arg Ser Trp Leu Phe Gly Cys
                165                 170                 175

Ala Leu Asn Val Leu Gly His Val Val Phe Ser Asn Asp Val Phe Glu
            180                 185                 190

Tyr Ser Asp Gln Ser Asp Glu Val Gly Met Asp Lys Leu Ile His Gly
        195                 200                 205

Met Leu Met Thr Gly Gly Asp Phe Asp Val Ala Ser Tyr Phe Pro Val
    210                 215                 220

Leu Ala Arg Phe Asp Leu His Gly Leu Lys Arg Lys Met Asp Glu Gln
225                 230                 235                 240

Phe Lys Leu Leu Ile Lys Ile Trp Glu Gly Glu Val Leu Ala Arg Arg
                245                 250                 255

Ala Asn Arg Asn Pro Glu Pro Lys Asp Met Leu Asp Val Leu Ile Ala
            260                 265                 270

Asn Asp Phe Asn Glu His Gln Ile Asn Ala Met Phe Met Glu Thr Phe
        275                 280                 285

Gly Pro Gly Ser Asp Thr Asn Ser Asn Ile Ile Glu Trp Ala Leu Ala
    290                 295                 300

Gln Leu Ile Lys Asn Pro Asp Lys Leu Ala Lys Leu Arg Glu Glu Leu
305                 310                 315                 320

Asp Arg Val Val Gly Arg Ser Ser Thr Val Lys Glu Ser His Phe Ser
                325                 330                 335

Glu Leu Pro Tyr Leu Gln Ala Cys Val Lys Lys Thr Met Arg Leu Tyr
            340                 345                 350

Pro Pro Ile Ser Ile Met Ile Pro His Arg Cys Met Glu Ile Cys Gln
        355                 360                 365

Val Met Gly Tyr Thr Ile Pro Lys Gly Met Asp Val His Val Asn Ala
    370                 375                 380
```

-continued

```
His Ala Ile Gly Arg Asp Pro Lys Asp Trp Lys Asp Pro Leu Lys Phe
385                 390                 395                 400

Gln Pro Glu Arg Phe Leu Asp Ser Asp Ile Glu Tyr Asn Gly Lys Gln
            405                 410                 415

Phe Gln Phe Ile Pro Phe Gly Ser Gly Arg Arg Ile Cys Pro Gly Arg
            420                 425                 430

Pro Leu Ala Val Arg Ile Ile Pro Leu Val Leu Ala Ser Leu Val His
            435                 440                 445

Ala Phe Gly Trp Glu Leu Pro Asp Gly Val Pro Asn Glu Lys Leu Asp
    450                 455                 460

Met Glu Glu Leu Phe Thr Leu Ser Leu Cys Met Ala Lys Pro Leu Arg
465                 470                 475                 480

Val Ile Pro Lys Val Arg Ile
                485

<210> SEQ ID NO 22
<211> LENGTH: 505
<212> TYPE: PRT
<213> ORGANISM: Helianthus tuberosus

<400> SEQUENCE: 22

Met Asp Leu Leu Leu Ile Glu Lys Thr Leu Val Ala Leu Phe Ala Ala
 1               5                  10                  15

Ile Ile Gly Ala Ile Leu Ile Ser Lys Leu Arg Gly Lys Lys Phe Lys
                20                  25                  30

Leu Pro Pro Gly Pro Ile Pro Val Pro Ile Phe Gly Asn Trp Leu Gln
            35                  40                  45

Val Gly Asp Asp Leu Asn His Arg Asn Leu Thr Asp Leu Ala Lys Arg
    50                  55                  60

Phe Gly Glu Ile Ile Leu Leu Arg Met Gly Gln Arg Asn Leu Val Val
65                  70                  75                  80

Val Ser Ser Pro Glu Leu Ala Lys Glu Val Leu His Thr Gln Gly Val
                85                  90                  95

Glu Phe Gly Ser Arg Thr Arg Asn Val Val Phe Asp Ile Phe Thr Gly
            100                 105                 110

Lys Gly Gln Asp Met Val Phe Thr Val Tyr Gly Glu His Trp Arg Lys
        115                 120                 125

Met Arg Arg Ile Met Thr Val Pro Phe Phe Thr Asn Lys Val Val Gln
130                 135                 140

Gln Tyr Arg Tyr Gly Trp Glu Ala Glu Ala Ala Ala Val Val Asp Asp
145                 150                 155                 160

Val Lys Lys Asn Pro Ala Ala Ala Thr Glu Gly Ile Val Ile Arg Arg
                165                 170                 175

Arg Leu Gln Leu Met Met Tyr Asn Asn Met Phe Arg Ile Met Phe Asp
            180                 185                 190

Arg Arg Phe Glu Ser Glu Asp Asp Pro Leu Phe Leu Lys Leu Lys Ala
        195                 200                 205

Leu Asn Gly Glu Arg Ser Arg Leu Ala Gln Ser Phe Glu Tyr Asn Tyr
    210                 215                 220

Gly Asp Phe Ile Pro Ile Leu Arg Pro Phe Leu Arg Asn Tyr Leu Lys
225                 230                 235                 240

Leu Cys Lys Glu Val Lys Asp Lys Arg Ile Gln Leu Phe Lys Asp Tyr
                245                 250                 255

Phe Val Asp Glu Arg Lys Lys Ile Gly Ser Thr Lys Lys Met Asp Asn
```

```
                    260                 265                 270
Asn Gln Leu Lys Cys Ala Ile Asp His Ile Leu Glu Ala Lys Glu Lys
            275                 280                 285

Gly Glu Ile Asn Glu Asp Asn Val Leu Tyr Ile Val Glu Asn Ile Asn
        290                 295                 300

Val Ala Ala Ile Glu Thr Thr Leu Trp Ser Ile Glu Trp Gly Ile Ala
305                 310                 315                 320

Glu Leu Val Asn His Pro Glu Ile Gln Ala Lys Leu Arg His Glu Leu
                325                 330                 335

Asp Thr Lys Leu Gly Pro Gly Val Gln Ile Thr Glu Pro Asp Val Gln
            340                 345                 350

Asn Leu Pro Tyr Leu Gln Ala Val Val Lys Glu Thr Leu Arg Leu Arg
        355                 360                 365

Met Ala Ile Pro Leu Leu Val Glu His Met Asn Leu His Asp Ala Lys
    370                 375                 380

Leu Gly Gly Phe Asp Ile Pro Ala Glu Ser Lys Ile Leu Val Asn Ala
385                 390                 395                 400

Trp Trp Leu Ala Asn Asn Pro Asp Gln Trp Lys Lys Pro Glu Glu Phe
                405                 410                 415

Arg Pro Glu Arg Phe Leu Glu Glu Ala Lys Val Glu Ala Asn Gly
            420                 425                 430

Asn Asp Phe Arg Tyr Leu Pro Phe Gly Val Gly Arg Arg Ser Cys Pro
        435                 440                 445

Gly Ile Ile Leu Ala Leu Pro Ile Leu Gly Ile Thr Ile Gly Arg Leu
    450                 455                 460

Val Gln Asn Phe Glu Leu Leu Pro Pro Gly Gln Ser Lys Ile Asp
465                 470                 475                 480

Thr Asp Glu Lys Gly Gly Gln Phe Ser Leu His Ile Leu Lys His Ser
                485                 490                 495

Thr Ile Val Ala Lys Pro Arg Ser Phe
            500                 505

<210> SEQ ID NO 23
<211> LENGTH: 504
<212> TYPE: PRT
<213> ORGANISM: Mus musculus

<400> SEQUENCE: 23

Met Glu Leu Leu Thr Gly Ala Gly Leu Trp Ser Val Ala Ile Phe Thr
1               5                   10                  15

Val Ile Phe Ile Leu Leu Val Asp Leu Met His Arg His Gln Arg Trp
            20                  25                  30

Thr Ser Arg Tyr Pro Pro Gly Pro Val Pro Trp Pro Val Leu Gly Asn
        35                  40                  45

Leu Leu Gln Val Asp Leu Asp Asn Met Pro Tyr Ser Leu Tyr Lys Leu
    50                  55                  60

Gln Asn Arg Tyr Gly Asp Val Phe Ser Leu Gln Met Gly Trp Lys Pro
65                  70                  75                  80

Met Val Val Ile Asn Gly Leu Lys Ala Met Lys Glu Val Leu Leu Thr
                85                  90                  95

Cys Gly Glu Asp Thr Ala Asp Arg Pro Gln Val Pro Ile Phe Glu Tyr
            100                 105                 110

Leu Gly Val Lys Pro Gly Ser Gln Gly Val Val Leu Ala Pro Tyr Gly
        115                 120                 125
```

```
Pro Glu Trp Arg Glu Gln Arg Arg Phe Ser Val Ser Thr Leu Arg Asn
    130                 135                 140

Phe Gly Leu Gly Lys Lys Ser Leu Glu Asp Trp Val Thr Lys Glu Ala
145                 150                 155                 160

Arg His Leu Cys Asp Ala Phe Thr Ala Gln Ala Gly Gln Pro Ile Asn
                165                 170                 175

Pro Asn Thr Met Leu Asn Asn Ala Val Cys Asn Val Ile Ala Ser Leu
            180                 185                 190

Ile Phe Ala Arg Arg Phe Glu Tyr Glu Asp Pro Tyr Leu Ile Arg Met
        195                 200                 205

Gln Lys Val Leu Glu Asp Ser Leu Thr Glu Ile Ser Leu Ala Tyr Ser
    210                 215                 220

Glu Val Leu Asn Met Phe Pro Ile Leu Leu Arg Ile Pro Gly Leu Pro
225                 230                 235                 240

Gly Lys Val Phe Gln Gly Gln Lys Ser Leu Leu Ala Ile Val Glu Asn
                245                 250                 255

Leu Leu Thr Glu Asn Arg Asn Thr Trp Asp Pro Asp Gln Pro Pro Arg
            260                 265                 270

Asn Leu Thr Asp Ala Phe Leu Ala Glu Ile Glu Lys Val Lys Gly Asn
        275                 280                 285

Ala Glu Ser Ser Phe Asn Asp Glu Asn Leu Arg Met Val Val Leu Asp
    290                 295                 300

Leu Phe Thr Ala Gly Met Val Thr Thr Ser Thr Thr Leu Ser Trp Ala
305                 310                 315                 320

Leu Leu Leu Met Ile Leu His Pro Asp Val Gln Arg Arg Val Gln Gln
                325                 330                 335

Glu Ile Asp Ala Val Ile Gly Gln Val Arg His Pro Glu Met Ala Asp
            340                 345                 350

Gln Ala Arg Met Pro Tyr Thr Asn Ala Val Ile His Glu Val Gln Arg
        355                 360                 365

Phe Gly Asp Ile Ala Pro Leu Asn Leu Pro Arg Ile Thr Ser Arg Asp
    370                 375                 380

Ile Glu Val Gln Asp Phe Leu Ile Pro Lys Gly Ser Ile Leu Ile Pro
385                 390                 395                 400

Asn Met Ser Ser Val Leu Lys Asp Glu Thr Val Trp Glu Lys Pro Leu
                405                 410                 415

Arg Phe His Pro Glu His Phe Leu Asp Ala Gln Gly His Phe Val Lys
            420                 425                 430

Pro Glu Ala Phe Met Pro Phe Ser Ala Gly Arg Arg Ser Cys Leu Gly
        435                 440                 445

Glu Pro Leu Ala Arg Met Glu Leu Phe Leu Phe Phe Ile Cys Leu Leu
    450                 455                 460

Gln His Phe Ser Phe Ser Val Pro Asn Gly Gln Pro Arg Pro Arg Asn
465                 470                 475                 480

Leu Gly Val Phe Pro Phe Pro Val Ala Pro Tyr Pro Tyr Gln Leu Cys
                485                 490                 495

Ala Val Met Arg Glu Gln Gly His
            500
```

<210> SEQ ID NO 24
<211> LENGTH: 524
<212> TYPE: PRT
<213> ORGANISM: Rattus norvegicus

<400> SEQUENCE: 24

-continued

```
Met Pro Ser Val Tyr Gly Phe Pro Ala Phe Thr Ser Ala Thr Glu Leu
 1               5                  10                  15

Leu Leu Ala Val Thr Thr Phe Cys Leu Gly Phe Trp Val Val Arg Val
             20                  25                  30

Thr Arg Thr Trp Val Pro Lys Gly Leu Lys Ser Pro Pro Gly Pro Trp
         35                  40                  45

Gly Leu Pro Phe Ile Gly His Val Leu Thr Leu Gly Lys Asn Pro His
     50                  55                  60

Leu Ser Leu Thr Lys Leu Ser Gln Gln Tyr Gly Asp Val Leu Gln Ile
 65              70                  75                  80

Arg Ile Gly Ser Thr Pro Val Val Leu Ser Gly Leu Asn Thr Ile
                 85                  90                  95

Lys Gln Ala Leu Val Lys Gln Gly Asp Asp Phe Lys Gly Arg Pro Asp
             100                 105                 110

Leu Tyr Ser Phe Thr Leu Ile Ala Asn Gly Gln Ser Met Thr Phe Asn
             115                 120                 125

Pro Asp Ser Gly Pro Leu Trp Ala Ala Arg Arg Leu Ala Gln Asn
 130                 135                 140

Ala Leu Lys Ser Phe Ser Ile Ala Ser Asp Pro Thr Leu Ala Ser Ser
 145                 150                 155                 160

Cys Tyr Leu Glu Glu His Val Ser Lys Glu Ala Glu Tyr Leu Ile Ser
                 165                 170                 175

Lys Phe Gln Lys Leu Met Ala Glu Val Gly His Phe Asp Pro Phe Lys
             180                 185                 190

Tyr Leu Val Val Ser Val Ala Asn Val Ile Cys Ala Ile Cys Phe Gly
             195                 200                 205

Arg Arg Tyr Asp His Asp Gln Glu Leu Leu Ser Ile Val Asn Leu
 210                 215                 220

Ser Asn Glu Phe Gly Glu Val Thr Gly Ser Gly Tyr Pro Ala Asp Phe
 225                 230                 235                 240

Ile Pro Ile Leu Arg Tyr Leu Pro Asn Ser Ser Leu Asp Ala Phe Lys
                 245                 250                 255

Asp Leu Asn Lys Lys Phe Tyr Ser Phe Met Lys Lys Leu Ile Lys Glu
             260                 265                 270

His Tyr Arg Thr Phe Glu Lys Gly His Ile Arg Asp Ile Thr Asp Ser
         275                 280                 285

Leu Ile Glu His Cys Gln Asp Arg Arg Leu Asp Glu Asn Ala Asn Val
 290                 295                 300

Gln Leu Ser Asp Asp Lys Val Ile Thr Ile Val Phe Asp Leu Phe Gly
 305                 310                 315                 320

Ala Gly Phe Asp Thr Ile Thr Thr Ala Ile Ser Trp Ser Leu Met Tyr
             325                 330                 335

Leu Val Thr Asn Pro Arg Ile Gln Arg Lys Ile Gln Glu Glu Leu Asp
             340                 345                 350

Thr Val Ile Gly Arg Asp Arg Gln Pro Arg Leu Ser Asp Arg Pro Gln
             355                 360                 365

Leu Pro Tyr Leu Glu Ala Phe Ile Leu Glu Thr Phe Arg His Ser Ser
 370                 375                 380

Phe Val Pro Phe Thr Ile Pro His Ser Thr Ile Arg Asp Thr Ser Leu
 385                 390                 395                 400

Asn Gly Phe Tyr Ile Pro Lys Gly His Cys Val Phe Val Asn Gln Trp
                 405                 410                 415
```

```
Gln Val Asn His Asp Gln Glu Leu Trp Gly Asp Pro Asn Glu Phe Arg
            420                 425                 430

Pro Glu Arg Phe Leu Thr Ser Ser Gly Thr Leu Asp Lys His Leu Ser
            435                 440                 445

Glu Lys Val Ile Leu Phe Gly Leu Gly Lys Arg Lys Cys Ile Gly Glu
            450                 455                 460

Ile Ile Gly Arg Leu Glu Val Phe Leu Phe Leu Ala Ile Leu Leu Gln
465                 470                 475                 480

Gln Met Glu Phe Asn Val Ser Pro Gly Glu Lys Val Asp Met Thr Pro
            485                 490                 495

Ala Tyr Gly Leu Thr Leu Lys His Ala Arg Cys Glu His Phe Gln Val
            500                 505                 510

Gln Met Arg Ser Ser Gly Pro Gln His Leu Gln Ala
            515                 520

<210> SEQ ID NO 25
<211> LENGTH: 508
<212> TYPE: PRT
<213> ORGANISM: Homo sapiens

<400> SEQUENCE: 25

Met Trp Glu Leu Val Ala Leu Leu Leu Thr Leu Ala Tyr Leu Phe
1               5                   10                  15

Trp Pro Lys Arg Arg Cys Pro Gly Ala Lys Tyr Pro Lys Ser Leu Leu
            20                  25                  30

Ser Leu Pro Leu Val Gly Ser Leu Pro Phe Leu Pro Arg His Gly His
            35                  40                  45

Met His Asn Asn Phe Phe Lys Leu Gln Lys Lys Tyr Gly Pro Ile Tyr
        50                  55                  60

Ser Val Arg Met Gly Thr Lys Thr Thr Val Ile Val Gly His His Gln
65                  70                  75                  80

Leu Ala Lys Glu Val Leu Ile Lys Lys Gly Lys Asp Phe Ser Gly Arg
            85                  90                  95

Pro Gln Met Ala Thr Leu Asp Ile Ala Ser Asn Asn Arg Lys Gly Ile
            100                 105                 110

Ala Pro Ala Asp Ser Gly Ala His Trp Gln Leu His Arg Arg Leu Ala
            115                 120                 125

Met Ala Thr Phe Ala Leu Phe Lys Asp Gly Asp Gln Lys Leu Glu Lys
            130                 135                 140

Ile Ile Cys Gln Glu Ile Ser Thr Leu Cys Asp Met Leu Ala Thr His
145                 150                 155                 160

Asn Gly Gln Ser Ile Asp Ile Ser Phe Pro Val Phe Val Ala Val Thr
            165                 170                 175

Asn Val Ile Ser Leu Ile Cys Phe Asn Thr Ser Tyr Lys Asn Gly Asp
            180                 185                 190

Pro Glu Leu Asn Val Ile Gln Asn Tyr Asn Glu Gly Ile Ile Asp Asn
            195                 200                 205

Leu Ser Lys Asp Ser Leu Val Asp Leu Val Pro Trp Leu Lys Ile Phe
            210                 215                 220

Pro Asn Lys Thr Leu Glu Lys Leu Lys Ser His Val Lys Ile Arg Asn
225                 230                 235                 240

Asp Leu Leu Asn Lys Ile Leu Glu Asn Tyr Lys Glu Lys Phe Arg Ser
            245                 250                 255

Asp Ser Ile Thr Asn Met Leu Asp Thr Leu Met Gln Ala Lys Met Asn
            260                 265                 270
```

```
Ser Asp Asn Gly Asn Ala Gly Pro Asp Gln Asp Ser Glu Leu Leu Ser
        275                 280                 285

Asp Asn His Ile Leu Thr Thr Ile Gly Asp Ile Phe Gly Ala Gly Val
    290                 295                 300

Glu Thr Thr Thr Ser Val Val Lys Trp Thr Leu Ala Phe Leu Leu His
305                 310                 315                 320

Asn Pro Gln Val Lys Lys Leu Tyr Glu Glu Ile Asp Gln Asn Val
                325                 330                 335

Gly Phe Ser Arg Thr Pro Thr Ile Ser Asp Arg Asn Arg Leu Leu Leu
            340                 345                 350

Leu Glu Ala Thr Ile Arg Glu Val Leu Arg Leu Arg Pro Val Ala Pro
        355                 360                 365

Met Leu Ile Pro His Lys Ala Asn Val Asp Ser Ser Ile Gly Glu Phe
    370                 375                 380

Ala Val Asp Lys Gly Thr Glu Val Ile Ile Asn Leu Trp Ala Leu His
385                 390                 395                 400

His Asn Glu Lys Glu Trp His Gln Pro Asp Gln Phe Met Pro Glu Arg
                405                 410                 415

Phe Leu Asn Pro Ala Gly Thr Gln Leu Ile Ser Pro Ser Val Ser Tyr
            420                 425                 430

Leu Pro Phe Gly Ala Gly Pro Arg Ser Cys Ile Gly Glu Ile Leu Ala
        435                 440                 445

Arg Gln Glu Leu Phe Leu Ile Met Ala Trp Leu Leu Gln Arg Phe Asp
    450                 455                 460

Leu Glu Val Pro Asp Asp Gly Gln Leu Pro Ser Leu Glu Gly Ile Pro
465                 470                 475                 480

Lys Val Val Phe Leu Ile Asp Ser Phe Lys Val Lys Ile Lys Val Arg
                485                 490                 495

Gln Ala Trp Arg Glu Ala Gln Ala Glu Gly Ser Thr
            500                 505

<210> SEQ ID NO 26
<211> LENGTH: 494
<212> TYPE: PRT
<213> ORGANISM: Rattus norvegicus

<400> SEQUENCE: 26

Met Leu Ala Ser Gly Leu Leu Val Ala Ser Val Ala Phe Leu Ser
  1               5                  10                  15

Val Leu Val Leu Met Ser Val Trp Lys Gln Arg Lys Leu Ser Gly Lys
                 20                  25                  30

Leu Pro Pro Gly Pro Thr Pro Leu Pro Phe Ile Gly Asn Tyr Leu Gln
             35                  40                  45

Leu Asn Thr Glu Lys Met Tyr Ser Ser Leu Met Lys Ile Ser Gln Arg
         50                  55                  60

Tyr Gly Pro Val Phe Thr Ile His Leu Gly Pro Arg Arg Val Val Val
 65                  70                  75                  80

Leu Cys Gly Gln Glu Ala Val Lys Glu Ala Leu Val Asp Gln Ala Glu
                 85                  90                  95

Glu Phe Ser Gly Arg Gly Glu Gln Ala Thr Phe Asp Trp Leu Phe Lys
            100                 105                 110

Gly Tyr Gly Val Ala Phe Ser Ser Gly Glu Arg Ala Lys Gln Leu Arg
        115                 120                 125

Arg Phe Ser Ile Ala Thr Leu Arg Asp Phe Gly Val Gly Lys Arg Gly
```

```
                130                 135                 140
Ile Glu Glu Arg Ile Gln Glu Glu Ala Gly Phe Leu Ile Glu Ser Phe
145                 150                 155                 160

Arg Lys Thr Asn Gly Ala Leu Ile Asp Pro Thr Phe Tyr Leu Ser Arg
                165                 170                 175

Thr Val Ser Asn Val Ile Ser Ser Ile Val Phe Gly Asp Arg Phe Asp
                180                 185                 190

Tyr Glu Asp Lys Glu Phe Leu Ser Leu Leu Arg Met Met Leu Gly Ser
                195                 200                 205

Phe Gln Phe Thr Ala Thr Ser Thr Gly Gln Leu Tyr Glu Met Phe Ser
                210                 215                 220

Ser Val Met Lys His Leu Pro Gly Pro Gln Gln Ala Phe Lys Glu
225                 230                 235                 240

Leu Gln Gly Leu Glu Asp Phe Ile Thr Lys Lys Val Glu Gln Asn Gln
                245                 250                 255

Arg Thr Leu Asp Pro Asn Ser Pro Arg Asp Phe Ile Asp Ser Phe Leu
                260                 265                 270

Ile Arg Met Leu Glu Glu Lys Lys Asn Pro Asn Thr Glu Phe Tyr Met
                275                 280                 285

Lys Asn Leu Val Leu Thr Thr Leu Asn Leu Phe Phe Ala Gly Thr Glu
                290                 295                 300

Thr Val Ser Thr Thr Leu Arg Tyr Gly Phe Leu Leu Leu Met Arg His
305                 310                 315                 320

Pro Asp Ile Glu Ala Lys Val His Glu Glu Ile Asp Arg Val Ile Gly
                325                 330                 335

Arg Asn Arg Gln Ala Lys Tyr Glu Asp Arg Met Lys Met Pro Tyr Thr
                340                 345                 350

Glu Ala Val Ile His Glu Ile Gln Arg Phe Ala Asp Met Ile Pro Met
                355                 360                 365

Gly Leu Ala Arg Arg Val Thr Lys Asp Thr Lys Phe Arg Glu Phe Leu
                370                 375                 380

Leu Pro Lys Gly Thr Glu Val Phe Pro Met Leu Gly Ser Val Leu Lys
385                 390                 395                 400

Asp Pro Lys Phe Phe Ser Asn Pro Asn Asp Phe Asn Pro Lys His Phe
                405                 410                 415

Leu Asp Asp Lys Gly Gln Phe Lys Lys Ser Asp Ala Phe Val Pro Phe
                420                 425                 430

Ser Ile Gly Lys Arg Tyr Cys Phe Gly Glu Gly Leu Ala Arg Met Glu
                435                 440                 445

Leu Phe Leu Phe Leu Thr Asn Ile Met Gln Asn Phe Cys Phe Lys Ser
                450                 455                 460

Pro Gln Ala Pro Gln Asp Ile Asp Val Ser Pro Arg Leu Val Gly Phe
465                 470                 475                 480

Ala Thr Ile Pro Pro Asn Tyr Thr Met Ser Phe Leu Ser Arg
                485                 490
```

<210> SEQ ID NO 27
<211> LENGTH: 53
<212> TYPE: DNA
<213> ORGANISM: Artificial Sequence

```
<220> FEATURE:
<223> OTHER INFORMATION: Description of Artificial Sequence:  Antisense
      primer derived from Helianthus tuberosus CYP76B1 nucleic acid
      sequence

<400> SEQUENCE: 27
tatatagaat tcatgctaat gatgatgatg gttcaatggt attggaacaa cac          53
```